United States Patent
Miao et al.

(10) Patent No.: US 11,732,044 B2
(45) Date of Patent: **\*Aug. 22, 2023**

(54) ANTI-LAG-3 ANTIBODY AND USE THEREOF

(71) Applicant: INNOVENT BIOLOGICS (SUZHOU) CO., LTD., Jiangsu (CN)

(72) Inventors: Xiaoniu Miao, Jiangsu (CN); Huajing Hu, Jiangsu (CN); Andy Tsun, Jiangsu (CN); Junjian Liu, Jiangsu (CN); Xiaolin Liu, Jiangsu (CN)

(73) Assignee: INNOVENT BIOLOGICS (SUZHOU) CO., LTD., Jiangsu (CN)

( * ) Notice: Subject to any disclaimer, the term of this patent is extended or adjusted under 35 U.S.C. 154(b) by 118 days.

This patent is subject to a terminal disclaimer.

(21) Appl. No.: 16/759,722

(22) PCT Filed: Dec. 27, 2018

(86) PCT No.: PCT/CN2018/124315
§ 371 (c)(1),
(2) Date: Apr. 27, 2020

(87) PCT Pub. No.: WO2019/129137
PCT Pub. Date: Jul. 4, 2019

(65) Prior Publication Data
US 2021/0371529 A1 Dec. 2, 2021

(30) Foreign Application Priority Data

Dec. 27, 2017 (CN) .......................... 201711449486.7
Dec. 19, 2018 (CN) .......................... 201811561512.X

(51) Int. Cl.
*A61K 39/395* (2006.01)
*C07K 16/28* (2006.01)
(Continued)

(52) U.S. Cl.
CPC .......... *C07K 16/2818* (2013.01); *A61K 45/06* (2013.01); *A61K 47/6851* (2017.08);
(Continued)

(58) Field of Classification Search
None
See application file for complete search history.

(56) References Cited

U.S. PATENT DOCUMENTS 6,111,090 A 8/2000 Gorman et al.
8,586,023 B2 11/2013 Shiku et al.
(Continued)

FOREIGN PATENT DOCUMENTS

CN 101842387 A 9/2010
CN 103764665 A 4/2014
(Continued)

OTHER PUBLICATIONS

Ruffo et al., Lymphocyte-activation gene 3 (LAG3)_ The next immune checkpoint receptor, Sem. Immunol. 42:101305, doi.org/10.1016/j.smim.2019.101305, Apr. 2019.*
(Continued)

*Primary Examiner* — Claire Kaufman
(74) *Attorney, Agent, or Firm* — Leason Ellis LLP

(57) ABSTRACT

The invention relates to a novel antibody and an antibody fragment thereof that specifically bind to ALG-3 and a composition comprising the antibody or the antibody fragment. In addition, the invention relates to a nucleic acid encoding the antibody or the antibody fragment thereof, a host cell comprising the nucleic acid, and related use. Furthermore, the invention relates to therapeutic and diagnostic use of the antibody and the antibody fragment. In particular, the invention relates to combination therapy of
(Continued)

(A)

(B)

the antibodies and the antibody fragments described herein with other therapeutic agents, such as anti-PD-1 or anti-PD-L1 antibodies.

21 Claims, 8 Drawing Sheets

Specification includes a Sequence Listing.

(51) Int. Cl.
```
    A61K 47/68      (2017.01)
    A61K 45/06      (2006.01)
    C12N 15/85      (2006.01)
    A61K 39/00      (2006.01)
```
(52) U.S. Cl.
CPC ...... *C07K 16/2803* (2013.01); *C07K 16/2878* (2013.01); *C12N 15/85* (2013.01); *A61K 2039/507* (2013.01); *C07K 2317/24* (2013.01); *C07K 2317/31* (2013.01); *C07K 2317/52* (2013.01); *C07K 2317/565* (2013.01); *C07K 2317/732* (2013.01); *C07K 2317/76* (2013.01); *C07K 2317/92* (2013.01)

(56) References Cited

U.S. PATENT DOCUMENTS

| | | | |
|---|---|---|---|
| 10,280,221 | B2 | 5/2019 | Hamblin et al. |
| 2014/0093511 | A1 | 4/2014 | Lonberg et al. |
| 2014/0286935 | A1 | 9/2014 | Hamblin et al. |
| 2015/0203580 | A1 | 7/2015 | Papadopoulos et al. |
| 2016/0017037 | A1 | 1/2016 | Hamblin et al. |
| 2016/0176965 | A1 | 6/2016 | Haudebourg et al. |
| 2017/0101472 | A1 | 4/2017 | Ullman et al. |
| 2017/0137514 | A1 | 5/2017 | Lonberg et al. |
| 2018/0369375 | A1 | 12/2018 | De Waal Malefyt et al. |
| 2019/0010246 | A1 | 1/2019 | Liang et al. |
| 2019/0016800 | A1 | 1/2019 | Kang et al. |
| 2020/0332009 | A1* | 10/2020 | Miao ............ C07K 16/2803 |
| 2022/0112284 | A1 | 4/2022 | Ni et al. |

FOREIGN PATENT DOCUMENTS

| | | |
|---|---|---|
| CN | 105793287 A | 7/2016 |
| CN | 105992595 A | 10/2016 |
| CN | 106103484 A | 11/2016 |
| CN | 106188305 A | 12/2016 |
| CN | 106432502 A | 2/2017 |
| CN | 107474137 A | 12/2017 |
| CN | 107686520 A | 2/2018 |
| CN | 109970856 A | 7/2019 |
| CN | 109970857 A | 7/2019 |
| CN | 109970860 A | 7/2019 |
| EP | 3369745 A1 | 9/2018 |
| RU | 2252786 C2 | 5/2005 |
| TW | 201803906 A | 2/2018 |
| WO | 1994/04678 A1 | 3/1994 |
| WO | 2005103081 A2 | 11/2005 |
| WO | 2006121168 A1 | 11/2006 |
| WO | 2007/005874 A2 | 1/2007 |
| WO | 2008132601 A1 | 11/2008 |
| WO | 2009036379 A2 | 3/2009 |
| WO | 2009101611 A1 | 8/2009 |
| WO | 2009114335 A2 | 9/2009 |
| WO | 2010003118 A1 | 1/2010 |
| WO | 2010019570 A2 | 2/2010 |
| WO | 2010027827 A2 | 3/2010 |
| WO | 2010/077634 A2 | 7/2010 |
| WO | 2010105256 A1 | 9/2010 |
| WO | 2011/066389 A1 | 6/2011 |
| WO | 2011066342 A2 | 6/2011 |
| WO | 2011090754 A1 | 7/2011 |
| WO | 2012009568 A2 | 1/2012 |
| WO | 2012/177624 A1 | 12/2012 |
| WO | 2014/008218 A1 | 1/2014 |
| WO | 2014140180 A1 | 9/2014 |
| WO | 2015/042246 A1 | 3/2015 |
| WO | 2015095423 A2 | 6/2015 |
| WO | 2015/138920 A1 | 9/2015 |
| WO | 2015/153513 A1 | 10/2015 |
| WO | 2015197789 A1 | 12/2015 |
| WO | 2016/007235 A1 | 1/2016 |
| WO | 2016/028672 A1 | 2/2016 |
| WO | 2016/061142 A1 | 4/2016 |
| WO | 2017025016 A1 | 2/2017 |
| WO | 2017/037203 A1 | 3/2017 |
| WO | 2017062888 A1 | 4/2017 |
| WO | WO-2017133540 A1 * | 8/2017 ......... A61K 39/3955 |
| WO | 2017/196867 A1 | 11/2017 |
| WO | 2017198741 A1 | 11/2017 |
| WO | 2017/220569 A1 | 12/2017 |
| WO | 2017211321 A1 | 12/2017 |
| WO | 2018/014260 A1 | 1/2018 |
| WO | 2018014855 A1 | 1/2018 |
| WO | 2018/204374 A1 | 11/2018 |
| WO | 2018/222722 A2 | 12/2018 |
| WO | 2019129137 A1 | 7/2019 |

OTHER PUBLICATIONS

MacCallum et al., Antibody-antigen interactions: contact analysis and binding site topography, J. Mol. Biol. 262:732-745, 1996.*
Yan et al., Construction of a synthetic phage-displayed naonbody library with CDR3 regions randomized by trimucleotide cassettes for diagnostic applications, J. Transl. Med. 12:343, 2014.*
Written Opinion of the International Searching Authority of corresponding International Application PCT/CN2018/124315, dated Mar. 27, 2019, with English translation.
International Search Report of corresponding International Application PCT/CN2018/124315, dated Mar. 27, 2019, and English translation.
Andreae et al., Maturation and activation of dendritic cells induced by lymphocyte activation gene-3 (CD223), J Immunol. 168:3874-3880, 2002.
Baixeras et al., (1992) Characterization of the lymphocyte activation gene 3-encoded protein. A new ligand for human leukocyte antigen class II antigens, J. Exp. Med.176:327-337.
Huard et al. (1996) T cell major histocompatibility complex class II molecules down-regulate CD4+ T cell clone responses following LAG-3 binding, Eur. J. Immunol, 26:1180-1186.
Blackburn et al.,. Coregulation of CD8+ T cell exhaustion by multiple inhibitory receptors during chronic viral infection, Nat Immunol, 2009, 10:29-37.
Huard et al., Lymphocyte-activation gene 3/major histocompatibility complex class II interaction modulates the antigenic response of CD4+ T lymphocytes, (1994) Eur. J. Immunol. 24:3216-3221.
Jing et al., Combined immune checkpoint protein blockade and low dose whole body irradiation as immunotherapy for myeloma, Journal for ImmunoTherapy of Cancer, (2015) 3(1):2.
Sierro et al., "The CD4-like molecule LAG-3, biology and therapeutic applications", Expert Opin Ther Targets, 2011, 15(1):91-101.
Demeure et al., T Lymphocytes infiltrating various tumour types express the MHC class II ligand lymphocyte activation gene-3 (LAG-3): role of LAG-3/MHC class II interactions in cell-cell contacts, Eur. J. Cancer, 2001, 37 (13): 1709-1718.
Jones, Analysis of Polypeptides and Proteins, A. Adv. Drug Delivery Rev. 10: 29-90 (1993).
Chothia and Lesk, Canonical Structures for the Hypervariable Regions of Immunoglobulins, J. Mol. Biol. 196:901-917 (1987).
Tugcu et al., Maximizing productivity of chromatography steps for purification of monoclonal antibodies, Biotechnology and Bioengineering 99 (2008) 599-613.
Kelley et al., Weak partitioning chromatography for anion exchange purification of monoclonal antibodies, Biotechnology and Bioengineering, 101 (2008) 553-566.

(56) References Cited

OTHER PUBLICATIONS

Richard R. et al., Application of CE SDS gel in development of biopharmaceutical antibody-based products, Electrophoresis, 2008, 29, 3612-3620.

Shahrokh et al., "Approaches to Analysis of Aggregates and Demonstrating Mass Balance in Pharmaceutical Protein (Basic Fibroblast Growth Factor) Formulations": J. Pharm. Scien., 83:1645-1650, (1994).

Sluzky et al., "Chromatographic Methods for Quantitative Analysis of Native, Denatured, and Aggregated Basic Fibroblast Growth Factor in Solution Formulations": Pharm. Res., 11:485 (1994).

El Walily et al., "Simultaneous determination of tenoxicam and 2-aminopyridine using derivative spectrophotometry and high-performance liquid chromatography": J. Pharm. Bio. Anal., 15:1923-1928 (1997).

Usami et al., "The effect of pH, hydrogen peroxide and temperature on the stability of human monoclonal antibody": J. Pharm. Bio. Anal., 14:1133-1140 (1996).

R. Yang et al., High resolution separation of recombinant monoclonal antibodies by size exclusion ultra-high performance liquid chromatography (SE-UHPLC), Journal of Pharmaceutical and Biomedical Analysis (2015), http://dx.doi.org/10.1016/j.jpba.2015.02.032.

Alexandre Goyon et al., Protocols for the analytical characterization of therapeutic monoclonal antibodies, I—Non-denaturing chromatographic techniques, Journal of Chromatography, 2017, http://dx.doi.org/10.1016/j.chromb.2017.05.010.

Salas-Solano O et al, Robustness of iCIEF methodology for the analysis of monoclonal antibodies: an interlaboratory study, J Sep Sci. 2012; 35(22):3124-9.

Dada OO et al, Characterization of acidic and basic variants of IgG1 therapeutic monoclonal antibodies based on non-denaturing IEF fractionation, Electrophoresis. 2015; 36(21-22):2695-2702.

U.S. Appl. No. 17/621,867, filed Dec. 22, 2021.

Ravi, R.: "Bifunctional immune checkpoint-targeted antibody-ligand traps that simultaneously discble TGFβ enhance the efficacy of cancer immunotherapy": Nature Communications: 2018: vol. 9, No. 741.

Brinkmann et al., "The making of bispecific antibodies", MABS, 2017, vol. 9, No. 2, p. 182-212.

Yao et al. Advances in targeting cell surface signaling molecules for immune modulation, Nat. Rev. Drug Discov., 2013, 12(2):130-146.

International Search Report and Written Opinion of PCT/CN2020/073964, dated Apr. 1, 2020, with translations.

International Search Report and Written Opinion of PCT/CN2020/098140, dated Sep. 15, 2020 with translations.

Rudikoff et al.: "Single amino acid substitution altering antigen-binding specificity": PNAS, vol. 79, No. 6, pp. 1979-1983, 1982.

Tamura et al.: "Structural Correlates of an Anticarcinoma Antibody: Identification of Specificity-Determining Residues (SDRs) and Development of a Minimally Immunogenic Antibody Variant by Retention of SDRs Only": J. Immunol., vol. 164, No. 3, pp. 1432-1441, 2000.

Falconer R., "Advances in liquid formulations of parenteral therapeutic proteins", Biotechnology Advances 37 (2019) 107412.

Wang W., "Instability, stabilization, and formulation of liquid protein pharmaceuticals", International Journal of Pharmaceutics, 185 (1999) 129-188.

* cited by examiner ly, less than or equal to about 50 nM, particularly preferably less than or equal to about 20 nM, more particular preferably less than or equal to about 10 nM, 9 nM, 8 nM, 7 nM, 6 nM, 5 nM, 4 nM, 3 nM, or 2 nM, and most preferably less than or equal to about 1 nM, 0.9 nM, 0.8 nM, or 0.7 nM. In some embodiments, the anti-LAG-3 antibody disclosed herein binds to LAG-3 with a $K_D$ of 0.1-20 nM, preferably 0.5-20 nM, more preferably 0.5-10 nM, 0.5-8 nM, or 0.5-5 nM, and most preferably 0.5-1 nM, 0.5-0.8 nM, 0.5-0.7 nM, or 0.6-0.7 nM. In some embodiments, the LAG-3 is human LAG-3. In some embodiments, the LAG-3 is mouse LAG-3. In some embodiments, the antibody binding affinity is determined using biological optical interferometry (e.g., ForteBio affinity assay).

SEQUENCE LISTING

<160> NUMBER OF SEQ ID NOS: 60

<210> SEQ ID NO 1
<211> LENGTH: 9
<212> TYPE: PRT
<213> ORGANISM: Artificial
<220> FEATURE:
<223> OTHER INFORMATION: synthetic

<400> SEQUENCE: 1

Phe Thr Phe Asp Asp Tyr Ala Met His
1               5

<210> SEQ ID NO 2
<211> LENGTH: 11
<212> TYPE: PRT
<213> ORGANISM: Artificial
<220> FEATURE:
<223> OTHER INFORMATION: synthetic

<400> SEQUENCE: 2

Gly Ser Ile Ser Ser Ser Asp Tyr Tyr Trp Gly
1               5                   10

<210> SEQ ID NO 3
<211> LENGTH: 11
<212> TYPE: PRT
<213> ORGANISM: Artificial
<220> FEATURE:
<223> OTHER INFORMATION: synthetic

<400> SEQUENCE: 3

Gly Ser Ile Ser Ser Pro Asp Tyr Tyr Trp Gly
1               5                   10

<210> SEQ ID NO 4
<211> LENGTH: 11
<212> TYPE: PRT
<213> ORGANISM: Artificial
<220> FEATURE:
<223> OTHER INFORMATION: synthetic

<400> SEQUENCE: 4

Gly Ser Ile Tyr Ser Glu Ser Tyr Tyr Trp Gly
1               5                   10

<210> SEQ ID NO 5
<211> LENGTH: 17
<212> TYPE: PRT
<213> ORGANISM: Artificial
<220> FEATURE:
<223> OTHER INFORMATION: synthetic

<400> SEQUENCE: 5

Gly Ile Ser Trp Asn Ser Gly Asp Ile Gly Tyr Ala Asp Ser Val Lys
1               5                   10                  15

Gly

<210> SEQ ID NO 6
<211> LENGTH: 16
<212> TYPE: PRT
<213> ORGANISM: Artificial
<220> FEATURE:
<223> OTHER INFORMATION: synthetic

<400> SEQUENCE: 6

Ser Ile Tyr Tyr Ser Gly Ser Thr Tyr Tyr Asn Pro Ser Leu Lys Ser
1               5                   10                  15

<210> SEQ ID NO 7
<211> LENGTH: 16
<212> TYPE: PRT
<213> ORGANISM: Artificial
<220> FEATURE:
<223> OTHER INFORMATION: synthetic

<400> SEQUENCE: 7

Ser Ile Val Tyr Ser Gly Tyr Thr Tyr Tyr Asn Pro Ser Leu Lys Ser
1               5                   10                  15

<210> SEQ ID NO 8
<211> LENGTH: 14
<212> TYPE: PRT
<213> ORGANISM: Artificial
<220> FEATURE:
<223> OTHER INFORMATION: synthetic

<400> SEQUENCE: 8

Ala Lys Gly Gly Tyr Asp Gly Ser Tyr Tyr Gly Met Asp Val
1               5                   10

<210> SEQ ID NO 9
<211> LENGTH: 12
<212> TYPE: PRT
<213> ORGANISM: Artificial
<220> FEATURE:
<223> OTHER INFORMATION: synthetic

<400> SEQUENCE: 9

Ala Arg Val Arg Thr Trp Asp Ala Ala Phe Asp Ile
1               5                   10

<210> SEQ ID NO 10
<211> LENGTH: 12
<212> TYPE: PRT
<213> ORGANISM: Artificial
<220> FEATURE:
<223> OTHER INFORMATION: synthetic

<400> SEQUENCE: 10

Ala Arg Val Arg Thr Trp Asp Gln Ser Phe Asp Ile
1               5                   10

<210> SEQ ID NO 11
<211> LENGTH: 11
<212> TYPE: PRT
<213> ORGANISM: Artificial
<220> FEATURE:
<223> OTHER INFORMATION: synthetic

<400> SEQUENCE: 11

Gln Ala Ser Gln Asp Ile Ser Asn Tyr Leu Asn
1               5                   10

<210> SEQ ID NO 12
<211> LENGTH: 11
<212> TYPE: PRT
<213> ORGANISM: Artificial
<220> FEATURE:
<223> OTHER INFORMATION: synthetic

```
<400> SEQUENCE: 12

Gln Ala Gly Gln Asp Ile Ser Asn Tyr Leu Asn
1               5                   10

<210> SEQ ID NO 13
<211> LENGTH: 7
<212> TYPE: PRT
<213> ORGANISM: Artificial
<220> FEATURE:
<223> OTHER INFORMATION: synthetic

<400> SEQUENCE: 13

Asp Ala Ser Asn Leu Glu Thr
1               5

<210> SEQ ID NO 14
<211> LENGTH: 9
<212> TYPE: PRT
<213> ORGANISM: Artificial
<220> FEATURE:
<223> OTHER INFORMATION: synthetic

<400> SEQUENCE: 14

Gln Gln Val Leu Asp Leu Pro Leu Thr
1               5

<210> SEQ ID NO 15
<211> LENGTH: 10
<212> TYPE: PRT
<213> ORGANISM: Artificial
<220> FEATURE:
<223> OTHER INFORMATION: synthetic

<400> SEQUENCE: 15

Gln Gln Val His Ala Leu Pro Pro Trp Thr
1               5                   10

<210> SEQ ID NO 16
<211> LENGTH: 10
<212> TYPE: PRT
<213> ORGANISM: Artificial
<220> FEATURE:
<223> OTHER INFORMATION: synthetic

<400> SEQUENCE: 16

Gln Gln Val Leu Glu Leu Pro Pro Trp Thr
1               5                   10

<210> SEQ ID NO 17
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 17

Gly Ser Ile Xaa Ser Xaa Xaa Tyr Tyr Trp Gly
1               5                   10
```

```
<210> SEQ ID NO 18
<211> LENGTH: 16
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 18

Ser Ile Xaa Tyr Ser Gly Xaa Thr Tyr Tyr Asn Pro Ser Leu Lys Ser
1               5                   10                  15

<210> SEQ ID NO 19
<211> LENGTH: 12
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (8)..(9)
<223> OTHER INFORMATION: Xaa can be any naturally occurring amino acid

<400> SEQUENCE: 19

Ala Arg Val Arg Thr Trp Asp Xaa Xaa Phe Asp Ile
1               5                   10

<210> SEQ ID NO 20
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (3)..(3)
<223> OTHER INFORMATION: Xaa can be any naturally occurring amino acid

<400> SEQUENCE: 20

Gln Ala Xaa Gln Asp Ile Ser Asn Tyr Leu Asn
1               5                   10

<210> SEQ ID NO 21
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (4)..(5)
<223> OTHER INFORMATION: Xaa can be any naturally occurring amino acid

<400> SEQUENCE: 21

Gln Gln Val Xaa Xaa Leu Pro Pro Trp Thr
1               5                   10

<210> SEQ ID NO 22
<211> LENGTH: 121
<212> TYPE: PRT
<213> ORGANISM: Artificial
<220> FEATURE:
<223> OTHER INFORMATION: synthetic
```

```
<400> SEQUENCE: 22

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Asp Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Gly Gly Tyr Asp Gly Ser Tyr Tyr Gly Met Asp Val Trp Gly
            100                 105                 110

Gln Gly Thr Thr Val Thr Val Ser Ser
        115                 120

<210> SEQ ID NO 23
<211> LENGTH: 120
<212> TYPE: PRT
<213> ORGANISM: Artificial
<220> FEATURE:
<223> OTHER INFORMATION: synthetic

<400> SEQUENCE: 23

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Asp Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Val Arg Thr Trp Asp Ala Ala Phe Asp Ile Trp Gly Gln
            100                 105                 110

Gly Thr Met Val Thr Val Ser Ser
        115                 120

<210> SEQ ID NO 24
<211> LENGTH: 120
<212> TYPE: PRT
<213> ORGANISM: Artificial
<220> FEATURE:
<223> OTHER INFORMATION: synthetic

<400> SEQUENCE: 24

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Pro
            20                  25                  30

Asp Tyr Tyr Trp Gly Trp Ile Arg Gln Pro Pro Gly Lys Gly Leu Glu
        35                  40                  45
```

```
Trp Ile Gly Ser Ile Val Tyr Ser Gly Tyr Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Val Arg Thr Trp Asp Gln Ser Phe Asp Ile Trp Gly Gln
                100                 105                 110

Gly Thr Met Val Thr Val Ser Ser
                115                 120

<210> SEQ ID NO 25
<211> LENGTH: 120
<212> TYPE: PRT
<213> ORGANISM: Artificial
<220> FEATURE:
<223> OTHER INFORMATION: synthetic

<400> SEQUENCE: 25

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Tyr Ser Glu
                20                  25                  30

Ser Tyr Tyr Trp Gly Trp Ile Arg Gln Pro Pro Gly Lys Gly Leu Glu
            35                  40                  45

Trp Ile Gly Ser Ile Val Tyr Ser Gly Tyr Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Val Arg Thr Trp Asp Ala Ala Phe Asp Ile Trp Gly Gln
                100                 105                 110

Gly Thr Met Val Thr Val Ser Ser
                115                 120

<210> SEQ ID NO 26
<211> LENGTH: 107
<212> TYPE: PRT
<213> ORGANISM: Artificial
<220> FEATURE:
<223> OTHER INFORMATION: synthetic

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Val Leu Asp Leu Pro Leu
                85                  90                  95

Thr Phe Gly Gly Gly Thr Lys Val Glu Ile Lys
                100                 105
```

<210> SEQ ID NO 27
<211> LENGTH: 108
<212> TYPE: PRT
<213> ORGANISM: Artificial
<220> FEATURE:
<223> OTHER INFORMATION: synthetic

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Val His Ala Leu Pro Pro
                85                  90                  95

Trp Thr Phe Gly Gly Gly Thr Lys Val Glu Ile Lys
            100                 105

<210> SEQ ID NO 28
<211> LENGTH: 108
<212> TYPE: PRT
<213> ORGANISM: Artificial
<220> FEATURE:
<223> OTHER INFORMATION: synthetic

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Gln Ala Gly Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Val Leu Glu Leu Pro Pro
                85                  90                  95

Trp Thr Phe Gly Gly Gly Thr Lys Val Glu Ile Lys
            100                 105

<210> SEQ ID NO 29
<211> LENGTH: 108
<212> TYPE: PRT
<213> ORGANISM: Artificial
<220> FEATURE:
<223> OTHER INFORMATION: synthetic

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

```
Leu Asn Trp Tyr Gln Gln Lys Pro Gly Lys Ala Pro Lys Leu Leu Ile
         35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Val Leu Glu Leu Pro Pro
                 85                  90                  95

Trp Thr Phe Gly Gly Gly Thr Lys Val Glu Ile Lys
                100                 105
```

<210> SEQ ID NO 30
<211> LENGTH: 448
<212> TYPE: PRT
<213> ORGANISM: Artificial
<220> FEATURE:
<223> OTHER INFORMATION: synthetic

<400> SEQUENCE: 30

```
Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
                 20                  25                  30

Ala Met His Trp Val Arg Gln Ala Pro Gly Lys Gly Leu Glu Trp Val
             35                  40                  45

Ser Gly Ile Ser Trp Asn Ser Gly Asp Ile Gly Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Gly Gly Tyr Asp Gly Ser Tyr Tyr Gly Met Asp Val Trp Gly
                100                 105                 110

Gln Gly Thr Thr Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285
```

```
Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445
```

<210> SEQ ID NO 31
<211> LENGTH: 447
<212> TYPE: PRT
<213> ORGANISM: Artificial
<220> FEATURE:
<223> OTHER INFORMATION: synthetic

<400> SEQUENCE: 31

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Asp Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Val Arg Thr Trp Asp Ala Ala Phe Asp Ile Trp Gly Gln
            100                 105                 110

Gly Thr Met Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205
```

```
Pro Ser Asn Thr Lys Val Asp Lys Arg Val Glu Ser Lys Tyr Gly Pro
210                 215                 220

Pro Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 32
<211> LENGTH: 446
<212> TYPE: PRT
<213> ORGANISM: Artificial
<220> FEATURE:
<223> OTHER INFORMATION: synthetic

<400> SEQUENCE: 32

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Pro
            20                  25                  30

Asp Tyr Tyr Trp Gly Trp Ile Arg Gln Pro Pro Gly Lys Gly Leu Glu
        35                  40                  45

Trp Ile Gly Ser Ile Val Tyr Ser Gly Tyr Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Val Arg Thr Trp Asp Gln Ser Phe Asp Ile Trp Gly Gln
            100                 105                 110

Gly Thr Met Val Thr Val Ser Ser Ala Ser Thr Lys Gly Pro Ser Val
        115                 120                 125
```

```
Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445

<210> SEQ ID NO 33
<211> LENGTH: 446
<212> TYPE: PRT
<213> ORGANISM: Artificial
<220> FEATURE:
<223> OTHER INFORMATION: synthetic

<400> SEQUENCE: 33

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Tyr Ser Glu
            20                  25                  30

Ser Tyr Tyr Trp Gly Trp Ile Arg Gln Pro Pro Gly Lys Gly Leu Glu
        35                  40                  45
```

```
Trp Ile Gly Ser Ile Val Tyr Ser Gly Tyr Thr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Val Arg Thr Trp Asp Ala Ala Phe Asp Ile Trp Gly Gln
                100                 105                 110

Gly Thr Met Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
            435                 440                 445

<210> SEQ ID NO 34
<211> LENGTH: 214
<212> TYPE: PRT
```

<213> ORGANISM: Artificial
<220> FEATURE:
<223> OTHER INFORMATION: synthetic

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Val Leu Asp Leu Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 35
<211> LENGTH: 215
<212> TYPE: PRT
<213> ORGANISM: Artificial
<220> FEATURE:
<223> OTHER INFORMATION: synthetic

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Val His Ala Leu Pro Pro
                85                  90                  95

Trp Thr Phe Gly Gly Gly Thr Lys Val Glu Ile Lys Arg Thr Val Ala
            100                 105                 110

Ala Pro Ser Val Phe Ile Phe Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 36
<211> LENGTH: 215
<212> TYPE: PRT
<213> ORGANISM: Artificial
<220> FEATURE:
<223> OTHER INFORMATION: synthetic

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Gln Ala Gly Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Val Leu Glu Leu Pro Pro
                85                  90                  95

Trp Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 37
<211> LENGTH: 215
<212> TYPE: PRT
<213> ORGANISM: Artificial
<220> FEATURE:

<223> OTHER INFORMATION: synthetic

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Val Leu Glu Leu Pro Pro
                85                  90                  95

Trp Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 38
<211> LENGTH: 363
<212> TYPE: DNA
<213> ORGANISM: Artificial
<220> FEATURE:
<223> OTHER INFORMATION: synthetic

<400> SEQUENCE: 38
gaggtgcagc tggtggagag cggaggcgga ctggtgcagc ctggcagaag cctgagactg      60
agctgtgccg ccagcggctt caccttcgac gactacgcca tgcactgggt gagacaggcc     120
cctggcaaag gcctggagtg ggtgagcggc atcagctgga atagcggcga catcggctac     180
gccgacagcg tgaagggcag gttcaccatc agcagggaca acgccaagaa cagcctgtac     240
ctgcagatga actccctgag ggccgaggac accgccctgt actactgcgc caagggcggc     300
tacgacggca gctactacgg catggacgtg tggggccagg gcaccaccgt gacagtgagc     360
agc                                                                   363

<210> SEQ ID NO 39
<211> LENGTH: 360
<212> TYPE: DNA
<213> ORGANISM: Artificial
<220> FEATURE:
<223> OTHER INFORMATION: synthetic

<400> SEQUENCE: 39

```
cagctgcagc tgcaggagag cggacctggc ctggtgaagc ccagcgagac cctgagcctg      60
acctgcacag tgtccggcgg cagcatcagc agcagcgact actactgggg ctggatcaga     120
cagcccccg gaaagggcct ggagtggatc ggcagcatct actacagcgg cagcacctac     180
tacaacccca gcctgaagag cagggtgacc atcagcgtgg acaccagcaa gaaccagttc     240
agcctgaagc tgagcagcgt gacagccgcc gacacagccg tgtactactg cgccagagtg     300
aggacctggg acgccgcctt cgacatctgg ggacagggca ccatggtgac agtgagcagc     360
```

<210> SEQ ID NO 40
<211> LENGTH: 360
<212> TYPE: DNA
<213> ORGANISM: Artificial
<220> FEATURE:
<223> OTHER INFORMATION: synthetic

<400> SEQUENCE: 40

```
cagctgcagc tgcaggaaag cggaccagga ctggtgaaac ctagcgagac cctgagcctg      60
acctgtacag tgtccggagg cagcatcagc tcccccgact actattgggg ttggatccgg     120
cagccaccag gaaagggcct ggagtggatt ggcagcatcg tgtacagcgg ctacacctac     180
tacaacccca gcctgaagag ccgcgtgaca atcagcgtgg acaccagcaa gaaccagttc     240
agcctgaagc tgtcttcagt gacagccgcc gacaccgcag tgtactattg cgccagggtg     300
cggacttggg accagagctt cgacatttgg gggcagggca ccatggtgac agtgagcagc     360
```

<210> SEQ ID NO 41
<211> LENGTH: 360
<212> TYPE: DNA
<213> ORGANISM: Artificial
<220> FEATURE:
<223> OTHER INFORMATION: synthetic

<400> SEQUENCE: 41

```
cagctgcagc tgcaggaatc aggaccagga ctggtgaagc ctagcgagac actgagcctg      60
acctgtaccg tgtccggagg cagcatctac agcgagagct actattgggg ttggatccgg     120
cagccaccag gaaagggcct ggagtggatt ggcagcatcg tgtacagcgg ctacacctac     180
tacaacccca gcctgaagag ccgcgtgaca atcagcgtgg acaccagcaa gaaccagttc     240
agcctgaagc tgtcttcagt gacagccgcc gacaccgcag tgtactattg cgccagggtg     300
cggacttggg acgccgcctt tgacatttgg ggccagggca caatggtgac agtgagcagc     360
```

<210> SEQ ID NO 42
<211> LENGTH: 321
<212> TYPE: DNA
<213> ORGANISM: Artificial
<220> FEATURE:
<223> OTHER INFORMATION: synthetic

<400> SEQUENCE: 42

```
gacatccaga tgacccagag ccctagcagc ctgagcgcca gcgtgggcga tagggtgacc      60
atcacctgcc aggccagcca ggacatcagc aactacctga actggtacca gcagaagccc     120
ggcaaggccc ccaagctgct gatctacgac gccagcaacc tggagaccgg cgtgcctagc     180
```

```
agatttagcg gcagcggcag cggcacagac ttcaccttca ccatcagcag cctgcagccc      240
gaggacatcg ccacctacta ctgccagcag gtgctggacc tgcccctgac ctttggcggc      300
ggcaccaagg tggagatcaa g                                                321

<210> SEQ ID NO 43
<211> LENGTH: 324
<212> TYPE: DNA
<213> ORGANISM: Artificial
<220> FEATURE:
<223> OTHER INFORMATION: synthetic

<400> SEQUENCE: 43
gacatccaga tgacccagag ccctagcagc ctgagcgcca gcgtgggcga tagggtgacc       60
atcacctgcc aggccagcca ggacatcagc aactacctga actggtacca gcagaagccc      120
ggcaaggccc ccaagctgct gatctacgac gccagcaacc tggagaccgg cgtgcctagc      180
agatttagcg gcagcggcag cggcacagac ttcaccttca ccatcagcag cctgcagccc      240
gaggacatcg ccacctacta ctgccagcag gtgcacgccc tgcctccctg gacctttggc      300
ggcggcacca aggtggagat caag                                             324

<210> SEQ ID NO 44
<211> LENGTH: 324
<212> TYPE: DNA
<213> ORGANISM: Artificial
<220> FEATURE:
<223> OTHER INFORMATION: synthetic

<400> SEQUENCE: 44
gacatccaga tgacccagag ccctagcagc ctgagcgcta gcgtgggaga tagagtgacc       60
atcacttgcc aggccggcca ggacatcagc aactacctga attggtacca gcagaagccc      120
ggcaaggccc ctaagctgct gatctacgac gcctctaatc tggagaccgg cgtgcctagc      180
agattcagcg gaagcggcag cggcacagat ttcaccttca ccatcagcag cctgcagccc      240
gaggacatcg ccacctacta ttgccagcag gtgctggagc tgcctccttg gacattcgga      300
ggaggaacaa aggtggagat caag                                             324

<210> SEQ ID NO 45
<211> LENGTH: 324
<212> TYPE: DNA
<213> ORGANISM: Artificial
<220> FEATURE:
<223> OTHER INFORMATION: synthetic

<400> SEQUENCE: 45
gacatccaga tgacccagag ccctagcagc ctgagcgcta gcgtgggaga tagagtgacc       60
atcacttgcc aggccagcca ggacatcagc aactacctga attggtacca gcagaagccc      120
ggcaaggccc ctaagctgct gatctacgac gcctctaatc tggagaccgg cgtgcctagc      180
agattcagcg gaagcggcag cggcacagat ttcaccttca ccatcagcag cctgcagccc      240
gaggacatcg ccacctacta ttgccagcag gtgctggagc tgcctccttg gacattcgga      300
ggaggaacaa aggtggagat caag                                             324

<210> SEQ ID NO 46
<211> LENGTH: 327
<212> TYPE: PRT
<213> ORGANISM: Artificial
<220> FEATURE:
```

<223> OTHER INFORMATION: synthetic

<400> SEQUENCE: 46

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Ala Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 47
<211> LENGTH: 107
<212> TYPE: PRT
<213> ORGANISM: Artificial
<220> FEATURE:
<223> OTHER INFORMATION: synthetic

<400> SEQUENCE: 47

```
Arg Thr Val Ala Ala Pro Ser Val Phe Ile Phe Pro Pro Ser Asp Glu
1               5                   10                  15
```

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 48
<211> LENGTH: 20
<212> TYPE: PRT
<213> ORGANISM: Artificial
<220> FEATURE:
<223> OTHER INFORMATION: synthetic

<400> SEQUENCE: 48

Met Glu Thr Asp Thr Leu Leu Leu Trp Val Leu Leu Leu Trp Val Pro
1               5                   10                  15

Gly Ser Thr Gly
            20

<210> SEQ ID NO 49
<211> LENGTH: 801
<212> TYPE: DNA
<213> ORGANISM: Artificial
<220> FEATURE:
<223> OTHER INFORMATION: synthetic

<400> SEQUENCE: 49
atggtgtgtc tgaagctccc tggaggctcc tgcatgacag cgctgacagt gacactgatg      60
gtgctgagct ccccactggc tttgtctggg acacccgac cacgtttcct gtggcagcct      120
aagagggagt gtcatttctt caatgggacg gagcgggtgc ggttcctgga cagatacttc     180
tataaccagg aggagtccgt gcgcttcgac agcgacgtgg gggagttccg ggcggtgacg     240
gagctggggc ggcctgacgc tgagtactgg aacagccaga aggacatcct ggagcaggcg     300
cgggccgcgg tggacaccta ctgcagacac aactacgggg ttgtggagag cttcacagtg     360
cagcggcgag tccaacctaa ggtgactgta tatccttcaa agacccagcc cctgcagcac     420
cacaacctcc tggtctgctc tgtgagtggt ttctatccag cagcattga agtcaggtgg     480
ttcctgaacg gccaggaaga gaaggctggg atggtgtcca ggcctgat ccagaatgga     540
gactggacct tccagaccct ggtgatgctg gaaacagttc ctcgaagtgg agaggtttac     600
acctgccaag tggagcaccc aagcgtgaca agccctctca cagtggaatg agagcacgg     660
tctgaatctg cacagagcaa gatgctgagt ggagtcgggg ctttgtgct gggcctgctc     720
ttccttgggg ccgggctgtt catctacttc aggaatcaga aggacactc tggacttcag     780
ccaacaggat tcctgagctg a                                               801

<210> SEQ ID NO 50
<211> LENGTH: 765
<212> TYPE: DNA
<213> ORGANISM: Artificial
<220> FEATURE:

-continued

<223> OTHER INFORMATION: synthetic

<400> SEQUENCE: 50

```
atggccataa gtggagtccc tgtgctagga ttttcatca tagctgtgct gatgagcgct    60
caggaatcat gggctatcaa agaagaacat gtgatcatcc aggccgagtt ctatctgaat   120
cctgaccaat caggcgagtt tatgtttgac tttgatggtg atgagatttt ccatgtggat   180
atggcaaaga aggagacggt ctggcggctt gaagaatttg gacgatttgc cagctttgag   240
gctcaaggtg cattggccaa catagctgtg acaaagcca acctggaaat catgacaaag   300
cgctccaact atactccgat caccaatgta cctccagagg taactgtgct cacaaacagc   360
cctgtggaac tgagagagcc caacgtcctc atctgtttca tagacaagtt caccccacca   420
gtggtcaatg tcacgtggct tcgaaatgga aaacctgtca ccacaggagt gtcagagaca   480
gtcttcctgc ccagggaaga ccaccttttc cgcaagttcc actatctccc cttcctgccc   540
tcaactgagg acgtttacga ctgcagggtg gagcactggg gcttggatga gcctcttctc   600
aagcactggg agtttgatgc tccaagccct ctcccagaga ctacagagaa cgtggtgtgt   660
gccctgggcc tgactgtggg tctggtgggc atcattattg ggaccatctt catcatcaag   720
ggattgcgca aaagcaatgc agcagaacgc agggggcctc tgtaa              765
```

<210> SEQ ID NO 51
<211> LENGTH: 7
<212> TYPE: PRT
<213> ORGANISM: Artificial
<220> FEATURE:
<223> OTHER INFORMATION: synthetic

<400> SEQUENCE: 51

Gly Phe Asn Ile Glu Asp Thr
1               5

<210> SEQ ID NO 52
<211> LENGTH: 6
<212> TYPE: PRT
<213> ORGANISM: Artificial
<220> FEATURE:
<223> OTHER INFORMATION: synthetic

<400> SEQUENCE: 52

Asp Pro Ala Asn Asp Asp
1               5

<210> SEQ ID NO 53
<211> LENGTH: 8
<212> TYPE: PRT
<213> ORGANISM: Artificial
<220> FEATURE:
<223> OTHER INFORMATION: synthetic

<400> SEQUENCE: 53

Gly Leu Gly Arg Trp Phe Ala Tyr
1               5

<210> SEQ ID NO 54
<211> LENGTH: 11
<212> TYPE: PRT
<213> ORGANISM: Artificial
<220> FEATURE:
<223> OTHER INFORMATION: synthetic

<400> SEQUENCE: 54

Lys Ala Ser Gln Asp Val Ile Asn Ala Val Ala
1               5                   10

<210> SEQ ID NO 55
<211> LENGTH: 7
<212> TYPE: PRT
<213> ORGANISM: Artificial
<220> FEATURE:
<223> OTHER INFORMATION: synthetic

<400> SEQUENCE: 55

Ser Ala Ser Asn Arg Tyr Thr
1               5

<210> SEQ ID NO 56
<211> LENGTH: 9
<212> TYPE: PRT
<213> ORGANISM: Artificial
<220> FEATURE:
<223> OTHER INFORMATION: synthetic

<400> SEQUENCE: 56

Gln Gln His Tyr Ser Pro Pro Leu Thr
1               5

<210> SEQ ID NO 57
<211> LENGTH: 117
<212> TYPE: PRT
<213> ORGANISM: Artificial
<220> FEATURE:
<223> OTHER INFORMATION: synthetic

<400> SEQUENCE: 57

Glu Val Gln Leu Val Gln Ser Gly Ala Glu Val Lys Lys Pro Gly Ala
1               5                   10                  15

Thr Val Lys Ile Ser Cys Thr Ala Ser Gly Phe Asn Ile Glu Asp Thr
            20                  25                  30

Tyr Ile His Trp Val Gln Gln Ala Pro Gly Gln Gly Leu Glu Trp Ile
        35                  40                  45

Gly Arg Ile Asp Pro Ala Asn Asp Asp Thr Lys Tyr Ala Pro Lys Phe
    50                  55                  60

Gln Gly Arg Ala Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Gly Arg Gly Leu Gly Arg Trp Phe Ala Tyr Trp Gly Gln Gly Thr Leu
            100                 105                 110

Val Thr Val Ser Ser
        115

<210> SEQ ID NO 58
<211> LENGTH: 107
<212> TYPE: PRT
<213> ORGANISM: Artificial
<220> FEATURE:
<223> OTHER INFORMATION: synthetic

<400> SEQUENCE: 58

Gly Ile Val Met Thr Gln Ser Pro Asp Ser Leu Ala Val Ser Leu Gly
1               5                   10                  15

```
Glu Arg Ala Thr Ile Asn Cys Lys Ala Ser Gln Asp Val Ile Asn Ala
                20                  25                  30

Val Ala Trp Tyr Gln Gln Lys Pro Gly Gln Ser Pro Lys Leu Leu Ile
            35                  40                  45

Tyr Ser Ala Ser Asn Arg Tyr Thr Gly Val Pro Asp Arg Phe Ser Gly
        50                  55                  60

Ser Gly Ser Gly Thr Asp Phe Thr Leu Thr Ile Ser Ser Leu Gln Ala
65                  70                  75                  80

Glu Asp Leu Ala Val Tyr Tyr Cys Gln Gln His Tyr Ser Pro Pro Leu
                85                  90                  95

Thr Phe Gly Gly Gly Thr Lys Val Glu Ile Lys
            100                 105
```

<210> SEQ ID NO 59
<211> LENGTH: 447
<212> TYPE: PRT
<213> ORGANISM: Artificial
<220> FEATURE:
<223> OTHER INFORMATION: synthetic

<400> SEQUENCE: 59

```
Glu Val Gln Leu Val Gln Ser Gly Ala Glu Val Lys Lys Pro Gly Ala
1               5                   10                  15

Thr Val Lys Ile Ser Cys Thr Ala Ser Gly Phe Asn Ile Glu Asp Thr
                20                  25                  30

Tyr Ile His Trp Val Gln Gln Ala Pro Gly Gln Gly Leu Glu Trp Ile
            35                  40                  45

Gly Arg Ile Asp Pro Ala Asn Asp Asp Thr Lys Tyr Ala Pro Lys Phe
        50                  55                  60

Gln Gly Arg Ala Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Gly Arg Gly Leu Gly Arg Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270
```

```
Val Lys Phe Asn Trp Tyr Val Asp Gly Val Glu Val His Asn Ala Lys
            275                 280                 285
Thr Lys Pro Arg Glu Glu Gln Tyr Ala Ser Thr Tyr Arg Val Val Ser
290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
            435                 440                 445

<210> SEQ ID NO 60
<211> LENGTH: 214
<212> TYPE: PRT
<213> ORGANISM: Artificial
<220> FEATURE:
<223> OTHER INFORMATION: synthetic

<400> SEQUENCE: 60

Gly Ile Val Met Thr Gln Ser Pro Asp Ser Leu Ala Val Ser Leu Gly
1               5                   10                  15
Glu Arg Ala Thr Ile Asn Cys Lys Ala Ser Gln Asp Val Ile Asn Ala
            20                  25                  30
Val Ala Trp Tyr Gln Gln Lys Pro Gly Gln Ser Pro Lys Leu Leu Ile
        35                  40                  45
Tyr Ser Ala Ser Asn Arg Tyr Thr Gly Val Pro Asp Arg Phe Ser Gly
    50                  55                  60
Ser Gly Ser Gly Thr Asp Phe Thr Leu Thr Ile Ser Ser Leu Gln Ala
65                  70                  75                  80
Glu Asp Leu Ala Val Tyr Tyr Cys Gln Gln His Tyr Ser Pro Pro Leu
                85                  90                  95
Thr Phe Gly Gly Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
    195                 200                 205

Phe Asn Arg Gly Glu Cys
    210
```

ANTI-LAG-3 ANTIBODY AND USE THEREOF

The present invention relates to a novel antibody specifically binding to LAG-3, an antibody fragment thereof, and a composition comprising the antibody or the antibody fragment. In addition, the present invention relates to a nucleic acid encoding the antibody or the antibody fragment thereof, a host cell comprising the nucleic acid, and related use. Furthermore, the present invention relates to therapeutic and diagnostic use of the antibody and antibody fragment. In particular, the present invention relates to a combination therapy of these antibodies and antibody fragments with other therapies, e.g., therapeutic modalities or therapeutic agents, such as anti-PD-1 or anti-PD-L1 antibodies.

BACKGROUND

Lymphocyte-activation gene 3 (LAG-3), also known as CD223, is a type I transmembrane protein encoded by a LAG3 gene in the human body. The molecular properties and biological functions of LAG-3 have been well characterized and described, see, e.g., Sierro et al., Expert Opin Ther Targets (2011) 15 (1): 91-101. LAG-3 is a CD4-like protein expressed on the surface of T cells (particularly activated T cells), natural killer cells, B cells, and plasmacytoid dendritic cells. LAG-3 has been shown to be a negative co-stimulatory receptor, i.e., an inhibitory receptor.

LAG-3 binds to MHC class II molecules (Baixeras et al. (1992) J. Exp. Med. 176: 327-337; Huard et al. (1996) Eur. J. Immunol, 26: 1180-1186) that are a family of molecules constitutively expressing at high level on the surface of antigen-presenting cells (APCs), such as dendritic cells, macrophages and B cells. Functions of LAG-3 depend on its binding to MHC class II molecules and the signal transduction through its cytoplasmic domain. It has been proposed that the direct binding of LAG-3 to MHC class II molecules plays a role in down-regulating the antigen-dependent stimulation of CD4+ T lymphocytes (Huard et al. (1994) Eur. J. Immunol. 24: 3216-3221). The interaction between LAG3 and MHC class II molecules was also thought to play a role in regulating the function of dendritic cells (Andreae et al. J Immunol 168: 3874-3880, 2002). Recent preclinical studies have also documented the role of LAG-3 in CD8 T-cell exhaustion (Blackburn et al. Nat Immunol 10: 29-37, 2009).

Studies have shown that exhausted CD8+ T cells following a chronic viral infection express multiple inhibitory receptors (e.g., PD-1, CD160, and 2B4). LAG-3 is expressed at a high level following LCMV infection, and blockade of the PD-1/PD-L1 pathway and blockade of LAG-3 has been shown to significantly reduce viral load in chronically infected mice (Blackburn et al., Nat Immunol (2009) 10: 29-37). It has also shown that combined inhibition of the PD-1/PD-L1 pathway and LAG-3 blockade provides anti-tumor efficacy (Jing et al., Journal for ImmunoTherapy of Cancer (2015)3: 2).

In view of the above-mentioned important roles of LAG-3, there is a need to develop new anti-LAG-3 antibodies, particularly humanized or human antibodies, to modulate LAG-3 activity. Such antibodies can be better used for treating tumors and other diseases such as infections. It would also be desirable to have new anti-LAG-3 antibodies that can be used in combination with other therapies (e.g., therapeutic agents, such as anti-PD-1 or anti-PD-L1 antibodies) for treating tumors, particularly metastatic or refractory tumors, or for treating infections, such as chronic infections. Furthermore, there is a need for anti-mouse LAG-3 antibodies that can be used in mouse models to facilitate the study of the in-vivo biological activities of the antibodies.

SUMMARY

Disclosed herein is an antibody molecule binding to LAG-3, such as a fully human or humanized antibody molecule. A nucleic acid encoding the antibody or an antibody fragment thereof, and an expression vector, a host cell and a method for producing the antibody molecule are also provided. In addition, an immunoconjugate, a multi-specific or bispecific antibody molecule, and a pharmaceutical composition that comprise the anti-LAG-3 antibody molecule are provided. The anti-LAG-3 antibody molecule disclosed herein can be used to treat, prevent, and/or diagnose neoplastic diseases and infectious diseases, either alone or in combination with other therapies, such as therapeutic agents (e.g., anti-PD-1 antibodies or anti-PD-L1 antibodies) or therapeutic modalities. Furthermore, disclosed herein are a composition and method for detecting LAG-3 and a method for treating a variety of diseases (including tumors and/or infectious diseases) with the anti-LAG-3 antibody molecule.

Therefore, in some embodiments, the antibody disclosed herein or a fragment thereof (specifically) binds to LAG-3. In some embodiments, the antibody disclosed herein or a fragment thereof (specifically) binds to human LAG-3 or mouse LAG-3.

In some embodiments, the anti-LAG-3 antibody disclosed herein or a fragment thereof binds to LAG-3 (e.g., human LAG-3) with high affinity, e.g., with an equilibrium dissociation constant ($K_D$) of less than about 100 nM, preferab- In some embodiments, the antibody disclosed herein or a fragment thereof binds to cells expressing human LAG-3, e.g., with an $EC_{50}$ of less than or equal to about 3.3 nM, 3 nM, 2 nM, 1.5 nM, 1.4 nM, 1.3 nM, 1.2 nM, 1.1 nM, 1 nM, 0.9 nM, 0.8 nM, 0.7 nM, 0.6 nM, or 0.5 nM. In some embodiments, the binding is determined using flow cytometry (e.g., FACS). In some embodiments, the cells expressing human LAG-3 are 293 cells (e.g., HEK293 cells) expressing human LAG-3.

In some embodiments, the antibody disclosed herein or a fragment thereof binds to cells expressing mouse LAG-3, e.g., with an $EC_{50}$ of less than or equal to about 15,000 nM, 14,000 nM, or 13,000 nM. In some embodiments, the antibody or fragment thereof of the invention binds to cells expressing mouse LAG-3, e.g., with an $EC_{50}$ of less than or equal to about 50 nM, e.g., an $EC_{50}$ of about 40 to 50 nM, about 40 to 45 nM, or about 42 nM. In some embodiments, the binding is determined using flow cytometry (e.g., FACS). In some embodiments, the cells expressing mouse LAG-3 are Chinese hamster ovary (CHO) cells expressing mouse LAG-3.

In some embodiments, the antibody disclosed herein or a fragment thereof inhibits the relevant activity of LAG-3, e.g., with an $IC_{50}$ of less than or equal to about 20 nM, 10 nM, 9 nM, 8 nM, 7 nM, 6 nM, or 5 nM, and preferably of about 1 to 6 nM, 1 to 5 nM, 4 nM, 4.5 nM, 5 nM, 5.1 nM, 5.2 nM, 5.3 nM, 5.4 nM, 5.5 nM, 5.6 nM, 5.7 nM, 5.8 nM, 5.9 nM, or 6 nM. In some embodiments, the relevant activity of LAG-3 refers to the binding of MHC class II molecules to LAG-3. In some embodiments, the antibody disclosed herein or a fragment thereof inhibits the binding of LAG-3 to MHC class II molecules on cells expressing the MHC class II molecules, with an $IC_{50}$ of less than or equal to about 20 nM, 10 nM, 9 nM, 8 nM, 7 nM, 6 nM, or 5 nM, and preferably of about 1 to 6 nM, 1 to 5 nM, 4 nM, 4.5 nM, 5 nM, 5.1 nM, 5.2 nM, 5.3 nM, 5.4 nM, 5.5 nM, 5.6 nM, 5.7 nM, 5.8 nM, 5.9 nM, or 6 nM. In some embodiments, the MHC class II molecules are HLA-DR. In some embodiments, the cells are CHO cells. In some embodiments, the inhibition on the relevant activity of LAG-3 by the antibody disclosed herein or a fragment thereof is measured using flow cytometry (e.g., FACS).

In some embodiments, the antibody disclosed herein or a fragment thereof binds to endogenous LAG-3 on the surface of activated CD4+ and/or CD8+ T cells, e.g., with an $EC_{50}$ of less than or equal to about 35 pM, 30 pM, 25 pM, 20 pM, 15 pM, 14 pM, or 13 pM, and preferably of about 1 to 20 pM, 5 to 20 pM, 5 to 15 pM, 10 to 15 pM, 11 to 13 pM, 10 pM, 11 pM, 12 pM, or 13 pM. In some embodiments, the activated CD4+ T cells are activated human CD4+ T cells. In some embodiments, the binding is determined by flow cytometry (e.g., FACS). In some embodiments, flow cytometry is performed in an Accuri C6 system.

In some embodiments, the antibody disclosed herein or a fragment thereof inhibits one or more activities of LAG-3, e.g., resulting in one or more of the following: increased antigen-dependent stimulation of CD4+ T lymphocytes; increased T cell proliferation; increased expression of activating antigens (e.g., CD25); increased expression of cytokines (e.g., interferons, interleukin-2 (IL-2), or interleukin-4 (IL-4)); increased expression of chemokines (e.g., CCL3, CCL4, or CCL5); a decrease in the suppressive activity of Treg cells; increased T-cell homeostasis; an increase in tumor-infiltrating lymphocytes; or a decrease in immune evasion by cancer cells.

In some embodiments, the anti-LAG-3 antibody disclosed herein or a fragment thereof can induce the antibody-dependent cell-mediated cytotoxicity (ADCC).

In some embodiments, the anti-LAG-3 antibody disclosed herein can effectively treat tumors (e.g., cancer) or infectious diseases (e.g., a chronic infection), either alone or in combination with other therapies (e.g., therapeutic modalities and/or therapeutic agents). Preferably, the anti-LAG-3 antibody disclosed herein can treat tumor, particularly metastatic or refractory tumor, in combination with an anti-PD-1 or anti-PD-L1 antibody. In some embodiments, the tumor is cancer. In some embodiments, the tumor is gastrointestinal neoplasms. In some embodiments, the cancer is colon cancer.

In some embodiments, a heavy chain and/or light chain of the anti-LAG-3 antibody disclosed herein or a fragment thereof further comprises a signal peptide sequence, such as METDTLLLWVLLLWVPGSTG (SEQ ID NO: 48).

In some embodiments, the antibody disclosed herein also comprises a variant of the amino acid sequence of the anti-LAG-3 antibody, and an antibody that binds to the same epitope as any of the anti-LAG-3 antibodies described above or a fragment thereof.

In certain embodiments, an antibody or an antibody fragment (preferably an antigen-binding fragment) that binds to LAG-3 or a fragment thereof is provided, wherein the antibody or the antibody fragment binds to an epitope within LAG-3.

In some embodiments, the anti-LAG-3 antibody disclosed herein is of an IgG1, IgG2, IgG3, IgG4, IgM, IgA1, IgA2, IgD, or IgE type. In some embodiments, the anti-LAG-3 antibody disclosed herein comprises a heavy chain constant region selected from heavy chain constant regions of, e.g., IgG1, IgG2, IgG3, IgG4, IgM, IgA1, IgA2, IgD, and IgE, particularly from heavy chain constant regions of, e.g. IgG1, IgG2, IgG3 and IgG4, and more particularly from heavy chain constant regions of IgG1, IgG2 and IgG4, e.g. human IgG1, IgG2 and IgG4. In one embodiment, the heavy chain constant region is a heavy chain constant region of human IgG1 or human IgG4. In one embodiment, the heavy chain constant region is a heavy chain constant region of human IgG4. In another embodiment, the anti-LAG-3 antibody molecule has, e.g., a kappa or lambda light chain constant region, and preferably a kappa (e.g., human kappa) light chain constant region.

In yet another embodiment, the anti-LAG-3 antibody molecule comprises a heavy chain constant region of IgG4 (e.g., human IgG4). In one embodiment, the human IgG4 comprises a substitution at position 228 according to EU numbering (e.g., a substitution of Ser to Pro). In yet another embodiment, the human IgG4 contains a mutation to AA at positions 114 to 115 (EU numbering) (Armour KL1, Clark M R, Hadley A G, Williamson L M, Eur J Immunol., August, 1999; 29(8): 2613-24, Recombinant human IgG molecules lacking Fcgamma receptor I binding and monocyte triggering activities). In one embodiment, the heavy chain constant region comprises or consists of an amino acid sequence shown as SEQ ID NO: 46, or a sequence having at least 80%, 85%, 90%, 91%, 92%, 93%, 94%, 95%, 96%, 97%, 98%, 99% or more identity therewith.

In another embodiment, the anti-LAG-3 antibody molecule comprises a kappa light chain constant region, e.g., a human kappa light chain constant region. In one embodiment, the light chain constant region comprises or consists of an amino acid sequence shown as SEQ ID NO: 47, or a sequence having at least 80%, 85%, 90%, 91%, 92%, 93%, 94%, 95%, 96%, 97%, 98%, 99% or more identity therewith.

In another embodiment, the anti-LAG-3 antibody molecule comprises a heavy chain constant region of IgG4 (e.g., a heavy chain constant region of human IgG4) and a kappa light chain constant region (e.g., a human kappa light chain constant region). In one embodiment, the constant region is a constant region of mutated IgG4, e.g., mutated human IgG4 (e.g., having a mutation at position 228 according to EU numbering, such as S228P mutation). In some embodiments, the heavy chain constant region of human IgG4 comprises or consists of an amino acid sequence shown as SEQ ID NO: 46, or a sequence having at least 80%, 85%, 90%, 91%, 92%, 93%, 94%, 95%, 96%, 97%, 98%, 99% or more identity therewith. In one embodiment, the human kappa light chain constant region comprises or consists of an amino acid sequence shown as SEQ ID NO: 47, or a sequence having at least 80%, 85%, 90%, 91%, 92%, 93%, 94%, 95%, 96%, 97%, 98%, 99% or more identity therewith.

In one embodiment, the anti-LAG-3 antibody molecule is isolated or recombinant.

In some embodiments, the anti-LAG-3 antibody is a monoclonal antibody or a monospecific antibody. The anti-LAG-3 antibody molecule can also be a humanized, chimeric, camelid, shark or in-vitro generated antibody molecule. In some embodiments, the anti-LAG-3 antibody is humanized. In some embodiments, the anti-LAG-3 antibody is a human antibody. In some embodiments, at least a portion of the framework sequence of the anti-LAG-3 antibody is a human consensus framework sequence. In one embodiment, the anti-LAG-3 antibody of the invention also comprises an antibody fragment thereof, and preferably an antibody fragment selected from: Fab, Fab', Fab'-SH, Fv, a single-chain variable fragment (e.g., scFv) or (Fab')$_2$, a single-domain antibody, a diabody (dAb), and a linear antibody.

In some embodiments, the anti-LAG-3 antibody molecule is in the form of a bispecific or multispecific antibody molecule. In one embodiment, the bispecific antibody molecule has a first binding specificity for LAG-3 and a second binding specificity for PD-1, TIM-3, CEACAM (e.g., CEACAM-1 and/or CEACAM-5), PD-L1, or PD-L2. In one embodiment, the bispecific antibody molecule binds to LAG-3 and PD-1. In one embodiment, the bispecific antibody molecule binds to LAG-3 and PD-L1. In yet another embodiment, the bispecific antibody molecule binds to LAG-3 and PD-L2. Any combination of the foregoing molecules can be produced in a multispecific antibody molecule. The multispecific antibody molecule, such as a trispecific antibody molecule, comprises a first binding specificity for LAG-3 and a second and third binding specificities for one or more molecules of PD-1, TIM-3, CEACAM (e.g., CEACAM-1 or CEACAM-5), PD-L1, or PD-L2.

In other embodiments, the anti-LAG-3 antibody molecule is used in combination with a bispecific molecule comprising one or more of PD-1, TIM-3, CEACAM (e.g., CEACAM-1 or CEACAM-5), PD-L1 or PD-L2.

In one aspect, the present invention provides a nucleic acid encoding any of the above anti-LAG-3 antibodies or a fragment thereof. In one embodiment, a vector comprising the nucleic acid is provided. In one embodiment, the vector is an expression vector. In one embodiment, a host cell comprising the nucleic acid or the vector is provided. In one embodiment, the host cell is eukaryotic. In another embodiment, the host cell is selected from a yeast cell, a mammal cell (e.g., CHO cell or 293 cell), and other cells suitable for preparing an antibody or an antigen-binding fragment thereof. In another embodiment, the host cell is prokaryotic, such as an *E. coli* cell.

In one embodiment, the present invention provides a method for preparing an anti-LAG-3 antibody or a fragment thereof (preferably, an antigen-binding fragment), wherein the method comprises culturing a host cell under conditions suitable for the expression of a nucleic acid encoding the antibody or the fragment thereof (preferably, the antigen-binding fragment), and optionally isolating the antibody or the fragment thereof (preferably, the antigen-binding fragment). In a certain embodiment, the method further comprises isolating the anti-LAG-3 antibody or the fragment thereof (preferably the antigen-binding fragment) from the host cell.

In some embodiments, the invention provides an immunoconjugate comprising any of the anti-LAG-3 antibodies provided herein and other substances, such as a cytotoxic agent or a marker. In some embodiments, the immunoconjugate is used to prevent or treat a tumor (e.g., cancer) or an infectious disease. Preferably, the tumor is gastrointestinal neoplasms (e.g., cancer), such as colon cancer. Preferably, the infectious disease is a chronic infection.

In some embodiments, the present invention provides a composition comprising any of the anti-LAG-3 antibodies described herein or a fragment thereof (preferably a antigen-binding fragment thereof), or an immunoconjugate thereof, wherein, preferably, the composition is a pharmaceutical composition. In one embodiment, the composition further comprises pharmaceutical adjuvants. In one embodiment, the composition, such as a pharmaceutical composition, comprises the anti-LAG-3 antibody disclosed herein or a fragment thereof or an immunoconjugate thereof, and a combination of one or more other therapeutic agents (e.g., a chemotherapeutic agent, a cytotoxic agent, a vaccine, other antibodies, an anti-infective active agent, or an immunomodulatory agent (such as an activator of a co-stimulatory molecule or an inhibitor of an immune checkpoint molecule), and preferably an anti-PD-1 antibody, an anti-PD-L1 antibody, or an anti-PD-L2 antibody).

In some embodiments, the pharmaceutical composition is used to prevent or treat tumors (e.g., cancer) or infections. Preferably, the tumor is gastrointestinal neoplasms (e.g., cancer), such as colon cancer. Preferably, the infectious disease is a chronic infection.

In another aspect, the present invention relates to a method for preventing or treating a tumor (e.g., cancer) or an infectious disease in a subject or an individual, wherein the method comprises administering to the subject an effective amount of any of the anti-LAG-3 antibodies or a fragment thereof, the pharmaceutical composition, or the immunoconjugate described herein. In one embodiment, the tumor is gastrointestinal neoplasms (e.g., cancer), such as colon cancer. In one embodiment, the infectious disease is a chronic infection. In another aspect, the present invention also relates to a use of any of the anti-LAG-3 antibodies described herein or a fragment thereof in the preparation of a medicament for treating a tumor (e.g., cancer) or an infection in a subject. In one embodiment, the tumor is gastrointestinal neoplasms (e.g., cancer), such as colon cancer. In one embodiment, the infectious disease is a chronic infection.

In another aspect, the present invention relates to a method for preventing or treating a tumor (e.g., cancer) or an infectious disease in a subject or individual, wherein the method comprises administering to the subject an effective amount of any of the anti-LAG-3 antibodies or a fragment thereof, the pharmaceutical composition, or the immunoconjugate described herein, in combination with a PD-1 axis binding antagonist or a medicament or active agent comprising the PD-1 axis binding antagonist. In one embodiment, the tumor is gastrointestinal neoplasms (e.g., cancer), such as colon cancer. In one embodiment, the infectious disease is a chronic infection. In another aspect, the present invention also relates to a use of any of the anti-LAG-3 antibodies described herein or a fragment thereof, in combination with a PD-1 axis binding antagonist, in the preparation of a medicament for treating a tumor (e.g., cancer) or an infectious disease in a subject. In one embodiment, the tumor is gastrointestinal neoplasms (e.g., cancer), such as colon cancer. In one embodiment, the infectious disease is a chronic infection.

In some embodiments, the PD-1 axis binding antagonist includes, e.g., an anti-PD-1 antibody or an anti-PD-L1 antibody or an anti-PD-L2 antibody.

In some further embodiments, the prevention or treatment method described herein further comprises administering to the subject or individual one or more therapies (e.g., therapeutic modalities and/or other therapeutic agents). In some embodiments, the therapeutic modality includes a surgical treatment and/or a radiation therapy. In some embodiments, the other therapeutic agent is selected from a chemotherapeutic agent, a cytotoxic agent, a vaccine, other antibodies, an anti-infective active agent, and an immunomodulatory agent (such as an activator of a co-stimulatory molecule or an inhibitor of an immune checkpoint molecule).

In some embodiments, the subject or individual is a non-human animal. In some embodiments, the subject or individual is a mammal, preferably a human.

In one aspect, the present invention relates to a method for detecting LAG-3 in a sample, wherein the method comprises (a) contacting the sample with any of the anti-LAG-3 antibodies described herein or a fragment thereof; and (b) detecting the formation of a complex of the anti-LAG-3 antibody or the fragment thereof with LAG-3. In one embodiment, the anti-LAG-3 antibody is detectably labeled.

In some embodiments, the present invention relates to a kit or product comprising any of the anti-LAG-3 antibodies described herein or a fragment thereof. In some embodiments, the kit or product comprises the anti-LAG-3 antibody described herein or a fragment thereof and optional pharmaceutical adjuvants. In some embodiments, the kit or product further comprises instructions for administering the medicament to treat a tumor or infection.

The present invention also involves any combination of the embodiments described herein. Any of the embodiments described herein, or any combination thereof, is applicable to any and all of the anti-LAG-3 antibodies or fragments thereof, the methods, and the use described herein.

DETAILED DESCRIPTION

Abbreviations

Figure 1:
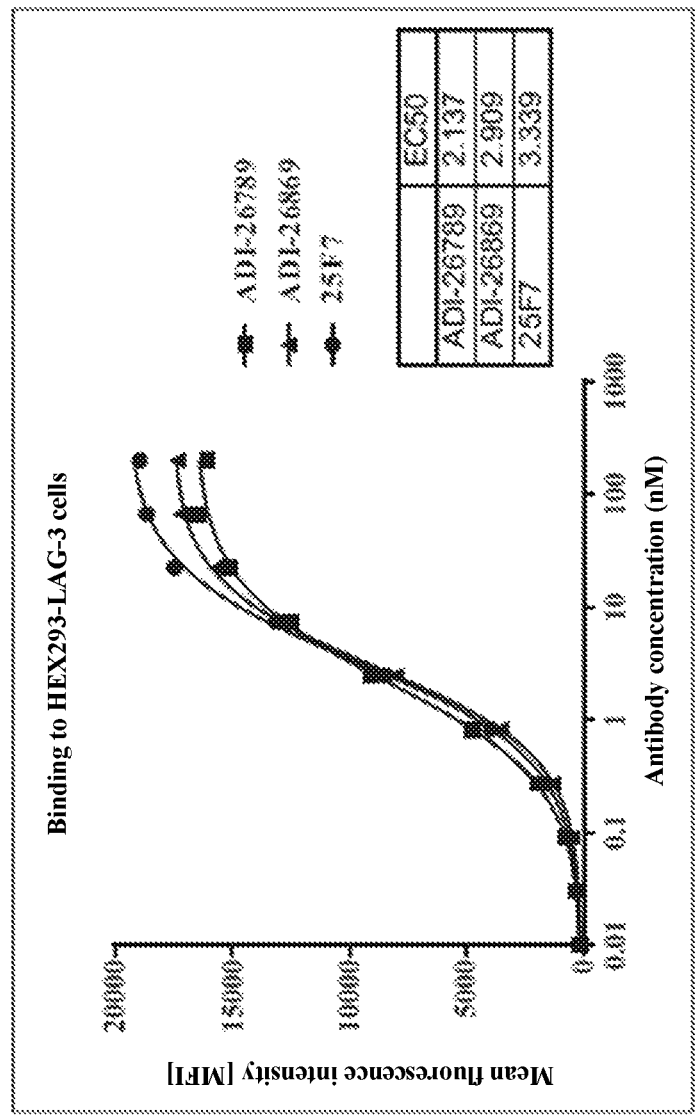
FIG. 1 shows the binding capacity of a parent antibody to hLAG-3 on the cell surface as measured by flow cytometry.

Unless otherwise stated, the abbreviations in this specification have the following meanings:

The following abbreviations are used:
ADCC Antibody-dependent cell-mediated cytotoxicity
CDC Complement-dependent cytotoxicity
CDR Complementarity determining region in a variable region of immunoglobulin
CHO Chinese hamster ovary
$EC_{50}$ A concentration resulting in 50% potency or binding
$K_D$ Equilibrium dissociation constant
ELISA Enzyme-linked immunosorbent assay
FR Antibody framework region
$IC_{50}$ A concentration producing 50% inhibition
Ig Immunoglobulin
Kabat An immunoglobulin alignment and numbering system established by Elvin A. Kabat ((1991) Sequences of Proteins of Immunological Interest, 5th Edition Public Health Service, National Institutes of Health, Bethesda, Md.)
mAb/Mab/MAb Monoclonal antibody
PCR Polymerase chain reaction
IFN Interferon
VL Light chain variable region
VH Heavy chain variable region
LC Light chain
HC Heavy chain
HCDR Heavy chain complementarity determining region
LCDR Light chain complementarity determining region Definition Before the invention is described in detail below, it should be understood that the invention is not limited to the particular methodology, protocols, and reagents described herein, as these may vary. It should also be understood that the terminology used herein is for the purpose of describing particular embodiments only, and is not intended to limit the scope of the invention, which will be limited only by the appended claims. Unless otherwise defined, all technical and scientific terms used herein have the same meaning as commonly understood by those of ordinary skill in the art to which the invention belongs.

For the purpose of explaining this specification, the following definitions will be used, and wherever appropriate, terms used in the singular may also include the plural and vice versa. It is understood that the terminology used herein is for the purpose of describing particular embodiments only and is not intended to be limiting.

The term "about" used in combination with a numerical value is intended to encompass the numerical values in a range from a lower limit less than the specified numerical value by 5% to an upper limit greater than the specified numerical value by 5%.

"Affinity" refers to the strength of the sum total of all non-covalent interactions between a single binding site of a molecule (e.g., an antibody) and its binding partner (e.g., an antigen). Unless otherwise stated, when used herein, "binding affinity" refers to the intrinsic binding affinity that reflects a 1:1 interaction between members of a binding pair (e.g., an antibody and an antigen). The affinity of a molecule X for its partner Y can generally be represented by the equilibrium dissociation constant ($K_D$). Affinity can be measured by common methods known in the art, including those known in the prior art and described herein.

The term "lymphocyte-activation gene-3" or "LAG-3" includes all isotypes, mammal (e.g., human) LAG-3, a species homolog of human LAG-3, and an analog comprising at least one common epitope of LAG-3. The amino acid and nucleotide sequences of LAG-3 (e.g., human LAG-3) are known in the art, for example, see Triebel et al., (1990) J. Exp. Med. 171: 1393-1405. In some embodiments, the term "human LAG-3" refers to human sequence LAG-3, such as the complete amino acid sequence of human LAG-3 having Genbank accession No. NP_002277. In some embodiments, the term "mouse LAG-3" refers to mouse sequence LAG-3, such as the complete amino acid sequence of mouse LAG-3 having Genbank accession No. NP_032505. LAG-3 is also known in the art as, for example, CD223. The human LAG-3 sequence may differ from human LAG-3 having Genbank accession No. NP_002277, e.g., by conservative mutations or mutations in non-conserved regions, and the LAG-3 has substantially the same biological function as the human LAG-3 having Genbank accession No. NP_002277. For example, a biological function of human LAG-3 is to have an epitope in the extracellular domain of LAG-3 to which an antibody disclosed herein specifically binds, or a biological function of human LAG-3 is to bind to an MHC class II molecule.

The term "anti-LAG-3 antibody", "anti-LAG-3", "LAG-3 antibody", or "LAG-3-binding antibody" as used herein refers to an antibody that can bind to LAG-3 protein or a fragment thereof with sufficient affinity. In one embodiment, an anti-LAG-3 antibody binds to a non-LAG-3 protein to a lesser extent than about 10%, about 20%, about 30%, about 40%, about 50%, about 60%, about 70%, about 80%, or about 90% or more of the binding of the antibody to LAG-3, as measured, for example, by radioimmunoassay (RIA), biological optical interferometry, or MSD assay.

As used herein, "monoclonal antibody" or "mAb" or "Mab" refers to an antibody derived from a single copy or clone, e.g., a eukaryotic, prokaryotic, or phage clone, and not the method by which they are produced. Monoclonal antibodies or antigen-binding fragments thereof can be produced, e.g., by hybridoma technology, recombinant technology, phage display technology, synthetic technology such as CDR grafting, or a combination of such or other techniques known in the art.

"Native antibody" refers to naturally-occurring immunoglobulin molecules of different structures. For example, a native IgG antibody is a heterotetrameric glycoprotein of about 150,000 Daltons, consisting of two identical light chains and two identical heavy chains bonded with disulfide bonds. From N-terminus to C-terminus, each heavy chain has a variable region (VH), also referred to as a variable heavy domain or a heavy chain variable domain, followed by three constant domains (CH1, CH2, and CH3). Similarly, from N-terminus to C-terminus, each light chain has a variable region (VL), also referred to as a variable light domain or a light chain variable domain, followed by a constant light (CL) domain. The light chain of an antibody can be assigned to one of two types, called kappa (κ) and lambda (λ), based on the amino acid sequence of its constant domain. "Fc region of native sequence" includes an amino acid sequence identical to the amino acid sequence of Fc regions found in nature. Human Fc region of a native sequence includes: human IgG1 Fc region of a native sequence (non-A and A allotypes), human IgG2 Fc region of a native sequence, human IgG3 Fc region of a native sequence, and human IgG4 Fc region of a native sequence, and naturally-occurring variants thereof.

"Antibody fragment" refers to a molecule different from an intact antibody, which comprises a portion of the intact antibody and binds to an antigen to which the intact antibody binds. Examples of the antibody fragment include but are not limited to Fv, Fab, Fab', Fab'-SH, F(ab')$_2$; a diabody; a linear antibody; a single-chain variable fragment (e.g., scFv); a single-domain antibody; a bivalent or bispecific antibody or a fragment thereof; a Camelidae antibody; and a bispecific antibody or multispecific antibody formed from antibody fragments.

As used herein, the term "epitope" refers to the moiety of an antigen (e.g., human LAG-3) that specifically interacts with an antibody molecule. Such moiety (referred to herein as an antigenic determinant) generally comprises, or is a part of an element such as an amino acid side chain or a sugar side chain. The antigenic determinant can be defined using methods known in the art or disclosed herein (e.g., by crystallography or by hydrogen-deuterium exchange). At least one or some moieties of the antibody molecule that specifically interact with the antigenic determinant are generally located within the CDR. Generally, an epitope has specific three-dimensional structural characteristics. Generally, an epitope has specific charge characteristics. Some epitopes are linear epitopes, while others are conformational epitopes.

"Antibody that binds to the same or overlapping epitope" as a reference antibody refers to an antibody that blocks 50%, 60%, 70%, 80%, 90%, or 95% or more of the binding of the reference antibody to its antigen in a competition assay, or conversely, the reference antibody blocking 50%, 60%, 70%, 80%, 90%, or 95% or more of the binding of the antibody to its antigen in a competition assay.

An antibody that competes with a reference antibody to bind to its antigen refers to an antibody that blocks 50%, 60%, 70%, 80%, 90%, or 95% or more of the binding of the reference antibody to its antigen in a competition assay. Conversely, the reference antibody blocks 50%, 60%, 70%, 80%, 90%, or 95% or more of the binding of the antibody to its antigen in a competition assay. Numerous types of competitive binding assays can be used to determine whether an antibody competes with another, such as direct or indirect solid-phase radioimmunoassay (RIA), direct or indirect solid-phase enzyme immunoassay (EIA), and sandwich competition assay (see, e.g., Stahli et al., 1983, Methods in Enzymology 9: 242-253).

An antibody that inhibits (e.g., competitively inhibits) the binding of a reference antibody to its antigen refers to an antibody that inhibits 50%, 60%, 70%, 80%, 90%, or 95% or more of the binding of the reference antibody to its antigen. Conversely, the reference antibody inhibits 50%, 60%, 70%, 80%, 90%, or 95% or more of the binding of the antibody to its antigen. The binding of an antibody to its antigen can be measured by affinity (e.g., equilibrium dissociation constant). Methods for determining affinity are known in the art.

An antibody that shows the same or similar binding affinity and/or specificity as a reference antibody refers to an antibody that is capable of having at least 50%, 60%, 70%, 80%, 90%, or 95% or more of the binding affinity and/or specificity of the reference antibody. This can be determined by any methods known in the art for determining binding affinity and/or specificity.

"Complementarity determining region" or "CDR region" or "CDR" is a region in an antibody variable domain that is highly variable in sequence and forms a structurally defined loop ("hypervariable loop") and/or comprises antigen contact residues ("antigen contact point"). CDRs are primarily responsible for binding to epitopes. The CDRs of the heavy and light chains are generally referred to as CDR1, CDR2, and CDR3, and are numbered sequentially from N-terminus. The CDRs located in the variable domain of the antibody heavy chains are referred to as HCDR1, HCDR2, and HCDR3, while the CDRs located in the variable domain of the antibody light chains are referred to as LCDR1, LCDR2, and LCDR3. In a given amino acid sequence of a light chain variable region or a heavy chain variable region, the exact amino acid sequence boundaries of the CDRs can be determined using any one or a combination of many well-known antibody CDR assignment systems including, e.g., Chothia based on the three-dimensional structure of antibodies and the topology of the CDR loops (Chothia et al. (1989) Nature 342: 877-883; Al-Lazikani et al., "Standard conformations for the canonical structures of immunoglobulins", Journal of Molecular Biology, 273, 927-948 (1997)), Kabat based on antibody sequence variability (Kabat et al., Sequences of Proteins of Immunological Interest, 4th edition, U.S. Department of Health and Human Services, National Institutes of Health (1987)), AbM (University of Bath), Contact (University College London), International ImMunoGeneTics database (IMGT) (imgt.cines.fr/ on the World Wide Web), and North CDR definition based on the affinity propagation clustering using a large number of crystal structures.

For example, according to different CDR determination schemes, the residues of each CDR are as follows.

| CDR | Kabat scheme | AbM scheme | Chothia scheme | Contact scheme |
|---|---|---|---|---|
| LCDR1 | L24-L34 | L24-L34 | L26-L32 | L30-L36 |
| LCDR2 | L50-L56 | L50-L56 | L50-L52 | L46-L55 |
| LCDR3 | L89-L97 | L89-L97 | L91-L96 | L89-L96 |
| HCDR1 | H31-H35B | H26-H35B | H26-H32 | H30-H35B |
| | | (Kabat numbering system) | | |
| HCDR1 | H31-H35 | H26-H35 | H26-H32 | H30-H35 |
| | | (Chothia Numbering System) | | |
| HCDR2 | H50-H65 | H50-H58 | H53-H55 | H47-H58 |
| HCDR3 | H95-H102 | H95-H102 | H96-H101 | H93-H101 |
| | | (Kabat numbering system) | | |

CDRs can also be determined based on having the same Kabat numbering positions as a reference CDR sequence (e.g., any of the exemplary CDRs of the invention).

Unless otherwise stated, in the invention, the term "CDR" or "CDR sequence" encompasses CDR sequences determined by any of the manners described above.

Unless otherwise stated, in the invention, when referring to the positions of residues in an antibody variable region (including residues in a heavy chain variable region and residues in a light chain variable region), it refers to the numbering positions according to the Kabat numbering system (Kabat et al., Sequences of Proteins of Immunological Interest, 5th Ed. Public Health Service, National Institutes of Health, Bethesda, Md. (1991)).

In one embodiment, the boundaries of CDRs of the antibodies disclosed herein are determined by Kabat rules, IMGT rules or AbM rules, or a combination thereof. For example, the sequences of CDRs are shown in Table 1.

It should be noted that boundaries of CDRs of variable regions of an antibody obtained by different assignment systems may differ. That is, CDR sequences of variable regions of an antibody defined by different assignment systems differ. Therefore, when it comes to defining an antibody with specific CDR sequences defined in the invention, the scope of the antibody also encompasses such antibody whose variable region sequences comprise the specific CDR sequences, but having claimed CDR boundaries different from the specific CDR boundaries defined by the invention as a different protocol (e.g., different assignment system rules or their combinations) is applied.

Antibodies with different specificities (i.e., different binding sites for different antigens) have different CDRs (under the same assignment system). However, although CDRs differ from antibody to antibody, only a limited number of amino acid positions within the CDRs are directly involved in antigen binding.

The smallest overlapping region can be determined using at least two of the Kabat, Chothia, AbM, Contact, and North methods, thereby providing a "minimal binding unit" for antigen binding. The minimal binding unit may be a sub-portion of the CDR. As will be clear to those skilled in the art, residues of the rest CDR sequences can be determined by antibody structure and protein folding. Therefore, any variants of the CDRs given herein will also be considered in the invention. For example, in one CDR variant, the amino acid residues in the minimal binding unit may remain unchanged, while other CDR residues defined by Kabat or Chothia may be substituted by conservative amino acid residues. Five major classes of antibodies are known in the art: IgA, IgD, IgE, IgG, and IgM, and several of these classes can be further divided into subclasses (isotypes), e.g., $IgG_1$, $IgG_2$, $IgG_3$, $IgG_4$, $IgA_1$, and $IgA_2$. The heavy chain constant domains that correspond to different classes of immunoglobulins are referred to as α, δ, ε, γ, and μ, respectively.

"Antibody in IgG form" refers to the heavy chain constant region of the antibody belonging to the IgG form. Heavy chain constant regions of all antibodies of the same type are identical, and heavy chain constant regions of antibodies of different types are different. For example, an antibody in the form of IgG4 refers to the Ig domain of its heavy chain constant region being an Ig domain of IgG4. The term "PD-1 axis binding antagonist" refers to a molecule that inhibits the interaction of a PD-1 axis binding partner with one or more of its binding partners, thereby removing T-cell dysfunction resulting from the signal transduction on a PD-1 signaling axis, wherein one outcome is restoring or enhancing T-cell functions (e.g., proliferation, cytokine production, and target-cell killing). As used herein, the PD-1 axis binding antagonist includes a PD-1 binding antagonist (e.g., an anti-PD-1 antibody), a PD-L1 binding antagonist (e.g., an anti-PD-L1 antibody), and a PD-L2 binding antagonist (e.g., an anti-PD-L2 antibody).

The term "PD-1 binding antagonist" refers to a molecule that reduces, blocks, inhibits, eliminates or interferes with the signal transduction resulting from the interaction of PD-1 with one or more of its binding partners (such as PD-L1 and PD-L2). In some embodiments, the PD-1 binding antagonist is a molecule that inhibits the binding of PD-1 to one or more of its binding partners. In a particular aspect, the PD-1 binding antagonist inhibits the binding of PD-1 to PD-L1 and/or PD-L2. For example, the PD-1 binding antagonist includes an anti-PD-1 antibody, an antigen-binding fragment thereof, an immunoadhesin, a fusion protein, an oligopeptide, and other molecules that reduce, block, inhibit, eliminate, or interfere with the signal transduction resulting from the interaction of PD-1 with PD-L1 and/or PD-L2. In one embodiment, the PD-1 binding antagonist reduces negative co-stimulatory signal mediated by or via cell surface proteins expressed on T lymphocytes (signal transduction mediated via PD-1), thereby rendering dysfunctional T cells less dysfunctional (e.g., enhancing the effector response to antigen recognition). In some embodiments, the PD-1 binding antagonist is an anti-PD-1 antibody. In a specific embodiment, the PD-1 binding antagonist is MDX-1106 (nivolumab), MK-3475 (pembrolizumab), CT-011 (pidilizumab), or AMP-224 disclosed in WO 2015/095423. In a specific embodiment, the anti-PD-1 antibody is "Antibody C" disclosed in WO 2017/133540. In another specific embodiment, the anti-PD-1 antibody is "Antibody D" disclosed in WO 2017/025016.

The term "PD-L1 binding antagonist" refers to a molecule that reduces, blocks, inhibits, eliminates or interferes with the signal transduction resulting from the interaction of PD-L1 with one or more of its binding partners (such as PD-1 and B7-1). In some embodiments, the PD-L1 binding antagonist is a molecule that inhibits the binding of PD-L1 to its binding partners. In a particular aspect, the PD-L1 binding antagonist inhibits the binding of PD-L1 to PD-1 and/or B7-1. In some embodiments, the PD-L1 binding antagonist includes an anti-PD-L1 antibody, an antigen-binding fragment thereof, an immunoadhesin, a fusion protein, an oligopeptide, and other molecules that reduce, block, inhibit, eliminate, or interfere with the signal transduction resulting from the interaction of PD-L1 with one or more of its binding partners (such as PD-1 and B7-1). In one embodiment, the PD-L1 binding antagonist reduces negative co-stimulatory signals mediated by or via cell surface proteins expressed on T lymphocytes (signal transduction mediated via PD-L1), thereby rendering dysfunctional T cells less dysfunctional (e.g., enhancing the effector response to antigen recognition). In some embodiments, the PD-L1 binding antagonist is an anti-PD-L1 antibody. In a particular aspect, the anti-PD-L1 antibody is YW243.55.S70, MDX-1105, MPDL3280A, or MEDI4736 disclosed in WO 2015/095423.

The term "PD-L2 binding antagonist" refers to a molecule that reduces, blocks, inhibits, eliminates or interferes with the signal transduction resulting from the interaction of PD-L2 with one or more of its binding partners (such as PD-1). In some embodiments, the PD-L2 binding antagonist is a molecule that inhibits the binding of PD-L2 to one or more of its binding partners. In a particular aspect, the PD-L2 binding antagonist inhibits the binding of PD-L2 to PD-1. In some embodiments, the PD-L2 antagonist includes an anti-PD-L2 antibody, an antigen-binding fragment thereof, an immunoadhesin, a fusion protein, an oligopeptide, and other molecules that reduce, block, inhibit, eliminate, or interfere with the signal transduction resulting from the interaction of PD-L2 with one or more of its binding partners (such as PD-1). In one embodiment, the PD-L2 binding antagonist reduces negative co-stimulatory signals mediated by or via cell surface proteins expressed on T lymphocytes (signal transduction mediated via PD-L2), thereby rendering dysfunctional T cells less dysfunctional (e.g., enhancing the effector response to antigen recognition). In some embodiments, the PD-L2 binding antagonist is an immunoadhesin. The term "antibody-dependent cell-mediated cytotoxicity" or "ADCC" refers to a form of cytotoxicity in which secreted immunoglobulins binding to Fc receptors (FcRs) present on certain cytotoxic cells (e.g., NK cells, neutrophils, and macrophages) enable these cytotoxic effector cells to specifically bind to an antigen-bearing target cell and subsequently kill the target cell with cytotoxins. The primary cells mediating ADCC, NK cells, express FcγRIII only, whereas monocytes express FcγRI, FcγRII, and FcγRIII. Table 3 on page 464 of Ravetch and Kinet, Annu. Rev. Immunol. 9: 457-92 (1991) summarizes the FcR expression on hematopoietic cells. An in-vitro ADCC assay can be performed to evaluate the ADCC activity of the molecule of interest, such as described in U.S. Pat. No. 5,500,362 or 5,821,337, or U.S. Pat. No. 6,737,056 (Presta). Effector cells that can be used for such assays include PBMC and NK cells. Optionally/alternatively, the ADCC activity of the molecule of interest can be assessed in vivo, e.g., in an animal model, such as that disclosed in Clynes et al., PNAS (USA) 95: 652-656 (1998). The term "cytotoxic agent" or "cytotoxic factor" used in the present invention refers to a substance that inhibits or prevents the cell function and/or causes cell death or destruction. Examples of the cytotoxic agent are disclosed in WO2015/153513, WO2016/028672 or WO2015/138920.

The term "therapeutic agent" as described herein comprises any substance effective in preventing or treating tumors (such as cancer) and infections (such as chronic infections), including a chemotherapeutic agent, a cytotoxic agent, a vaccine, other antibodies, an anti-infective active agent or an immunomodulatory agent, such as any substance disclosed in WO2016/028672 or WO2015/138920 that can be used in combination with an anti-LAG-3 antibody.

"Chemotherapeutic agents" include chemical compounds useful in treatment of cancer. Examples of chemotherapeutic agents are those disclosed in WO2015/153513, WO2016/028672, or WO2015/138920. The term "cytokine" is a general term for proteins that are released by a cell population and act as intercellular mediators on another cell. Examples of such cytokines are lymphokines and monokines; interleukins (IL), such as IL-1, IL-1α, IL-2, IL-3, IL-4, IL-5, IL-6, IL-7, IL-8, IL-9, IL-11, IL-12, and IL-15; tumor necrosis factors, such as TNF-α or TNF-β; and other polypeptide factors, including LIF and kit ligand (KL) and γ-interferon. As used herein, the term cytokine includes proteins from natural sources or from recombinant cell cultures and biologically active equivalents of cytokines of native sequence, including small molecule entities produced by artificial synthesis, and pharmacologically acceptable derivatives and salts thereof.

The term "co-stimulatory molecule" refers to a relevant binding partner that specifically binds to a co-stimulatory ligand on a T cell and thus allows a T-cell-mediated co-stimulatory response (for example, but not limited to, proliferation). Co-stimulatory molecules are cell surface molecules other than antigen receptors or ligands thereof required for a highly efficient immune response. Co-stimulatory molecules include, but are not limited to: MHC Class I molecules, TNF receptor proteins, immunoglobulin-like proteins, cytokine receptors, integrins, signaling lymphocytic activation molecules (SLAM proteins), NK cell activating receptor, BTLA, Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8α, CD8β, IL2Rβ, IL2Rγ, IL7Rα, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and ligands that specifically bind to CD83.

The term "activator" or "agonist" includes substances that increase certain parameters (e.g., activity) of a given molecule (e.g., a co-stimulatory molecule). For example, this term includes substances that increase the activity (e.g., co-stimulatory activity) of a given molecule by at least 5%, 10%, 25%, 50%, 75%, or more.

The term "immune checkpoint molecule" refers to the group of molecules on the cell surface of CD4 T cells and CD8 T cells. These molecules can effectively act as "brakes" that down-regulate or suppress anti-tumor immune responses Immune checkpoint molecules include, but are not limited to, programmed death receptor 1 (PD-1), cytotoxic T lymphocyte antigen 4 (CTLA-4), B7H1, B7H4, OX-40, CD137, CD40, and LAG-3, which directly inhibit immune cells.

The term "inhibitor" or "antagonist" includes substances that reduce certain parameters (e.g., activity) of a given molecule (e.g., an immune checkpoint inhibitory protein). For example, this term includes substances that inhibit the activity (e.g., PD-1 or PD-L1 activity) of a given molecule by at least 5%, 10%, 20%, 30%, 40% or more. Therefore, the inhibitory effect needs not be 100%.

The term "diabody" refers to an antibody fragment having two antigen binding sites, the fragment comprising a heavy chain variable domain (VH) linked to a light chain variable domain (VL) in one polypeptide chain (VH-VL). By using a linker that is too short for pairing two domains in the same chain, the domains are forced to pair with the complementarity domains of another chain to form two antigen-binding sites. Diabodies can be bivalent or bispecific. Diabodies are described in greater detail in, e.g., EP 404,097; WO 1993/01161; Hudson et al., Nat. Med. 9:129-134 (2003); and Hollinger et al., Proc. Natl. Acad. Sci. USA, 90:6444-6448 (1993). Tribodies and tetrabodies are also described in Hudson et al., Nat. Med. 9:129-134 (2003).

"Functional Fc region" possesses the "effector functions" of Fc regions of native sequences. Exemplary "effector functions" include C1q binding, CDC, Fc receptor binding, ADCC, phagocytosis, cell surface receptors (e.g., B cell receptors, or BCRs) down-regulation, and the like. Such effector functions generally require that the Fc region is associated with a binding domain (e.g., an antibody variable domain) and can be assessed using a variety of assays, such as those disclosed herein.

"Effector function" refers to biological activities which can be attributed to the antibody Fc region and vary with the antibody isotype. Examples of antibody effector functions include: C1q binding and complement-dependent cytotoxicity (CDC), Fc receptor binding, antibody-dependent cell-mediated cytotoxicity (ADCC), phagocytosis, cell surface receptors (e.g., B cell receptors) down-regulation, and B cell activation. "Human effector cell" refers to a leukocyte that expresses one or more FcRs and executes effector functions. In certain embodiments, the cell expresses at least Fc effectors and executes effector functions of ADCC. Examples of human leukocytes mediating ADCC include peripheral blood mononuclear cells (PBMC), natural killer (NK) cells, monocytes, cytotoxic T cells, and neutrophils. Effector cells can be isolated from their natural sources, such as blood.

The term "effective amount" refers to an amount or dosage of the antibody or fragment or conjugate or composition of the invention which generates expected effects in a patient in need of treatment or prevention after administered to the patient in a single or multiple doses. The effective amount can be easily determined by an attending physician as a person skilled in the art by considering a variety of factors as follows: species such as mammals; its size, age, and general health; the specific disease involved; the extent or severity of the disease; response in an individual patient; specific antibody administered; route of administration; bioavailability characteristics of the administered formulation; selected dose regimen; and use of any concomitant therapy.

"Therapeutically effective amount" refers to an amount effective to achieve a desired therapeutic outcome at a required dosage for a desired period of time. The therapeutically effective amount of an antibody or an antibody fragment, or conjugate or composition thereof can vary depending on a variety of factors such as morbid state, age, sex, and weight of an individual, and the ability of the antibody or antibody portion to elicit a desired response in the individual. The therapeutically effective amount is also such an amount in which any toxic or undesired effect of the antibody or antibody fragment, or conjugate or composition thereof is inferior to the therapeutically beneficial effect. The "therapeutically effective amount" inhibits a measurable parameter (e.g., tumor growth rate) by preferably at least about 20%, more preferably at least about 40%, even more preferably at least about 50%, 60%, or 70%, and still more preferably at least about 80%, relative to untreated subjects. The ability of a compound to inhibit a measurable parameter (e.g., cancer) can be evaluated in an animal model system that predicts efficacy in human tumors. Optionally, such property of a composition can be evaluated by examining the inhibition ability of the compound, which can be measured in vitro by assays known to those skilled.

"Prophylactically effective amount" refers to an amount effective to achieve a desired prophylactic outcome at a required dosage for a desired period of time. Generally, since a prophylactic dose is administered in a subject before or at an earlier stage of a disease, a prophylactically effective amount will be less than a therapeutically effective amount.

"Antibodies and antigen-binding fragments thereof" suitable for the invention include, but are not limited to, polyclonal, monoclonal, monovalent, bispecific, heteroconjugate, multispecific, recombinant, heterologous, heterohybrid, chimeric, humanized (especially CDR-grafted), deimmunized, or human antibodies, Fab fragments, Fab' fragments, F (ab')$_2$ fragments, fragments generated from a Fab expression library, Fd, Fv, disulfide-stablized Fv (dsFv), single-chain antibodies (e.g., scFv), diabodies or tetrabodies (Holliger P. et al. (1993) Proc. Natl. Acad. Sci. USA 90 (14), 6444-6448), nanobodies (also referred to as single-domain antibodies), anti-idiotypic (anti-Id) antibodies (including, e.g., anti-Id antibodies against the antibodies of the invention), and epitope binding fragments of any of the above.

"Fab" fragment includes a heavy chain variable domain and a light chain variable domain, and also includes the constant domain of the light chain and the first constant domain (CH1) of the heavy chain. An Fab' fragment differs from the Fab fragment due to addition of some residues (including one or more cysteine from an antibody hinge region) to the carboxyl terminal of the heavy chain CH1 domain. Fab'-SH refers to an Fab' in which the cysteine residue of the constant domain carries a free thiol group. An F(ab')2 antibody fragment was originally generated as paired Fab' fragments with hinge cysteines between the Fab' fragments. Other chemical couplings of antibody fragments are also known.

The term "Fc region" is used herein to define a C-terminal region of an immunoglobulin heavy chain, comprising at least a portion of a constant region. The term includes Fc regions and variant Fc regions of native sequences. In certain embodiments, a human IgG heavy chain Fc region extends from Cys226 or Pro230 to the carbonyl end of the heavy chain. However, the C-terminal lysine (Lys447) of the Fc region may or may not be present. Unless otherwise stated, the numbering of amino acid residues in the Fc region or constant region is based on an EU numbering system, which is also called EU index as described in Kabat et al., Sequences of Proteins of Immunological Interest, 5th Ed. Public Health Service, National Institutes of Health, Bethesda, Md., 1991.

The term "variable region" or "variable domain" refers to a domain of a heavy or light chain of an antibody involved in the binding of the antibody to an antigen. Variable domains of heavy and light chains of native antibodies often have similar structures, wherein each domain contains four conserved framework regions (FR) and three complementarity determining regions (CDR). (See, e.g., Kindt et al., Kuby Immunology, 6$^{th}$ Ed., W.H. Freeman and Co. p 91 (2007)). A single VH or VL domain may be sufficient to provide antigen-binding specificity. In addition, a VH or VL domain from an antibody binding to a particular antigen can be used to isolate antibodies that bind to the antigen, so as to screen libraries of complementarity VL or VH domains, respectively. See, e.g., Portolano et al., J. Immunol., 150: 880-887 (1993); Clarkson et al., Nature, 352:624-628 (1991).

"Framework" or "FR" refers to variable domain residues other than complementarity determining region (CDR) residues. An FR of a variable domain generally consists of four FR domains: FR1, FR2, FR3, and FR4. Therefore, CDR and FR sequences generally appear in the following sequence of a heavy chain variable domain (VH) (or a light chain variable domain (VL)): FR1-HCDR1 (LCDR1)-FR2-HCDR2 (LCDR2)-FR3-HCDR3 (LCDR3)-FR4.

Unless otherwise stated, the numbering of residues in various domains of antibodies is based on the EU numbering system, which is also called EU index as described in Kabat et al., Sequences of Proteins of Immunological Interest, 5th Ed. Public Health Service, National Institutes of Science Health, Bethesda, Md., 1991.

The terms "full-length antibody", "whole antibody" and "intact antibody" are used interchangeably herein to refer to an antibody having a substantially similar structure to a native antibody structure or an antibody having a heavy chain that contains an Fc region as defined herein.

"Fv" is the smallest antibody fragment that contains an intact antigen-binding site. In one embodiment, a double-chain Fv consists of one heavy chain variable domain and one light chain variable domain in a tight, non-covalently associated dimer. In a single-chain Fv (scFv), one heavy chain variable domain and one light chain variable domain can be covalently linked through a flexible peptide linker so that the light chain and heavy chain can be associated with a structure similar to the "Dimer" structure of the double-chain type. In this configuration, it is the three CDRs of each variable domain that define the antigen-binding site on the surface of the VH-VL dimer. To summarize, the six CDRs impart antigen-binding specificity to the antibody. Nevertheless, even a single variable domain (or containing only half Fv of the three CDRs specific to the antigen) has the ability to recognize and bind to an antigen, although the affinity is lower than an intact binding site. For a review of scFv, see, e.g., Pluckthun in The Pharmacology of Monoclonal Antibodies, Vol. 113, Edited by Rosenburg and Moore, (Springer-Verlag, New York, 1994), pages 269-315.

The terms "host cell", "host cell line" and "host cell culture" are used interchangeably and refer to cells into which an exogenous nucleic acid is introduced, including generations of such cells. Host cells include "transformants" and "transformed cells", which include primary transformed cells and generations derived therefrom, regardless of the number of passages. A generation may not be completely identical in nucleic acid content to the parent cell, but may contain mutations. Mutant generations having the same function or biological activity that are screened or selected from the initially transformed cells are included herein. "Human antibody" refers to an antibody having an amino acid sequence which corresponds to the amino acid sequence of an antibody generated by a human or human cell or derived from a non-human source that utilizes human antibody libraries or other human antibody encoding sequences. This definition of a human antibody explicitly excludes humanized antibodies containing non-human antigen-binding residues.

"Human consensus framework" refers to a framework that represents the most frequently occurring amino acid residues in the selection of human immunoglobulin VL or VH framework sequences. Generally, the selection of human immunoglobulin VL or VH sequences is a selection from subtypes of variable domain sequences. Generally, the subtype of the sequence is a subtype disclosed in Kabat et al., Sequences of Proteins of Immunological Interest, Fifth Edition, NIH Public Publication 91-3242, Bethesda Md. (1991), Volumes 1-3. In one embodiment, for VL, the subtype is the subtype kappa I as in Kabat et al. (see above). In one embodiment, for VH, the subtype is the subtype III as in Kabat et al. (see above). "Humanized" antibody refers to a chimeric antibody comprising amino acid residues from non-human CDRs and amino acid residues from human FRs. In some embodiments, a humanized antibody will comprise substantially all of at least one, typically two variable domains, wherein all or substantially all CDRs (e.g., CDRs) correspond to those of a non-human antibody, and all or substantially all FRs correspond to those of a human antibody. A humanized antibody may optionally comprise at least a portion of an antibody constant region derived from a human antibody. The "humanized form" of an antibody (e.g., a non-human antibody) refers to an antibody that has been humanized The terms "cancer" and "cancerous" refer to or describe a physiological disease in mammals that is typically characterized by unregulated cell growth. Examples of cancers include, but are not limited to, carcinomas, lymphomas, blastomas, sarcomas, and leukemias or lymphoid malignancies. More specific examples of such cancers include, but are not limited to, squamous cell carcinoma (e.g., epithelial squamous cell carcinoma), lung cancer (including small cell lung cancer, non-small cell lung cancer, lung adenocarcinoma, and lung squamous cell carcinoma), peritoneal cancer, hepatocellular carcinoma, gastric cancer (including gastrointestinal cancer and gastrointestinal stromal cancer), pancreatic cancer, glioblastoma, cervical cancer, ovarian cancer, liver cancer, bladder cancer, urinary tract cancer, liver tumor, breast cancer, colon cancer, rectal cancer, colorectal cancer, endometrial or uterine cancer, salivary adenocarcinoma, kidney cancer, prostate cancer, vulval cancer, thyroid cancer, liver cancer, anal cancer, penile cancer, melanoma, superficial diffuse melanoma, lentigo maligna melanoma, acral melanoma, nodular melanoma, multiple myeloma and B-cell lymphoma, chronic lymphocytic leukemia (CLL), acute lymphoblastic leukemia (ALL), hairy cell leukemia, chronic myelogenous leukemia, and post-transplant lymphoproliferative disorder (PTLD), as well as abnormal vascular proliferation associated with phakomatoses, edema (such as those associated with brain tumors), and Meigs syndrome, brain tumors and brain cancer, and head and neck cancer, and related metastases.

The terms "cell proliferative disorder" and "proliferative disorder" refer to disorders associated with a certain extent of abnormal cell proliferation. In one embodiment, the cell proliferative disorder refers to cancer.

The term "tumor" refers to all neoplastic cell growth and proliferation regardless of whether malignant or benign, and all pre-cancerous and cancerous cells and tissues. The terms "cancer", "cancerous", "cell proliferative disorder", "proliferative disorder", and "tumor" are not mutually exclusive when referred to herein.

The term "infectious disease" refers to a disease caused by a pathogen, including, for example, viral infection, bacterial infection, fungal infection, or protozoan such as parasitic infection.

The term "chronic infection" refers to such an infection in which an infectious agent (e.g., a pathogen such as a virus, bacteria, protozoa such as a parasite, fungus, or the like) has induced an immune response in an infected host, but has not been cleared or eliminated from the host as in acute infections. Chronic infections can be persistent, latent or slow. While acute infections are generally resolved by immune system within days or weeks (such as the flu), persistent infections can last for months, years, decades, or a lifetime at relatively lower levels (e.g., hepatitis B). In contrast, latent infections are characterized by long-term asymptomatic activity, interrupted at times by rapidly increasing hyperinfections and elevated pathogen levels (such as herpes simplex). Finally, slow infections are characterized by gradual and continuous progressions of disease symptoms, such as a long incubation period followed by prolonged and progressive clinical processes after the onset of clinical symptoms. Unlike latent and persistent infections, chronic infections may not begin in the acute phase of virus proliferation (e.g., picornaviruses infection, visna virus, scrapie, Creutzfeldt-Jakob disease). Exemplary infectious agents capable of inducing chronic infections include viruses (e.g., cytomegalovirus, EB virus, hepatitis B virus, hepatitis C virus, herpes simplex virus types I and II, human immunodeficiency virus types 1 and 2, human papilloma virus, human T lymphocyte virus types 1 and 2, varicella-zoster virus, etc.), bacteria (e.g., *Mycobacterium tuberculosis, Listeria* spp., *Klebsiella pneumoniae, Streptococcus pneumoniae, Staphylococcus aureus, Borrelia* spp., *Helicobacter pylori*, etc.), protozoa such as parasites (e.g., *Leishmania* spp., *Plasmodium falciparum, Schistosoma* spp., *Toxoplasma* spp., *Trypanosoma* spp., *Taenia carssiceps*, etc.), and fungi (e.g., *Aspergillus* spp., *Candida albicans, Coccidioides immitis, Histoplasma capsulatum, Pneumocystis carinii*, etc.). Additional infectious agents include prions or misfolded proteins which affect brain or neuron structure by further propagating protein misfolding in these tissues, leading to the formation of amyloid plaques (which cause cell death, tissue damage, and eventually, death). Examples of diseases caused by prion infections include Creutzfeldt-Jakob disease and its varieties, Gerstmann-Straussler-Scheinker syndrome (GSS), fatal familial insomnia (sFI), kuru, scrapie, bovine spongiform encephalopathy (BSE) in cattle (aka "mad cow" disease), and various other encephalopathy in various animal forms [e.g., transmissible mink encephalopathy (TME), chronic wasting disease (CWD) in white-tailed deer, elk and mule deer, feline spongiform encephalopathy, exoticungulate encephalopathy (EUE) in nyala, oryx and greater kudu, spongiform encephalopathy of the ostrich].

"Immunoconjugate" is an antibody which is conjugated to one or more other substances, including but not limited to cytotoxic agents or labels.

The term "label" used herein refers to a compound or composition which is directly or indirectly conjugated or fused to an agent, such as a polynucleotide probe or an antibody, and facilitates the detection of the agent to which it is conjugated or fused. The label itself can be detectable (e.g., a radioisotope label or a fluorescent label) or can catalyze a chemical change of a detectable substrate compound or composition in the case of enzymatic labeling. The term is intended to encompass direct labeling of a probe or an antibody by coupling (i.e., physical linking) a detectable substance to the probe or the antibody and indirect labeling of a probe or an antibody by reacting with another reagent which is directly labeled. Examples of indirect labeling include detection of a primary antibody using a fluorescently labeled secondary antibody, and end labeling of a biotinylated DNA probe such that it can be detected with a fluorescently labeled streptavidin.

"Individual" or "subject" includes mammals. Mammals include, but are not limited to, domestic animals (e.g., cattle, goat, cat, dog, and horse), primates (e.g., human and non-human primates such as monkey), rabbit, and rodents (e.g., mouse and rat). In some embodiments, the individual or subject is a human.

An "isolated" antibody is one that has been separated from components of its natural environment. In some embodiments, the antibody is purified to a purity greater than 95% or 99% as determined by, e.g., electrophoresis [e.g., SDS-PAGE, isoelectric focusing (IEF), capillary electrophoresis] or chromatography (e.g., ion exchange or reversed phase HPLC). For a review of methods for assessing antibody purity, see, e.g., Flatman et al., J. Chromatogr., B848:79-87 (2007).

An "isolated" nucleic acid refers to a nucleic acid molecule which has been separated from components of its natural environment. The isolated nucleic acid includes a nucleic acid molecule contained in a cell that normally contains the nucleic acid molecule, but present extrachromosomally or at a chromosomal location that is different from its natural chromosomal location.

"Isolated nucleic acid encoding an anti-LAG-3 antibody or a fragment thereof" refers to one or more nucleic acid molecules encoding an antibody heavy or light chain (or fragment thereof), including such nucleic acid molecules in a single vector or separate vectors, and such nucleic acid molecules present at one or more locations in a host cell.

The terms "nucleic acid", "nucleic acid sequence", "nucleotide sequence" or "polynucleotide sequence" and "polynucleotide" are used interchangeably. They refer to nucleotides (deoxyribonucleotides or ribonucleotides) of any length in polymer form or analogs thereof. A polynucleotide may be single-stranded or double-stranded, and if single-stranded, may be a coding or non-coding (antisense) strand. Polynucleotides can include modified nucleotides, such as methylated nucleotides and nucleotide analogs. The sequence of nucleotide can be interrupted by non-nucleotide components. The polynucleotide may be further modified after polymerization, such as by conjugation with a labeling component. A nucleic acid can be a recombinant polynucleotide or a polynucleotide which does not exist in nature, or is linked in an unnatural layout to another polynucleotide from genomic source, cDNA source, semi-synthetic source, or synthetic source.

The terms "polypeptide", "peptide" and "protein" (if in single chain) are used interchangeably herein and refer to amino acid polymers of any length. The polymer can be linear or branched, can comprise modified amino acids, and can be interrupted by non-amino acids. The term also includes amino acid polymers which have been modified (e.g., formation of disulfide bond, glycosylation, lipidation, acetylation, phosphorylation, or any other operation such as conjugation with a labeling component). Polypeptides can be isolated from natural sources, can be produced from eukaryotic or prokaryotic hosts via recombinant techniques, and can be the products of synthetic methods.

The calculation of sequence identity between sequences is performed as follows.

To determine the percent identity of two amino acid sequences or two nucleic acid sequences, the sequences are aligned for optimal comparison purposes (e.g., for optimal alignment, gaps can be introduced in the first and second amino acid sequences or in one or both of nucleic acid sequences, or non-homologous sequences can be discarded for comparison purposes). In one preferred embodiment, for comparison purposes, the length of the aligned reference sequence is at least 30%, preferably at least 40%, more preferably at least 50%, 60%, and even more preferably at least 70%, 80%, 90%, 100% of the length of the reference sequence Amino acid residues or nucleotides at corresponding amino acid positions or nucleotide positions are then compared. When a position in the first sequence is occupied by the same amino acid residue or nucleotide at the corresponding position in the second sequence, then the molecules are identical at this position.

A mathematical algorithm can be used to achieve the sequence comparison and calculation of percent identity between two sequences. In one preferred embodiment, the percent identity between two amino acid sequences is determined with the Needlema and Wunsch R1970) J. Mol. Biol., 48:444-4531 algorithm (available at http://www.gcg.com) which has been integrated into the GAP program of the GCG software package, using the Blossom 62 matrix or PAM250 matrix and gap weights of 16, 14, 12, 10, 8, 6, or 4 and length weights of 1, 2, 3, 4, 5, or 6. In yet another preferred embodiment, the percent identity between two nucleotide acid sequences is determined with the GAP program (available at http://www.gcg.com) of the GCG software package, using the NWSgapdna.CMP matrix and gap weights of 40, 50, 60, 70, or 80 and length weights of 1, 2, 3, 4, 5 or 6. A particularly preferred parameter set (and one that should be used unless otherwise stated) is a Blossom 62 scoring matrix with a gap penalty of 12, a gap extension penalty of 4, and a frameshift gap penalty of 5.

The percent identity between two amino acid sequences or nucleotide sequences can also be determined with PAM120 weighted remainder table, gap length penalty of 12 and gap penalty of 4, using the E. Meyers and W. Miller algorithms which have been incorporated into the ALIGN program (version 2.0) ((1989) CABIOS, 4:11-17).

Additionally or alternatively, the nucleic acid sequences and protein sequences described herein can be further used as "query sequences" to perform searches against public databases to, e.g., identify other family member sequences or related sequences. For example, such searches can be performed with the NBLAST and XBLAST programs of Altschul et al., (1990) J. Mol. Biol., 215:403-10. BLAST nucleotide searches can be performed with the NBLAST program, score=100, word length=12, to obtain nucleotide sequences homologous to the nucleic acid molecule of the invention. BLAST protein searches can be performed with the XBLAST program, score=50, word length=3, to obtain amino acid sequences homologous to the protein molecule of the invention. To obtain gapped alignment results for comparison purposes, gapped BLAST can be used as described in Altschul et al. (1997) Nucleic Acids Res. 25:3389-3402. When using BLAST and gapped BLAST programs, the default parameters of the respective programs (e.g., XBLAST and NBLAST) can be used. See http://www.ncbi.nlm.nih.gov. As used herein, the term "hybridization under conditions of low stringency, medium stringency, high stringency, or extreme stringency" describes hybridization and washing conditions. Instructions for performing hybridization reactions can be found in Current Protocols in Molecular Biology, John Wiley & Sons, N.Y. (1989), 6.3.1-6.3.6, which is incorporated by reference. Aqueous and non-aqueous methods are described in the references and either method can be used. The specific hybridization conditions mentioned herein are as followed: 1) low stringency hybridization conditions are in 6× sodium chloride/sodium citrate (SSC) at about 45° C., followed by two washes in 0.2×SSC, 0.1% SDS at least at 50° C. (for low stringency conditions, the temperature of the washes can be increased to 55° C.); 2) medium stringency hybridization conditions are in 6×SSC at about 45° C., followed by one or more washes in 0.2×SSC, 0.1% SDS at about 60° C.; 3) high stringency hybridization conditions are in 6×SSC at about 45° C., followed by one or more washes in 0.2×SSC, 0.1% SDS at 65° C.; and preferably 4) extreme stringency hybridization conditions are in 0.5 M sodium phosphate, 7% SDS at 65° C., followed by one or more washes in 0.2×SSC, 0.1% SDS at 65° C. Extreme stringency condition (4) is a preferred condition and the one that should be used unless otherwise stated.

The term "pharmaceutical composition" refers to such a composition that exists in a form which allows the biological activity of the active ingredient contained therein to be effective, and does not contain additional ingredients having unacceptable toxicity to a subject to which the composition is administered. The term "pharmaceutical supplementary material" refers to diluents, adjuvants (e.g., Freund's adjuvants (complete and incomplete)), carriers, excipients, or stabilizers, etc., which are co-administered with active substance.

As used herein, "treatment" (or "treat" or "treating") refers to slowing, interrupting, arresting, alleviating, stopping, reducing, or reversing the progression or severity of an existing symptom, disorder, condition, or disease.

As used herein, "prevention" (or "prevent" or "preventing") includes the inhibition of the onset or progression of a disease or disorder or a symptom of a particular disease or disorder. In some embodiments, subjects with family history of cancer are candidates for preventive regimens. Generally, in the context of cancer, the term "prevention" refers to the administration of a drug prior to the onset of signs or symptoms of a cancer, particularly in subjects at risk of cancer.

The term "anti-infective agent" includes any molecule that specifically inhibits or eliminates the growth of microorganisms such as viruses, bacteria, fungi, or protozoa, e.g., parasites, and is not lethal to the host, at the administration concentration and interval of administration. As used herein, the term anti-infective agent includes antibiotics, antibacterials, antivirals, antifungals, and antiprotozoals. In one specific aspect, the anti-infective agent is non-toxic to the host at the administration concentration and interval of administration.

Antibacterial anti-infective agents or antibacterial agents can be broadly classified into bactericidal (i.e., directly killing) or bacteriostatic (i.e., preventing division). Antibacterial anti-infective agents can be further classified into narrow-spectrum antibacterial agents (i.e., affecting only limited bacterial subtypes, such as Gram-negative, etc.) or broad-spectrum antibacterial agents (i.e., affecting a wide range of species). Examples include amikacin, gentamicin, geldanamycin, herbimycin, mupirocin, furantoin, pyrazinamide, quinupristin/dalfopristin, rifampicin/rifampin, isoniazid and pyrazinamide tablets, or tinidazole.

The term "antiviral" includes any substance that inhibits or eliminates the growth, pathogenicity, and/or survival of a virus. This includes, e.g., acyclovir, cidofovir, zidovudine, didanosine (ddI, VIDEX), zalcitabine (ddC, HMD), stavudine (d4T, ZERIT), lamivudine (3TC, EPIVIR), abacavir (ZIAGEN), emtricitabine (EMTRIVA), etc.

The term "antifungal" includes any substance that inhibits or eliminates the growth, pathogenicity, and/or survival of a fungus. This includes, e.g., natamycin, rimocidin, filipin, nystatin, amphotericin B, candicin, patchouli, neem seed oil, coconut oil, etc.

The term "antiprotozoal agent" includes any substance that inhibits or eliminates the growth, pathogenicity, and/or survival of protozoan organisms (e.g., parasites). Examples of antiprotozoal agents include antimalarials such as quinine, quinidine, etc.

For exemplary antibacterials, antivirals, antifungals, and antiprotozoals, see, e.g., WO2010/077634 and the like. For anti-infective agents, see also, e.g., WO2014/008218, WO2016/028672 or WO2015/138920. The term "vector" as used herein refers to a nucleic acid molecule capable of proliferating another nucleic acid to which it is linked. The term includes vectors that serve as self-replicating nucleic acid structures as well as vectors binding to the genome of a host cell into which they have been introduced. Some vectors are capable of directing the expression of a nucleic acid to which they are operably linked. Such vectors are called "expression vectors" herein.

"Subject/patient sample" refers to a collection of cells or fluids obtained from a patient or subject. The source of the tissue or cell samples can be solid tissues, e.g., from fresh, frozen and/or preserved organ or tissue samples or biopsy samples or puncture samples; blood or any blood component; body fluids such as cerebrospinal fluids, amniotic fluids, peritoneal fluids, or interstitial fluids; cells from a subject at any time during pregnancy or development. Tissue samples may comprise compounds which are naturally not mixed with tissues, such as preservatives, anticoagulants, buffers, fixatives, nutrients, antibiotics, and the like. Examples of tumor samples include but are not limited to tumor biopsies, fine needle aspirates, bronchial lavage fluids, pleural fluids, sputa, urine, surgical specimens, circulating tumor cells, serum, plasma, circulating plasma proteins, ascites, primary cell cultures or cell lines derived from tumors or exhibiting tumor-like properties, and preserved tumor samples such as formalin-fixed, paraffin-embedded tumor samples or frozen tumors samples.

The term "package insert" is used to refer to the instructions generally contained in the commercial package of therapeutic products, which contain information about indications, usage, dosage, administration, combination therapies, contraindications and/or warnings related to the application of such therapeutic products.

Antibody of the Invention

Therefore, in some embodiments, the antibody or the fragment thereof of the invention binds to LAG-3. In some embodiments, the antibody or the fragment thereof of the invention binds to mammalian LAG-3, such as human LAG-3 or mouse LAG-3. For example, the antibody molecule specifically binds to an epitope (e.g., a linear or conformational epitope) of LAG-3. In some embodiments, the antibody molecule binds to one or more extracellular Ig-like domains of LAG-3 (e.g., the first, second, third, or fourth extracellular Ig-like domain of LAG-3).

In some embodiments, the anti-LAG-3 antibody or the fragment thereof of the invention has one or more of the following properties:

(1) the anti-LAG-3 antibody or fragment thereof of the invention binds to LAG-3 (e.g., human LAG-3) with high affinity, e.g., binds to LAG-3 with an equilibrium dissociation constant ($K_D$) of less than about 100 nM, preferably less than or equal to about 50 nM, particularly preferably less than or equal to about 20 nM, more preferably less than or equal to about 10 nM, 9 nM, 8 nM, 7 nM, 6 nM, 5 nM, 4 nM, 3 nM, or 2 nM, most preferably less than or equal to about 1 nM, 0.9 nM, 0.8 nM, or 0.7 nM. In some embodiments, the anti-LAG-3 antibody disclosed herein binds to LAG-3 with a $K_D$ of 0.1-20 nM, preferably 0.5-20 nM, more preferably 0.5-10 nM, 0.5-8 nM, or 0.5-5 nM, and most preferably 0.5-1 nM, 0.5-0.8 nM, 0.5-0.7 nM, or 0.6-0.7 nM. In some embodiments, the LAG-3 is human LAG-3. In some embodiments, the LAG-3 is mouse LAG-3. In some embodiments, the antibody binding affinity is determined using biological optical interferometry (e.g., ForteBio affinity assay).

(2) the antibody or the fragment thereof of the invention binds to cells expressing human LAG-3, for example, with an $EC_{50}$ of less than or equal to about 3.3 nM, 3 nM, 2 nM, 1.5 nM, 1.4 nM, 1.3 nM, 1.2 nM, 1.1 nM, 1 nM, 0.9 nM, 0.8 nM, 0.7 nM, 0.6 nM or 0.5 nM. In some embodiments, the binding is determined using flow cytometry (e.g., FACS). In some embodiments, the cells expressing human LAG-3 are 293 cells (e.g., HEK293 cells) expressing human LAG-3.

(3) the antibody or the fragment thereof of the invention binds to cells expressing mouse LAG-3, e.g., with an $EC_{50}$ of less than or equal to about 15000 nM, 14000 nM, or 13000 nM. In some embodiments, the antibody or fragment thereof of the invention binds to cells expressing mouse LAG-3, e.g., with an $EC_{50}$ of less than or equal to about 50 nM, e.g., an $EC_{50}$ of about 40-50 nM, about 40-45 nM, or about 42 nM. In some embodiments, the binding is determined using flow cytometry (e.g., FACS). In some embodiments, the cells expressing mouse LAG-3 are Chinese hamster ovary (CHO) cells expressing mouse LAG-3.

(4) the antibody or the fragment thereof of the invention inhibits relevant activities of LAG-3, e.g., with an $IC_{50}$ of less than or equal to about 20 nM, 10 nM, 9 nM, 8 nM, 7 nM, 6 nM, or 5 nM, preferably with an $IC_{50}$ of about 1-6 nM, 1-5 nM, 4 nM, 4.5 nM, 5 nM, 5.1 nM, 5.2 nM, 5.3 nM, 5.4 nM, 5.5 nM, 5.6 nM, 5.7 nM, 5.8 nM, 5.9 nM, or 6 nM. In some embodiments, the relevant activity of LAG-3 refers to the binding of MHC class II molecules to LAG-3. In some embodiments, the antibody or the fragment thereof of the invention inhibits the binding of LAG-3 to an MHC class II molecule on a cell expressing the MHC class II molecule with an $IC_{50}$ of less than or equal to about 20 nM, 10 nM, 9 nM, 8 nM, 7 nM, 6 nM, or 5 nM, preferably with an $IC_{50}$ of about 1-6 nM, 1-5 nM, 4 nM, 4.5 nM, 5 nM, 5.1 nM, 5.2 nM, 5.3 nM, 5.4 nM, 5.5 nM, 5.6 nM, 5.7 nM, 5.8 nM, 5.9 nM, or 6 nM. In some embodiments, the MHC class II molecule is HLA-DR. In some embodiments, the cell is a CHO cell. In some embodiments, the inhibition of relevant activities of LAG-3 by the antibody or the fragment thereof of the invention is measured using flow cytometry (e.g., FACS).

(5) the antibody or the fragment thereof of the invention binds to endogenous LAG-3 on the surface of activated CD4+ and/or CD8+ T cells, e.g., with an $EC_{50}$ of less than or equal to about 35 pM, 30 pM, 25 pM, 20 pM, 15 pM, 14 pM, or 13 pM, preferably with an $EC_{50}$ of about 1-20 pM, 5-20 pM, 5-15 pM, 10-15 pM, 11-13 pM, 10 pM, 11 pM, 12 pM, or 13 pM. In some embodiments, the activated CD4+ T cells are activated human CD4+ T cells. In some embodiments, the binding is determined by flow cytometry (e.g., FACS). In some embodiments, the flow cytometry is performed in an Accuri C6 system.

(6) the antibody or the fragment thereof of the invention inhibits one or more activities of LAG-3, e.g., resulting in one or more of the following: increased antigen-dependent stimulation of CD4+ T lymphocytes; increased T cell proliferation; increased expression of activating antigens (e.g., CD25); increased expression of cytokines (e.g., interferon-γ (IFN-γ), interleukin-2 (IL-2), or interleukin-4 (IL-4)); increased expression of chemokines (e.g., CCL3, CCL4, or CCL5); decreased suppressive activity of Treg cells; increased T-cell homeostasis; increased tumor-infiltrating lymphocytes; or reduced immune evasion of cancer cells.

(7) the anti-LAG-3 antibody or the fragment thereof of the invention may induce antibody-dependent cell-mediated cytotoxicity (ADCC).

In some embodiments, the anti-LAG-3 antibody or the antigen-binding fragment thereof of the invention has one or more of the following properties:

(i) showing identical or similar binding affinity and/or specificity for LAG-3 compared to the antibody of the invention (e.g., any of the antibodies listed in Table 3);

(ii) inhibiting (e.g., competitively inhibiting) the binding of the antibody of the invention (e.g., any of the antibodies listed in Table 3) to LAG-3;

(iii) binding to the same or overlapping epitope as the antibody of the invention (e.g., any of the antibodies listed in Table 3);

(iv) competing with the antibody of the invention (e.g., any of the antibodies listed in Table 3) for binding to LAG-3;

(v) having one or more biological characteristics of the antibody of the invention (e.g., any of the antibodies listed in Table 3).

Exemplary Antibodies

In some embodiments, the anti-LAG-3 antibody or the antigen-binding fragment thereof of the invention comprises a heavy chain variable region (VH), wherein the VH comprises:

(i) three complementarity determining regions (CDRs) contained in a VH of any of the antibodies listed in Table B, or (ii) relative to the sequence of (i), a sequence comprising a total of at least one and no more than 5, 4, 3, 2 or 1 amino acid alternations (preferably amino acid substitutions, and preferably conservative substitution) in the three CDR regions.

In some embodiments, the anti-LAG-3 antibody or the antigen-binding fragment thereof of the invention comprises a light chain variable region (VL), wherein the VL comprises:

(i) three complementarity determining regions (CDRs) contained in a VL of any of the antibodies listed in Table B, or (ii) relative to the sequence of (i), a sequence comprising a total of at least one and no more than 5, 4, 3, 2 or 1 amino acid alternations (preferably amino acid substitutions, and preferably conservative substitutions) in the three CDR regions.

In some embodiments, the anti-LAG-3 antibody or the antigen-binding fragment thereof of the invention comprises a heavy chain variable region VH and/or a light chain variable region VL, wherein (a) the VH comprises:

(i) three complementarity determining regions (CDRs) contained in a VH of any of the antibodies listed in Table B, or (ii) relative to the sequence of (i), a sequence comprising a total of at least one and no more than 5, 4, 3, 2 or 1 amino acid alternations (preferably amino acid substitutions, and preferably conservative substitutions) in the three CDR regions; and/or (b) the VL comprises:

(i) three complementarity determining regions (CDRs) contained in a VL of any of the antibodies listed in Table B, or (ii) relative to the sequence of (i), a sequence comprising a total of at least one and no more than 5, 4, 3, 2 or 1 amino acid alternations (preferably amino acid substitutions, and preferably conservative substitutions) in the three CDR regions.

In a preferred embodiment, the VH comprises or consists of an amino acid sequence selected from SEQ ID NOs: 22, 23, 24, and 25.

In a preferred embodiment, the VL comprises or consists of an amino acid sequence selected from SEQ ID NOs: 26, 27, 28, and 29.

In a preferred embodiment, the anti-LAG-3 antibody or the antigen-binding fragment thereof of the invention comprises: 3 complementarity determining regions (HCDRs) of heavy chain variable region set forth in SEQ ID NO: 22, 23, 24, or 25, and 3 complementarity determining regions (LCDRs) of light chain variable region set forth in SEQ ID NO: 26, 27, 28, or 29.

In some embodiments, the anti-LAG-3 antibody or the antigen-binding fragment thereof of the invention comprises a heavy chain variable region (VH) and/or a light chain variable region (VL), wherein (i) the VH comprises or consists of complementarity determining regions (CDRs) HCDR1, HCDR2 and HCDR3, wherein the HCDR1 comprises or consists of an amino acid sequence selected from SEQ ID NOs: 1, 2, 3, 4, and 17, or the HCDR1 comprises an amino acid sequence having one, two, or three alterations (preferably amino acid substitutions, and preferably conservative substitutions) compared to an amino acid sequence selected from SEQ ID NOs: 1, 2, 3, 4, and 17; the HCDR2 comprises or consists of an amino acid sequence selected from SEQ ID NOs: 5, 6, 7, and 18, or the HCDR2 comprises an amino acid sequence having one, two, or three alterations (preferably amino acid substitutions, and preferably conservative substitutions) compared to an amino acid sequence selected from SEQ ID NOs: 5, 6, 7, and 18; the HCDR3 comprises or consists of an amino acid sequence selected from SEQ ID NOs: 8, 9, 10, and 19, or the HCDR3 comprises an amino acid sequence having one, two, or three alterations (preferably amino acid substitutions, and preferably conservative substitutions) compared to an amino acid sequence selected from SEQ ID NOs: 8, 9, 10, and 19; and/or (ii) the VL comprises or consists of complementarity determining regions (CDRs) LCDR1, LCDR2 and LCDR3, wherein the LCDR1 comprises or consists of an amino acid sequence selected from SEQ ID NOs: 11, 12, and 20, or the LCDR1 comprises an amino acid sequence having one, two, or three alterations (preferably amino acid substitutions, and preferably conservative substitutions) compared to an amino acid sequence selected from SEQ ID NOs: 11, 12, and 20; the LCDR2 comprises or consists of an amino acid sequence selected from SEQ ID NO: 13, or the LCDR2 comprises an amino acid sequence having one, two, or three alterations (preferably amino acid substitutions, and preferably conservative substitutions) compared to an amino acid sequence selected from SEQ ID NO: 13; the LCDR3 comprises or consists of an amino acid sequence selected from SEQ ID NOs: 14, 15, 16, and 21, or the LCDR3 comprises an amino acid sequence having one, two, or three alterations (preferably amino acid substitutions, and preferably conservative substitutions) compared to an amino acid sequence selected from SEQ ID NOs: 14, 15, 16, and 21.

In a preferred embodiment, the invention provides an anti-LAG-3 antibody or an antigen-binding fragment thereof comprising a heavy chain variable region (VH) and/or a light chain variable region (VL), wherein (a) the VH comprises:

(i) a combination of HCDR1, HCDR2, and HCDR3 shown in Table A; or (ii) a variant of the HCDR combination of (i), comprising a total of at least one and no more than 5, 4, 3, 2, or 1 amino acid alterations (preferably amino acid substitutions, and preferably conservative substitutions) in the three CDR regions; and/or (b) the VL comprises:

(i) a combination of LCDR1, LCDR2 and LCDR3 shown in Table A; or (ii) a variant of the LCDR combination of (i), comprising a total of at least one and no more than 5, 4, 3, 2 or 1 amino acid alterations (preferably amino acid substitutions, and preferably conservative substitutions) in the three CDR regions.

In a preferred embodiment, the invention provides an anti-LAG-3 antibody or an antigen-binding fragment thereof comprising a heavy chain variable region (VH) and a light chain variable region (VL), wherein the VH comprises complementarity determining regions (CDRs) HCDR1, HCDR2, and HCDR3; the VL comprises complementarity determining regions (CDRs) LCDR1, LCDR2, and LCDR3; and combinations of HCDR1, HCDR2, HCDR3, LCDR1, LCDR2, and LCDR3 contained in the antibody or the antigen-binding fragment thereof are shown in the following table (Table A).

(iii) comprises an amino acid sequence having 1 or more (preferably not more than 10, and more preferably not more than 5, 4, 3, 2 or 1) amino acid alterations (preferably amino acid substitutions, and more preferably amino acid conservative substitutions) as compared to an amino acid sequence selected from SEQ ID NOs: 22, 23, 24, and 25, wherein preferably, the amino acid alterations do not occur in the CDRs; and/or (b) the light chain variable region VL (i) comprises or consists of an amino acid sequence having at least 90%, 91%, 92%, 93%, 94%, 95%, 96%, 97%, 98% or 99% identity with an amino acid sequence selected from SEQ ID NOs: 26, 27, 28, and 29;

(ii) comprises or consists of an amino acid sequence selected from SEQ ID NOs: 26, 27, 28, and 29; or (iii) comprises an amino acid sequence having 1 or more (preferably not more than 10, and more preferably not more than 5, 4, 3, 2, or 1) amino acid alterations (preferably amino acid substitutions, and more preferably amino acid conservative substitutions) as compared to an amino acid sequence selected from SEQ ID NOs: 26, 27, 28, and 29, wherein preferably, the amino acid alterations do not occur in the CDRs.

In a preferred embodiment, the invention provides an anti-LAG-3 antibody or an antigen-binding fragment thereof, comprising a heavy chain variable region (VH) and a light chain variable region (VL), wherein combinations of the heavy chain variable region VH and light chain variable region VL contained in the antibody or the antigen-binding fragment thereof are shown in the following table (Table B).

TABLE A

Exemplary combinations of HCDR1, HCDR2, HCDR3, LCDR1, LCDR2, and LCDR3 in the antibody or the antigen-binding fragment thereof of the invention

| Combinations | HCDR1, which comprises or consists of an amino acid sequence shown in the following SEQ ID NOs | HCDR2, which comprises or consists of an amino acid sequence shown in the following SEQ ID NOs | HCDR3, which comprises or consists of an amino acid sequence shown in the following SEQ ID NOs | LCDR1, which comprises or consists of an amino acid sequence shown in the following SEQ ID NOs | LCDR2, which comprises or consists of an amino acid sequence shown in the following SEQ ID NOs | LCDR3, which comprises or consists of an amino acid sequence shown in the following SEQ ID NOs |
|---|---|---|---|---|---|---|
| (1) | SEQ ID NO: 1 | SEQ ID NO: 5 | SEQ ID NO: 8 | SEQ ID NO: 11 | SEQ ID NO: 13 | SEQ ID NO: 14 |
| (2) | SEQ ID NO: 2 | SEQ ID NO: 6 | SEQ ID NO: 9 | SEQ ID NO: 11 | SEQ ID NO: 13 | SEQ ID NO: 15 |
| (3) | SEQ ID NO: 3 | SEQ ID NO: 7 | SEQ ID NO: 10 | SEQ ID NO: 12 | SEQ ID NO: 13 | SEQ ID NO: 16 |
| (4) | SEQ ID NO: 4 | SEQ ID NO: 7 | SEQ ID NO: 9 | SEQ ID NO: 11 | SEQ ID NO: 13 | SEQ ID NO: 16 |
| (5) | SEQ ID NO: 17 | SEQ ID NO: 18 | SEQ ID NO: 19 | SEQ ID NO: 20 | SEQ ID NO: 13 | SEQ ID NO: 21 |

In some embodiments, the anti-LAG-3 antibody or the antigen-binding fragment thereof of the invention comprises a heavy chain variable region VH and/or a light chain variable region VL, wherein (a) the heavy chain variable region VH (i) comprises or consists of an amino acid sequence having at least 90%, 91%, 92%, 93%, 94%, 95%, 96%, 97%, 98%, or 99% identity with an amino acid sequence selected from SEQ ID NOs: 22, 23, 24, and 25; or (ii) comprises or consists of an amino acid sequence selected from SEQ ID NOs: 22, 23, 24, and 25; or

TABLE B

Exemplary combinations of the heavy chain variable region VH and light chain variable region VL in the antibody or the antigen-binding fragment thereof of the invention

| Combinations | VH, which comprises or consists of an amino acid sequence shown in the following SEQ ID NOs | VL, which comprises or consists an amino acid sequence shown in the following SEQ ID NOs |
|---|---|---|
| (1) | SEQ ID NO: 22 | SEQ ID NO: 26 |
| (2) | SEQ ID NO: 23 | SEQ ID NO: 27 |

TABLE B-continued

Exemplary combinations of the heavy chain variable region VH and light chain variable region VL in the antibody or the antigen-binding fragment thereof of the invention

| Combinations | VH, which comprises or consists of an amino acid sequence shown in the following SEQ ID NOs | VL, which comprises or consists an amino acid sequence shown in the following SEQ ID NOs |
|---|---|---|
| (3) | SEQ ID NO: 24 | SEQ ID NO: 28 |
| (4) | SEQ ID NO: 25 | SEQ ID NO: 29 |

In some embodiments, the anti-LAG-3 antibody or the antigen-binding fragment thereof of the invention comprises a heavy chain and/or a light chain, wherein (a) the heavy chain
(i) comprises or consists of an amino acid sequence having at least 85%, 90%, 91%, 92%, 93%, 94%, 95%, 96%, 97%, 98% or 99% identity with an amino acid sequence selected from SEQ ID NOs: 30, 31, 32, and 33;
(ii) comprises or consists of an amino acid sequence selected from SEQ ID NOs: 30, 31, 32, and 33; or
(iii) comprises an amino acid sequence having 1 or more (preferably not more than 20 or 10, and more preferably not more than 5, 4, 3, 2, or 1) amino acid alterations (preferably amino acid substitutions, and more preferably amino acid conservative substitutions) as compared to an amino acid sequence selected from SEQ ID NOs: 30, 31, 32, and 33, wherein preferably, the amino acid alterations do not occur in the CDRs of the heavy chain, and more preferably, the amino acid alterations do not occur in the heavy chain variable region; and/or (b) the light chain
(i) comprises or consists of an amino acid sequence having at least 85%, 90%, 91%, 92%, 93%, 94%, 95%, 96%, 97%, 98% or 99% identity with an amino acid sequence selected from SEQ ID NOs: 34, 35, 36, and 37;
(ii) comprises or consists of an amino acid sequence selected from SEQ ID NOs: 34, 35, 36, and 37; or
(iii) comprises an amino acid sequence having 1 or more (preferably not more than 20 or 10, and more preferably not more than 5, 4, 3, 2, or 1) amino acid alterations (preferably amino acid substitutions, and more preferably amino acid conservative substitutions) as compared to an amino acid sequence selected from SEQ ID NOs: 34, 35, 36, and 37, wherein preferably, the amino acid alterations do not occur in the CDRs of the light chain, and more preferably, the amino acid alterations do not occur in the light chain variable region.

In a preferred embodiment, the invention provides an anti-LAG-3 antibody or an antigen-binding fragment thereof, comprising a heavy chain and a light chain, wherein combinations of the heavy and light chains contained in the antibody or the antigen-binding fragment thereof are shown in the following table (Table C).

TABLE C

Exemplary combinations of the heavy chain and light chain in the antibody or the antigen-binding fragment thereof of the invention

| Combinations | Heavy chain, which comprises or consists of an amino acid sequence shown in the following SEQ ID NOs | Light chain, which comprises or consists of an amino acid sequence shown in the following SEQ ID NOs |
|---|---|---|
| (1) | SEQ ID NO: 30 | SEQ ID NO: 34 |
| (2) | SEQ ID NO: 31 | SEQ ID NO: 35 |
| (3) | SEQ ID NO: 32 | SEQ ID NO: 36 |
| (4) | SEQ ID NO: 33 | SEQ ID NO: 37 |

In some embodiments, the heavy chain and/or light chain of the anti-LAG-3 antibody or the fragment thereof disclosed herein further comprises a signal peptide sequence, such as METDTLLLWVLLLWVPGSTG (SEQ ID NO: 48).

In one embodiment of the invention, the amino acid alteration described herein includes amino acid substitution, insertion, or deletion. Preferably, the amino acid alteration described herein is amino acid substitution, and preferably conservative substitution.

In a preferred embodiment, the amino acid alteration described herein occurs in a region outside the CDR (e.g., in FR). More preferably, the amino acid alteration described herein occurs in a region outside the heavy chain variable region and/or outside the light chain variable region.

Optionally, the anti-LAG-3 antibody of the invention comprises post-translational modifications to the light chain variable region, the heavy chain variable region, the light chain, or the heavy chain.

Exemplary post-translational modifications include disulfide bond formation, glycosylation, lipidation, acetylation, phosphorylation, or any other operations, such as conjugation with a labeling component.

In some embodiments, the substitution is a conservative substitution. A conservative substitution refers to the replacement of an amino acid by another amino acid of the same class, e.g., the replacement of an acidic amino acid by another acidic amino acid, the replacement of a basic amino acid by another basic amino acid, or the replacement of a neutral amino acid by another neutral amino acid. Exemplary substitutions are shown in Table D below.

TABLE D

| Original residue | Exemplary substitution | Preferred substitution |
|---|---|---|
| Ala (A) | Val; Leu; Ile | Val |
| Arg (R) | Lys; Gln: Asn | Lys |
| Asn(N) | Gln; His: Asp, Lys: Arg | Gln |
| Asp(D) | Glu; Asn | Glu |
| Cys(C) | Ser: Ala | Ser |
| Gln(Q) | Asn: Glu | Asn. |
| Glu(E) | Asp: Gln | Asp |
| Gly(G) | Ala | Ala |
| His(H) | Asn; Gln; Lys: Arg | Arg |
| Ile(I) | Leu; Val; Met; Ala; Phe; Nle | Leu |
| Leu(L) | Nle; Ile; Val; Met: Ala; Phe | Ile |
| Lys(K) | Arg: Gln; Asn | Arg |
| Met(M) | Lceu: Phe: Ile | Leu |
| Phe(F) | Trp: Leu; Val; Ile: Ala: Tyr | Tyr |
| Pro(P) | Ala | Ala |
| Ser(S) | Thr | Thr |
| Thr(T) | Val; Ser | Ser |
| Trp(W) | Tyr: Phe | Tyr |
| Tyr(Y) | Trp; Phe; Thr; Ser | Phe |
| Val(V) | Le: Leu: Met: Phe: Ala; Nle | Leu |

In certain embodiments, the antibody provided herein is altered to increase or decrease the extent to which the antibody is glycosylated. Addition or deletion of glycosylation sites to an antibody can be conveniently achieved by altering the amino acid sequence such that one or more glycosylation sites are created or removed.

For example, one or more amino acid substitutions can be performed to eliminate one or more variable region framework glycosylation sites, thereby eliminating glycosylation at that site. Such aglycosylation can increase the affinity of an antibody to an antigen. See, e.g., U.S. Pat. Nos. 5,714,350 and 6,350,861. Antibodies with altered classes of glycosylation can be prepared, such as low-fucosylated antibodies with reduced amounts of fucosyl residues or antibodies with increased bisecting GlcNac structures. Such altered glycosylation patterns have shown the ability to increase ADCC of antibodies. Such carbohydrate modifications can be achieved by, e.g., expressing antibodies in host cells with altered glycosylation systems. Cells with altered glycosylation systems have been described in the art and can be used as host cells in which the antibodies of the invention are expressed to thereby produce antibodies with altered glycosylation. For example, cell lines Ms704, Ms705, and Ms709 lack the fucosyltransferase gene FUT8 (alpha-(1,6)-fucosyltransferase), such that antibodies expressed in cell lines Ms704, Ms705, and Ms709 lack fucose in their carbohydrates. Cell lines Ms704, Ms705, and Ms709 FUT8−/− are created by the targeted disruption of the FUT8 gene in CHO/DG44 cells using two replacement vectors (see US Patent Publication No. 20040110704 and Yamane-Ohnuki et al. (2004) Biotechnol Bioeng 87: 614-22). EP 1,176,195 describes cell lines with a functionally disrupted FUT8 gene encoding a fucosyltransferase, such that antibodies expressed in the cell lines exhibit low fucosylation by reducing or eliminating α-1,6 bond-related enzymes. EP 1,176,195 also describes cell lines with low or no enzymatic activity which adds fucose to N-acetylglucosamine binding to Fc regions of an antibody, such as rat myeloma cell line YB2/0 (ATCC CRL 1662). PCT publication WO 03/035835 describes a variant CHO cell line Lec13 cells, in which the ability of attaching fucose to Asn (297)-linked carbohydrates is reduced, thereby also leading to low fucosylation of antibodies expressed in the host cell (see also Shields et al. (2002) J. Biol. Chem. 277: 26733-26740). Antibodies with modified glycosylation profiles can also be produced in eggs, as described in PCT publication WO 06/089231. Alternatively, antibodies with modified glycosylation profiles can be produced in plant cells, such as *Lemna*. A method for producing antibodies in plant systems is disclosed in a US patent application filed on Aug. 11, 2006, corresponding to Alston and Bird LLP. Attorney Docket No. 040989/314911. PCT publication WO 99/54342 describes a cell line engineered to express a glycoprotein modifying glycosyltransferase (such as β(1,4)-N-acetylglucosaminyltransferase III (GnTIII)), and thereby antibodies expressed in the engineered cell line exhibit increased bisecting GlcNac structures, which results in increased ADCC activity of the antibody (see also Umana et al. (1999) Nat. Biotech. 17:176-180). Alternatively, fucosidase can be used to cut fucosyl residues off the antibody; for example, α-L-fucosidase removes fucosyl residues from the antibody (Tarentino et al. (1975) Biochem. 14:5516-23).

In one embodiment of the invention, the antibody or the fragment of the invention is glycosylated with an engineered yeast N-linked glycan or CHO N-linked glycan.

Another modification encompassed by the invention to the antibody or the fragment thereof described herein is PEGylation. An antibody can be PEGylated to, e.g. increase the biological (e.g., serum) half-life of the antibody. To PEGylate an antibody, the antibody or the fragment thereof typically reacts with polyethylene glycol (PEG) (such as a reactive ester or aldehyde derivative of PEG) in a condition where one or more PEG groups become attached to the antibody or antibody fragment. Preferably, PEGylation is performed via an acylation reaction or an alkylation reaction using a reactive PEG molecule (or a similar reactive water-soluble polymer). As used herein, the term "polyethylene glycol" is intended to encompass any form of PEG which has been used to derivatize other proteins, such as mono (C1-C10) alkoxy- or aryloxy polyethylene glycol or polyethylene glycol-maleimide. In certain embodiments, the antibody to be PEGylated is an aglycosylated antibody. Methods for PEGylation of proteins are known in the art and can be applied to the antibody of the invention, for example, see EP 0154316 and EP 0401384. In certain embodiments, one or more amino acid modifications can be introduced into an Fc region of an antibody provided herein, thereby producing an Fc region variant such that, for example, the efficacy of the antibody in treating cancer or a cell proliferative disease is enhanced. The anti-LAG-3 antibody and the antigen-binding fragment thereof disclosed herein also include antibodies and fragments having modified (or closed) Fc regions to provide altered effector functions. See, e.g., U.S. Pat. No. 5,624,821, WO2003/086310, WO2005/120571, WO2006/0057702. Such modifications can be used to enhance or suppress various responses of the immune system and may have beneficial effects in diagnosis and treatment. Modifications of the Fc region include amino acid alteration (substitution, deletion and insertion), glycosylation or deglycosylation, and addition of multiple Fc. Modifications to Fc can also alter the half-life of the antibody in the therapeutic antibodies, thereby enabling less frequent administrations, and the resulting increased convenience and reduced material use. See Presta (2005) J. Allergy Clin. Immunol. 116:731, pages 734-735.

In one embodiment, the number of cysteine residues of an antibody can be altered to modify antibody properties. For example, the hinge region of CH1 is modified to change (e.g., increase or decrease) the number of cysteine residues in the hinge region. This method is further described in U.S. Pat. No. 5,677,425. The number of cysteine residues in the hinge region of CH1 can be changed to, e.g., facilitate assembly of the light and heavy chains, or increase or decrease the stability of the antibody.

In certain embodiments, the antibodies provided herein can be further modified to contain other non-protein portions known in the art and readily available. Suitable portions for antibody derivatization include, but are not limited to, water-soluble polymers. Non-limiting examples of water-soluble polymers include, but are not limited to, polyethylene glycol (PEG), ethylene glycol/propylene glycol copolymers, carboxymethyl cellulose, dextran, polyvinyl alcohol, polyvinylpyrrolidone, poly-1,3-dioxane, poly-1,3,6-trioxane, ethylene/maleic anhydride copolymer, polyamino acid (homopolymer or random copolymer), and dextran or poly(n-ethylene methylpyrrolidone) polyethylene glycol, propylene glycol homopolymer, polypropylene oxide/ethylene oxide copolymer, polyoxyethylated polyol (such as glycerol), polyvinyl alcohol, and mixtures thereof. The polymer may have any molecular weight and may be branched or unbranched. The number of polymers attached to the antibody can vary, and if more than one polymer is attached, they can be the same or different molecules. In general, the number and/or type of polymers used for derivatization can be determined based on considerations including, but not limited to, the specific characteristics or functions of the antibody to be improved, whether the antibody derivative will be used in therapy in defined conditions, etc.

In some embodiments, the invention involves fragments of the anti-LAG-3 antibodies. Examples of antibody fragments include, but are not limited to, Fv, Fab, Fab', Fab'-SH, F(ab')$_2$, a diabody, a linear antibody, a single-chain variable fragment (e.g., scFv), and a bispecific antibody formed from the antibody fragments.

For example, the antibody molecule may comprise a heavy chain (HC) variable domain sequence and a light chain (LC) variable domain sequence. In one embodiment, the antibody molecule (referred to herein as an incomplete antibody) comprises or consists of a heavy chain and a light chain. In another example, the antibody molecule comprises two heavy chain variable domain sequences and two light chain variable domain sequences, thereby forming two antigen-binding sites, such as Fab, Fab', F(ab')$_2$, Fc, Fd, Fd', Fv, a single-chain variable fragment (e.g., scFv), a single-domain antibody, a diabody (Dab) (bivalent and bispecific), and a chimeric (e.g., humanized) antibody, which can be generated by modifying intact antibodies or synthesized de novo using the recombinant DNA technology. These functional antibody fragments retain the ability to selectively bind to their corresponding antigens or receptors. Antibodies and antibody fragments can be from any antibody class, including but not limited to, IgG, IgA, IgM, IgD, and IgE, and from any antibody subclass (e.g., IgG1, IgG2, IgG3, and IgG4). The preparation of antibody molecules can be monoclonal or polyclonal. The antibody may be a human antibody, a humanized antibody, a chimeric antibody, a CDR-grafted antibody, or an antibody produced in vitro. The antibody may have, e.g., a heavy chain constant region selected from IgG1, IgG2, IgG3, and IgG4. The antibody may also have a light chain selected from, e.g., kappa and lambda.

The antibody of the invention may also be a single-domain antibody. The single-domain antibody can include antibody whose complementarity determining regions are part of a single-domain polypeptide. Examples include, but are not limited to, heavy chain antibodies, antibodies naturally devoid of light chains, single-domain antibodies or engineered antibodies derived from conventional 4-chain antibody. The single-domain antibody can be any antibody of the prior art, or any single-domain antibody in the future. The single-domain antibody can be derived from any species, including but not limited to, mouse, human, camel, alpaca, fish, shark, goat, rabbit, and cattle. According to another aspect of the invention, the single-domain antibody is a naturally-occurring single-domain antibody, which is referred to as a heavy chain antibody devoid of light chains. Such single-domain antibodies are disclosed, e.g., in WO 94/04678. A single-domain antibody or nanobody can be an antibody produced from camelidae species, such as camel, alpaca, dromedary, llama, and guanaco. Species other than camel can produce heavy chain antibodies naturally devoid of light chains; such single-domain antibodies are within the scope of the invention.

In some embodiments, the anti-LAG-3 antibody of the invention is a humanized antibody. Different methods for humanizing antibodies are known to those skilled, as summarized by Almagro and Fransson, the contents of which are incorporated herein in their entireties by reference (Almagro J. C. and Fransson J (2008) Frontiers in Bioscience 13: 1619-1633). Almagro & Fransson distinguishes between rational approach and empirical approach. The rational approach is characterized by generating a small number of engineered antibody variants and assessing their binding or any other characteristics of interest. If variants of the design do not produce the expected results, a new round of design and integration evaluation starts. The rational approach includes CDR grafting, resurfacing, superhumanization, and human string content optimization. In contrast, the empirical method is based on generating large humanized variant libraries, and selects the best clones using enrichment techniques or high-throughput screening. Thus, the empirical approach depends on a reliable selection and/or screening system capable of searching a large number of antibody variants. In vitro display technologies such as phage display and ribosome display meet these requirements and are well known to those skilled. The Empirical approach includes FR library construction, guided selection, framework-shuffling, and humaneering.

In some embodiments, the anti-LAG-3 antibody of the invention is a human antibody. The human antibody can be prepared through a variety of techniques known in the art. The human antibody is generally described in van Dijk and van de Winkel, Curr. Opin. Pharmacol 5: 368-74 (2001) and Lonberg, Curr. Opin. Immunol 20: 450-459 (2008). For example, a transgenic mouse carrying human immunoglobulin genes rather than a mouse system can be used for producing human monoclonal antibodies (see, e.g., Wood et al., International Application WO 91/00906; Kucherlapati et al., PCT Publication WO 91/10741; Lonberg et al., International Application WO 92/03918; Kay et al., International Application 92/03917; Lonberg, N. et al., 1994 Nature 368: 856-859; Green, L. L. et al., 1994 Nature Genet. 7: 13-21; Morrison, S. L. et al., 1994 Proc. Natl. Acad. Sci. USA 81: 6851-6855; Bruggeman et al., 1993 Year Immunol 7: 33-40; Tuaillon et al., 1993 PNAS 90: 3720-3724; and Bruggeman et al., 1991 Eur J Immunol 21: 1323-1326).

In some embodiments, the anti-LAG-3 antibody disclosed herein is a non-human antibody, such as a rodent (mouse or rat) antibody, a goat antibody, a primate (e.g., monkey) antibody, and a camel antibody. Preferably, the non-human antibody is a rodent (mouse or rat) antibody. A method for producing the rodent antibody is known in the art.

The antibody of the invention can be isolated by screening a combinatorial library for antibodies having desired activities. For example, various methods are known in the art for generating phage display libraries and screening the libraries for the antibodies with desired binding characteristics. These methods are described in, for example, Hoogenboom et al., Methods in Molecular Biology 178: 1-37 (compiled by 0' Brien et al., Human Press, Totowa, N.J., 2001), and further described in, for example, McCafferty et al., Nature 348: 552-554; Clackso et al., Nature 352: 624-628 (1991); Marks et al., J. Mol. Biol. 222: 581-597 (1992); Marks and Bradbury, Methods in Molecular Biology 248: 161-175 (compiled by Lo, Human Press, Totowa, N.J., 2003); Sidhu et al., J. Mol. Biol. 338 (2): 299-310 (2004); Lee et al., J. Mol. Biol 340 (5): 1073-1093 (2004); Fellouse, Proc. Natl. Acad. Sci. USA 101 (34): 12467-12472 (2004); and Lee et al., J. Immunol. Methods 284 (1-2): 119-132 (2004).

In one embodiment, the antibody molecule is a monospecific antibody molecule and binds to a single epitope. For example, the monospecific antibody molecule includes a plurality of immunoglobulin variable domain sequences that each binds to the same epitope.

In one embodiment, the antibody molecule is a multispecific antibody molecule, for example, the antibody molecule comprises a plurality of immunoglobulin variable domain sequences, wherein a first immunoglobulin variable domain sequence of the plurality of immunoglobulin variable domain sequences has binding specificity for a first epitope, and a second immunoglobulin variable domain sequence of the plurality of immunoglobulin variable domain sequences has binding specificity for a second epitope. In one embodiment, the first and second epitopes are on the same antigen (e.g., the same protein or the same subunit of a multimeric protein). In one embodiment, the first and second epitopes overlap. In one embodiment, the first and second epitopes do not overlap. In one embodiment, the first and second epitopes are located on different antigens (e.g., different proteins or different subunits of a multimeric protein). In one embodiment, the multispecific antibody molecule comprises a third, fourth or fifth immunoglobulin variable domain. In one embodiment, the multispecific antibody molecule is a bispecific antibody molecule or a trispecific antibody molecule or a tetraspecific antibody molecule. In one embodiment, the multispecific antibody molecule is a bispecific antibody molecule. A bispecific antibody is specific for no more than two antigens. A bispecific antibody molecule is characterized by a first immunoglobulin variable domain sequence having binding specificity for a first epitope and a second immunoglobulin variable domain sequence having binding specificity for a second epitope. In one embodiment, the first and second epitopes are on the same antigen (e.g., the same protein or the same subunit of a multimeric protein). In one embodiment, the first and second epitopes overlap. In one embodiment, the first and second epitopes do not overlap. In one embodiment, the first and second epitopes are located on different antigens (e.g., different proteins or different subunits of a multimeric protein). In one embodiment, a bispecific antibody molecule comprises heavy and light chain variable domain sequences having binding specificity for a first epitope, and heavy and light chain variable domain sequences having binding specificity for a second epitope. In one embodiment, a bispecific antibody molecule comprises an incomplete antibody having binding specificity for a first epitope, and an incomplete antibody having binding specificity for a second epitope. In one embodiment, a bispecific antibody molecule comprises an incomplete antibody or a fragment thereof having binding specificity for a first epitope, and an incomplete antibody or a fragment thereof having binding specificity for a second epitope. In one embodiment, a bispecific antibody molecule comprises an scFv or a fragment thereof having binding specificity for a first epitope, and an scFv or a fragment thereof having binding specificity for a second epitope. In one embodiment, the first epitope is on LAG-3 and the second epitope is on PD-1, TIM-3, CEACAM (e.g., CEACAM-1 and/or CEACAM-5), PD-L1, or PD-L2. In a preferred embodiment, the second epitope is on PD-1.

In some embodiments, the antibody disclosed herein can be a chimeric antibody (e.g., a human constant domain/mouse variable domain). "chimeric antibody" as used herein is an antibody having a variable domain from a first antibody and a constant domain from a second antibody, wherein the first and second antibodies are from different species (U.S. Pat. No. 4,816,567; and Morrison et al. (1984) Proc. Natl. Acad. Sci. USA 81: 6851-6855). Typically, the variable domain is derived from an antibody ("parent antibody") of an experimental animal, such as a rodent, and the constant domain sequence is derived from a human antibody, so that the resulting chimeric antibody is less likely to cause an adverse immune response in a human subject than the parent (e.g., mouse) antibody.

In some embodiments, the invention further provides an anti-LAG-3 monoclonal antibody (an "immunoconjugate") conjugated to other substances, e.g., a therapeutic module or marker, such as a cytotoxic agent or an immunomodulatory agent. The cytotoxic agent includes any agent that is harmful to cells. Examples of cytotoxic agents (e.g. a chemotherapeutic agent) suitable for forming the immunoconjugate are known in the art, see, e.g. WO 05/103081, WO 2015/138920 or CN 107001470 A. For example, the cytotoxic agent includes, but is not limited to, radioisotopes, e.g., iodine ($^{131}$I or $^{125}$I), yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), indium ($^{111}$In), technetium ($^{99m}$Tc), phosphorus ($^{32}$P), rhodium ($^{188}$Rh), sulfur ($^{35}$S), carbon ($^{14}$C), tritium ($^{3}$H), chromium ($^{51}$Cr), chlorine ($^{36}$Cl), cobalt ($^{57}$Co or $^{58}$Co), iron ($^{59}$Fe), selenium ($^{75}$Se), or gallium ($^{67}$Ga). Examples of cytotoxic agents further include chemotherapeutic agents or other therapeutic agents, such as taxol, cytochalasin B, gramicidin D, ethidium bromide, emetine, mitomycin, etoposide, teniposide, vincristine, vinblastine, colchicine, doxorubicin, daunomycin, dihydroxyanthracine diketone, mitoxantrone, mithramycin, actinomycin D, 1-dehydrotestosterone, glucocorticoids, procaine, tetracaine, lidocaine, propranolol, puromycin, maytansinoids, such as maytansinol (see U.S. Pat. No. 5,208,020), and CC-1065 (see U.S. Pat. Nos. 5,475,092, 5,585,499, and 5,846,545), and analogs or homologs thereof. In addition, cytotoxic agents include, for example, antimetabolites (e.g., methotrexate, 6-mercaptopurine, 6-thioguanine, cytarabine, 5-fluorouracil, and dacarbazine); alkylating agents (e.g., mechlorethamine, thioephaloramucil, CC-1065, melphalan, carmustine (BSNU), lomustine (CCNU), cyclophosphamide, busulfan, dibromomannitol, streptozotocin, mitomycin C, and cis-dichlorodiamineplatinum (II) (DDP) cisplatin); anthracyclines (e.g., daunorubicin (formerly known as daunomycin) and doxorubicin); antibiotics (e.g., dactinomycin (formerly known as actinomycin D), bleomycin, mithramycin, and anthramycin (AMC)); antimitotics (e.g., vincristine, vinblastine, taxol, and maytansinoids); growth inhibitors; enzymes and fragments thereof, such as nucleic acid hydrolases; antibiotics; toxins (e.g., small-molecule toxins or enzymatically active toxins of bacterial, fungal, plant, or animal origin) and fragments and/or variants thereof; and various known antitumor or anticancer agents.

Nucleic Acid of the Invention and Host Cell Comprising Same

In one aspect, the present invention provides a nucleic acid encoding any of the above anti-LAG-3 antibodies or a fragment thereof. The nucleic acid can encode an amino acid sequence comprising the light chain variable region and/or the heavy chain variable region of the antibody, or an amino acid sequence comprising the light chain and/or the heavy chain of the antibody.

For example, the exemplary nucleic acid disclosed herein comprises a nucleic acid sequence selected from SEQ ID NOs: 38, 39, 40, 41, 42, 43, 44 and 45 or a nucleic acid sequence having at least 85%, 90%, 91%, 92%, 93%, 94%, 95%, 96%, 97%, 98%, or 99% identity with the nucleic acid sequence selected from SEQ ID NOs: 38, 39, 40, 41, 42, 43, 44 and 45. For example, the nucleic acid disclosed herein comprises a nucleic acid encoding an amino acid sequence selected from any one of SEQ ID NOs: 22, 23, 24, 25, 26, 27, 28, 29, 30, 31, 32, 33, 34, 35, 36, and 37, or a nucleic acid encoding an amino acid sequence having at least 85%, 90%, 91%, 92%, 93%, 94%, 95%, 96%, 97%, 98%, or 99% identity with the amino acid sequence selected from any one of SEQ ID NOs: 22, 23, 24, 25, 26, 27, 28, 29, 30, 31, 32, 33, 34, 35, 36 and 37.

The invention further provides a nucleic acid that is hybridized under a stringent condition with the following nucleic acid, or a variation of the following nucleic acid having one or more substitutions (e.g., conservative substitutions), deletions or insertions: a nucleic acid comprising a nucleic acid sequence having at least 85%, 90%, 91%, 92%, 93%, 94%, 95%, 96%, 97%, 98%, or 99% identity with a nucleic acid sequence selected from SEQ ID NOs: 38, 39, 40, 41, 42, 43, 44 and 45, or a nucleic acid comprising the nucleic acid sequence selected from SEQ ID NOs: 38, 39, 40, 41, 42, 43, 44 and 45; or a nucleic acid comprising a nucleic acid sequence encoding an amino acid sequence selected from any one of SEQ ID NOs: 22, 23, 24, 25, 26, 27, 28, 29, 30, 31, 32, 33, 34, 35, 36, and 37, or a nucleic acid comprising a nucleic acid sequence encoding an amino acid sequence having at least 85%, 90%, 91%, 92%, 93%, 94%, 95%, 96%, 97%, 98%, or 99% identity with the amino acid sequence selected from any one of SEQ ID NOs: 22, 23, 24, 25, 26, 27, 28, 29, 30, 31, 32, 33, 34, 35, 36 and 37.

In one embodiment, one or more vectors containing the nucleic acid are provided. In one embodiment, the vector is an expression vector, such as an eukaryotic expression vector. The vector includes, but is not limited to, a virus, a plasmid, a cosmid, a lambda phage, or a yeast artificial chromosome (YAC). Numerous vector systems can be used. For example, one class of vectors utilize DNA elements derived from animal viruses such as bovine papillomaviruses, polyomaviruses, adenoviruses, vaccinia virus, baculoviruses, retroviruses (Rous sarcoma viruses, MMTV, or MOMLV), and SV40 viruses. Another class of vectors utilize RNA elements derived from RNA viruses such as Semliki Forest viruses, eastern equine encephalitis viruses, and flaviviruses. In a preferred embodiment, the expression vector of the present invention is a pTT5 expression vector.

Additionally, cells having stably incorporated DNA in chromosomes thereof can be selected by introducing one or more markers permitting the selection of transfected host cells. The markers may, for example, provide prototrophy, biocidal (e.g., antibiotics) resistance, or heavy metal (e.g., copper) resistance, etc., for an auxotrophic host. Selectable marker genes may be linked directly to a DNA sequence to be expressed or introduced through co-transformation into the same cell. Additional elements may also be required for optimal synthesis of mRNA. The elements may include splicing signals, transcriptional promoters, enhancers, and termination signals.

Once the expression vector or DNA sequence has been prepared for expression, the expression vector can be transfected or introduced into suitable host cells. Various techniques can be used for this purpose, for example, protoplast fusion, calcium phosphate precipitation, electroporation, retroviral transduction, viral transfection, biolistics, lipid-based transfection, or other conventional techniques. In the case of protoplast fusion, cells are incubated in a culture medium and screened for appropriate activity. Methods and conditions for incubating the resulting transfected cell and for isolating the resulting antibody molecules are known to those skilled in the art and may be varied or optimized according to the particular expression vector and the particular mammalian host cell used based on the present description and methods known in the art.

In one embodiment, a host cell containing a nucleic acid encoding the antibody molecule described herein or the vector described herein is provided. Suitable host cells for cloning or expressing the nucleic acid encoding the antibody or the vector include prokaryotic or eukaryotic cells as described herein. For example, antibodies can be produced in bacteria, particularly when glycosylation and Fc effector functions are not required. Expression of an antibody fragment and a polypeptide in bacteria is described in, for example, U.S. Pat. Nos. 5,648,237, 5,789,199 and 5,840,523, and also described in Charlton, Methods in Molecular Biology, Vol. 248 (B. K. C. Lo, ed., Humana Press, Totowa, N.J., 2003), pg. 245-254, which describes expression of antibody fragments in E. coli. After expression, the antibody can be isolated from bacterial paste in soluble fraction and can be further purified. In one embodiment, the host cell is E. coli. In one embodiment, the host cell is eukaryotic. In another embodiment, the host cell is selected from a yeast cell, a mammalian cell (e.g., a human cell), an insect cell, a plant cell, or other cells suitable for preparation of the antibody or the antigen-binding fragment thereof. For example, eukaryotic microorganisms, such as filamentous fungi or yeast, are suitable cloning or expression hosts for the vector encoding the antibody, including fungus and yeast strains in which a glycosylation pathway has been "humanized" and thus resulting in production of an antibody having a partially or fully human glycosylation pattern, see Gerngross, Nat. Biotech. 22: 1409-1414 (2004), and Li et al., Nat. Biotech. 24: 210-215 (2006). Host cells suitable for expressing a glycosylated antibody are also derived from multicellular organisms (invertebrates and vertebrates). Vertebrate cells may also be used as hosts. For example, a mammalian cell line engineered to be suitable for suspension growth may be used. Other examples of useful mammalian host cell lines are monkey kidney CV1 lines (COS-7) transformed with SV40, human embryonic kidney lines (293 HEK or 293 cells, as described in, e.g., Graham et al., J. Gen Virol. 36: 59 (1977)) and the like. Other useful mammalian host cell lines include Chinese hamster ovary (CHO) cells including DHFR-CHO cells (Urlaub et al., Proc. Natl. Acad. Sci. USA 77: 216 (1980)), and myeloma cell lines such as Y0, NS0, and Sp2/0. Reviews of certain mammalian host cell lines suitable for antibody production can be seen from, e.g., Yazaki and Wu, Methods in Molecular Biology, Vol. 248 (B. K. C. Lo, ed., Humana Press, Totowa, N.J.), pg. 255-268 (2003). Other useful host cells include, but are not limited to, Vero cells, Hela cells, COS cells, CHO cells, HEK293 cells, BHK cells, MDCKII cells, PerC6 cell lines (e.g., PERC6 cells from Crucell), oocytes, and cells from transgenic animals, such as mammary epithelial cells. Suitable insect cells include, but are not limited to, Sf9 cells.

Method for Preparing the Antibody and the Antigen-Binding Fragment Thereof of the Invention The anti-LAG-3 antibody disclosed herein can be recombinantly produced. There are several methods known in the art for the production of recombinant antibodies. An example of methods for recombinant production of antibodies is disclosed in U.S. Pat. No. 4,816,567.

In one embodiment, a method for preparing an anti-LAG-3 antibody is provided, wherein the method comprises culturing host cells containing an nucleic acid encoding the antibody, as provided above, under conditions suitable for expressing the antibody, and optionally, isolating the antibody from the host cells (or host cell culture mediums). For recombinant production of the anti-LAG-3 antibody, a nucleic acid encoding the antibody (e.g., the antibody described above) is isolated and inserted into one or more vectors for further cloning and/or expression in the host cells. The nucleic acid is readily isolated and sequenced by using conventional procedures (e.g., by using oligonucleotide probes that are capable of binding specifically to genes encoding heavy and light chains of antibodies).

In one embodiment, the host cell contains a vector comprising a nucleic acid encoding an amino acid sequence of a VL of the antibody and a nucleic acid encoding an amino acid sequence of a VH of the antibody. In one embodiment, the host cell contains a first vector comprising a nucleic acid encoding an amino acid sequence of a VL of the antibody and a second vector comprising a nucleic acid encoding an amino acid sequence of a VH of the antibody.

Assay

The anti-LAG-3 antibody provided herein can be identified, screened, or characterized for its physical/chemical properties and/or biological activity through a variety of assays known in the art. In one aspect, the antigen-binding activity of the antibody of the invention is tested, for example, by known methods such as ELISA, Western blotting, flow cytometry, and magnetic beads coated with antibody molecules. LAG-3 binding can be determined by methods known in the art, and exemplary methods are disclosed herein. In some embodiments, a biological optical interferometry (e.g., Fortebio affinity assay), MSD assay, or flow cytometry is used.

In another aspect, a competitive binding assay can be used for identifying antibodies that compete for binding to LAG-3 with any of the anti-LAG-3 antibodies disclosed herein. In some embodiments, such competitive antibodies bind to the same epitope (e.g., a linear or conformational epitope) as any of the anti-LAG-3 antibodies disclosed herein. A detailed exemplary method for locating an antibody binding epitope is described in Morris (1996) "Epitope Mapping Protocols", Methods in Molecular Biology vol. 66 (Humana Press, Totowa, N.J.).

The invention further provides an assay for identifying an anti-LAG-3 antibody having one or more of the properties described above. Further provided is an antibody having such biological activities in vivo and/or in vitro.

In some embodiments, the antibody of the invention is tested for one or more of the properties described above.

Cells for use in any of said in-vitro assays include cells or cell lines that naturally express LAG-3 or are engineered to express LAG-3. Several cells express LAG-3. For example, LAG-3 is expressed on activated CD4+ and CD8+ T cells, Treg cells, natural killer (NK) cells, and plasmacytoid dendritic cells (DCs). LAG-3 is expressed in tumor-infiltrating lymphocytes, such as infiltrating lymphocytes in head and neck squamous cell carcinoma (HNSCC). LAG-3 is expressed on highly suppressive, inducible and natural Tregs. For example, highly suppressive FoxP3+nTregs and FoxP3-iTregs are positive for LAG-3 in melanoma and colorectal cancer (Camisaschi et al. (2010) J. Immunol. 184 (11): 6545-6551; Scurr et al. (2014) Mucosal. Immunol. 7 (2): 428-439). Such cells also include cell lines that express LAG-3 and cell lines that do not normally express LAG-3 but have been transfected with a nucleic acid encoding LAG-3.

It will be appreciated that any of said assays can be performed by using the immunoconjugate of the invention in place of or in addition to the anti-LAG-3 antibody.

It will be appreciated that any of said assays can be performed by using the anti-LAG-3 antibody and other therapeutic agents.

Pharmaceutical Composition and Pharmaceutical Preparation

The invention further provides a composition (including a pharmaceutical composition or a pharmaceutical preparation) comprising an anti-LAG-3 antibody or a fragment or an immunoconjugate thereof, and a composition comprising a nucleic acid encoding the anti-LAG-3 antibody or the fragment thereof. In certain embodiments, the composition comprises one or more antibodies that bind to LAG-3 or fragments or immunoconjugates thereof, or one or more nucleic acids encoding the one or more antibodies that bind to LAG-3 or the fragments thereof. Such compositions may further comprise suitable pharmaceutical adjuvants such as a pharmaceutical carrier, an excipient, and the like known in the art, including buffers.

The pharmaceutical carrier suitable for use in the invention can be sterile liquid, such as water and oil, including petroleum, or oil of an animal, vegetable, or a synthetic source, e.g., peanut oil, soybean oil, mineral oil, sesame oil, and the like. Water is a preferred carrier when the pharmaceutical composition is administered intravenously. Saline solutions and aqueous dextrose and glycerol solutions can also be employed as liquid carriers, particularly for injectable solutions.

Suitable excipients includes starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. For use of excipients, see *Handbook of Pharmaceutical Excipients*, the fifth edition, R. C. Rowe, P. J. Seskey and S. C. Owen, Pharmaceutical Press, London, Chicago. The composition may further comprise a small quantity of wetting agent or emulsifier, or pH buffer, if desired. The composition may take the form of a solution, a suspension, an emulsion, a tablet, a pill, a capsule, a powder, a sustained release preparation, and the like. Oral preparations may comprise standard carriers and/or excipients such as pharmaceutical-grade mannitol, lactose, starch, magnesium stearate and saccharin.

The pharmaceutical preparation, preferably in the form of a lyophilized preparation or an aqueous solution, comprising the anti-LAG-3 antibody described herein can be prepared by mixing the anti-LAG-3 antibody of desired purity of the invention with one or more optional pharmaceutical adjuvants (*Remington's Pharmaceutical Sciences,* 16th edition, Osol, A. ed. (1980)).

An exemplary lyophilized antibody preparation is described in U.S. Pat. No. 6,267,958. The aqueous antibody preparation includes those described in U.S. Pat. No. 6,171, 586 and WO 2006/044908, and the latter preparation comprises a histidine-acetate buffer.

The pharmaceutical composition or preparation of the invention may also comprise more than one active ingredient required by a treated particular indication, preferably active ingredients having complementarity activities without adversely affecting one another. For example, it may be desirable to further provide other anti-cancer active ingredients, such as chemotherapeutic agents and/or PD-1 axis binding antagonists (e.g., an anti-PD-1 antibody or an anti-PD-L1 antibody or an anti-PD-L2 antibody). The active ingredients are suitably combined in an amount effective for an intended purpose. The active ingredients may be any substance known in the art and capable of being combined with an anti-LAG-3 antibody, including chemotherapeutic agents, antibodies, and other therapeutic agents. Examples of the active ingredients can be seen in, for example, WO 2016/028672, WO 2015/042246, WO 2015/138920, and the like.

In some embodiments, the anti-PD-1 antibody or anti-PD-L1 antibody or anti-PD-L2 antibody is an anti-human PD-1 antibody or anti-human PD-L1 antibody or anti-human PD-L2 antibody, e.g., a humanized anti-human PD-1 antibody or anti-human PD-L1 antibody or anti-human PD-L2 antibody. A sustained release preparation can be prepared. Suitable examples of the sustained release preparation include a semipermeable matrix of a solid hydrophobic polymer comprising an antibody. The matrix is in the form of a shaped article, e.g., a film or a microcapsule.

Use of Antibody

In one aspect, the invention relates to a method for modulating an immune response in a subject. The method comprises administering to the subject an effective amount of the antibody molecule (e.g., the anti-LAG-3 antibody) or the pharmaceutical composition or the immunoconjugate disclosed herein, thereby modulating the immune response in the subject. In one embodiment, the antibody molecule (e.g., a therapeutically effective amount of the anti-LAG-3 antibody molecule) or the pharmaceutical composition or the immunoconjugate disclosed herein restores, enhances, stimulates or increases the immune response in the subject.

In another aspect, the invention relates to a method for preventing or treating a tumor (e.g., cancer) in a subject, wherein the method comprises administering to the subject an effective amount of the antibody molecule (e.g., the anti-LAG-3 antibody) or the pharmaceutical composition or the immunoconjugate disclosed herein. In one embodiment, the tumor is a gastrointestinal neoplasms (e.g., cancer), such as colon cancer.

In another aspect, the invention relates to a method for preventing or treating an infectious disease in a subject, wherein the method comprises administering to the subject an effective amount of the antibody molecule (e.g., the anti-LAG-3 antibody) or the pharmaceutical composition or the immunoconjugate disclosed herein. In one embodiment, the infectious disease is a chronic infection.

In another aspect, the invention relates to a method for inducing antibody-dependent cell-mediated cytotoxicity in a subject, wherein the method comprises administering to the subject an effective amount of the antibody molecule (e.g., the anti-LAG-3 antibody) or the pharmaceutical composition or the immunoconjugate disclosed herein.

The subject can be a mammal, e.g., a primate, preferably a higher primate, e.g., a human (e.g., a patient having or at risk of having the disease described herein). In one embodiment, the subject is in need of an enhanced immune response. In some embodiments, the anti-LAG-3 antibody molecule described herein restores, enhances or stimulates an antigen-specific T cell response in the subject, e.g., interleukin-2 (IL-2) or interferon-gamma (IFN-gamma) production in the antigen-specific T cell response. In some embodiments, the immune response is an anti-tumor response. In one embodiment, the subject has or is at risk of having the disease described herein (e.g., the tumor or infectious disease as described herein). In certain embodiments, the subject is immunocompromised or at risk of being immunocompromised. For example, the subject is receiving or has received chemotherapy and/or radiation therapy. Alternatively or in combination, the subject is immunocompromised due to infection or is at risk of being immunocompromised due to infection.

In some embodiments, the tumor, e.g., cancer, described herein comprises, but is not limited to, a solid tumor, a hematological cancer (e.g., leukemia, lymphoma, and myeloma) and metastatic lesions thereof. In one embodiment, the cancer is a solid tumor. Examples of the solid tumor include a malignant tumor, e.g., sarcomas and carcinomas (e.g., adenocarcinomas) of various organ systems, such as those affecting the lung, the breast, the lymph, the gastrointestinal tract or colorectum, the genitalia, the genitourinary tract (e.g., kidney cells and bladder cells), the pharynx, CNS (e.g., brain cells, nerve cells, or glial cells), the skin (e.g., melanoma), the head and neck (e.g., head and neck squamous cell carcinoma (HNCC)), and the pancreas, including, for example, melanoma, colon cancer, gastric cancer, rectal cancer, renal cell carcinoma, breast cancer (e.g., breast cancer that does not express one, two, or all estrogen receptors, the progesterone receptor, or Her2/neu, such as triple negative breast cancer), liver cancer, lung cancer (e.g., non-small cell lung cancer (NSCLC), such as NSCLC with squamous and/or non-squamous histology, or small cell liver cancer), prostate cancer, head or neck cancer (e.g., HPV+squamous cell carcinoma), small intestine cancer, and esophageal cancer. Examples of the hematological cancer include, but are not limited to, leukemia (e.g., myeloid leukemia, lymphoid leukemia, or chronic lymphocytic leukemia (CLL)), lymphoma (e.g., hodgkin's lymphoma (HL), non-hodgkin's lymphoma (NHL), diffuse large B-cell lymphoma (DLBCL), T-cell lymphoma, or mantle cell lymphoma (MCL)), and myeloma, e.g., multiple myeloma. The cancer may be in an early, intermediate or advanced stage or a metastatic cancer. In some embodiments, the cancer is selected from colorectal cancer (e.g., CRC); melanoma, e.g., advanced-stage melanoma (e.g., stage II-IV melanoma) or HLA-A2-positive melanoma; pancreatic cancer, e.g., advanced pancreatic cancer; breast cancer, e.g., metastatic breast cancer or triple negative breast cancer; head and neck cancer (e.g., HNSCC); esophageal cancer; renal cell carcinoma (RCC), e.g., renal clear cell carcinoma (ccRCC) or metastatic renal cell carcinoma (MRCC); lung cancer (e.g., NSCLC); cervical cancer; bladder cancer; or a hematological malignancy, e.g., leukemia (e.g., lymphocytic leukemia) or lymphoma (e.g., hodgkin's Lymphoma (HL), non-hodgkin's lymphoma (NHL), diffuse large B-cell lymphoma (DLBCL), mantle cell lymphoma (MCL), or CLL, e.g., relapsed or refractory chronic lymphocytic leukemia).

The methods and compositions disclosed herein may be used to treat metastatic lesions associated with the aforementioned cancers.

In some embodiments, the cancer is a cancer that expresses LAG-3, particularly a metastatic cancer. In some embodiments, the cancer is a cancer that expresses PD-L1. In some embodiments, the cancer is a cancer that expresses LAG-3 and PD-L1.

In some embodiments, the cancer described herein is colon cancer and metastatic cancer thereof.

In some embodiments, the infection is acute or chronic. In some embodiments, the chronic infection is a persistent infection, a latent infection, or a slow infection. In some embodiments, the chronic infection is caused by a pathogen selected from bacteria, viruses, fungi, and protozoa.

In one embodiment, the infectious disease is resulting from a virus infection. Some examples of pathogenic viruses include hepatitis viruses (A, B, and C), influenza viruses (A, B, and C), HIV, herpes viruses (e.g., VZV, HSV-1, HAV-6, HSV-II, CMV, and Epstein Barr virus), adenoviruses, flaviviruses, echoviruses, rhinoviruses, coxsackie viruses, corona viruses, respiratory syncytial viruses, mumps viruses, rotaviruses, measles viruses, rubella viruses, parvoviruses, vaccinia viruses, HTLV viruses, dengue viruses, papilloma viruses, molluscum viruses, polio viruses, rabies viruses, JC viruses, and arthropod-borne encephalitis viruses.

In some embodiments, the infection is a bacterial infection. Some examples of pathogens causing the bacterial infection include syphilis bacteria, *chlamydia, rickettsia*, mycobacteria, staphylococci, streptococci, pneumococci, meningococci, gonococci, *klebsiella*, proteobacteria, *serratia, pseudomonas, legionella, Corynebacterium diphtheriae, salmonella*, bacilli, cholera bacteria, tetanus bacilli, *Clostridium botulinum, colletotrichum*, plague bacilli, leptospira, and Lyme disease spirochete.

In some embodiments, the infection is a fungal infection, and some examples of pathogenic fungi include *candida* (*Candida albicans, candida krusei, candida glabrata, candida tropicalis*, etc.), *cryptococcus neoformans, aspergillus* (*Aspergillus fumigatus, Aspergillus niger*, etc.), mucorales (*mucor, absidia*, and *rhizopus*), *sporothrix schenkii, blastomyces dermatitidis, paracoccidioides brasiliensis, coccidioides immitis*, and *Histoplasma capsulatum*.

In some embodiments, the infection is a protozoan infection, such as a parasitic infection, and some examples of parasites include *entamoeba histolytica, balantidium coli, Naegleria fowleri, acanthamoeba* sp., *giardia lamblia, cryptosporidium* sp., *Pneumocystis carinii, Plasmodium vivax, babesia microti, Trypanosoma brucei, Trypanosoma cruzi, Leishmania donovani, toxoplasma gondi*, and *nippostrongylus brasiliensis*.

In one embodiment, the infectious disease is hepatitis (e.g., hepatitis B infection). The anti-LAG-3 antibody molecule (alone or in combination with a PD-1 axis binding antagonist, e.g., an anti-PD-1 or anti-PD-L1 antibody) can be combined with conventional treatments for hepatitis B infection for therapeutic advantages. In certain embodiments, the anti-LAG-3 antibody molecule is administered in combination with a hepatitis B antigen (e.g., Engerix B) or a vaccine, and optionally in combination with an aluminum-containing adjuvant.

In another embodiment, the infectious disease is influenza. In certain embodiments, the anti-LAG-3 antibody molecule is administered in combination with an influenza antigen or a vaccine.

For diseases suitable for being prevented or treated with the anti-LAG-3 antibody or the fragment thereof of the invention, further reference can be made to WO 2015/138920, WO 2016/028672, WO 2015/042246, etc.

In other aspects, the invention provides uses of the anti-LAG-3 antibody or the fragment thereof or the immunoconjugate thereof in the manufacture or preparation of a medicament for treating the above-mentioned related diseases or disorders.

In some embodiments, the antibody or the antibody fragment or the immunoconjugate of the invention delays the onset of the conditions and/or symptoms associated with the conditions.

Combination Therapy

In some embodiments, the prevention or treatment method described herein further comprises administering to the subject or individual the antibody molecule (e.g., the anti-LAG-3 antibody) or the pharmaceutical composition or the immunoconjugate disclosed herein, in combination with a PD-1 axis binding antagonist or a medicament or an immunoconjugate comprising the PD-1 axis binding antagonist. In some embodiments, the PD-1 axis binding antagonist comprises, e.g., an anti-PD-1 antibody or an anti-PD-L1 antibody or an anti-PD-L2 antibody.

In some embodiments, the PD-1 axis binding antagonist comprises, but is not limited to, a PD-1 binding antagonist, a PD-L1 binding antagonist, and a PD-L2 binding antagonist. Alternative names for "PD-1" include CD279 and SLEB2. Alternative names for "PD-L1" include B7-H1, B7-4, CD274, and B7-H. Alternative names for "PD-L2" include B7-DC, Btdc, and CD273. In some embodiments, PD-1, PD-L1, and PD-L2 are human PD-1, human PD-L1, and human PD-L2. In some embodiments, the PD-1 binding antagonist is a molecule that inhibits the binding of PD-1 to its ligand/binding partner. In a particular aspect, the PD-1 ligand/binding partner is PD-L1 and/or PD-L2. In another embodiment, the PD-L1 binding antagonist is a molecule that inhibits the binding of PD-L1 to its binding partner. In a particular aspect, the PD-L1 binding partner is PD-1 and/or B7.1. In another embodiment, the PD-L2 binding antagonist is a molecule that inhibits the binding of PD-L2 to its binding partner. In a particular aspect, the PD-L2 binding partner is PD-1. The antagonist may be an antibody or an antigen-binding fragment thereof, an immunoadhesin, a fusion protein or an oligopeptide. In some embodiments, the PD-1 binding antagonist is an anti-PD-1 antibody (e.g., a human antibody, a humanized antibody, or a chimeric antibody). In some embodiments, the anti-PD-1 antibody is selected from: MDX-1106 (nivolumab, OPDIVO), Merck 3475 (MK-3475, pembrolizumab, KEYTRUDA) and CT-011 (pidilizumab). In some embodiments, the PD-1 binding antagonist is an immunoadhesin (e.g., an immunoadhesin comprising an extracellular or PD-1 binding portion of PD-L1 or PD-L2 that is fused to a constant region (e.g., an Fc region of an immunoglobulin sequence)). In some embodiments, the PD-1 binding antagonist is AMP-224. In some embodiments, the PD-L1 binding antagonist is an anti-PD-L1 antibody. In some embodiments, the PD-L1 binding antagonist is selected from: YW243.55.S70, MPDL3280A, MEDI4736, and MDX-1105. MDX-1105, also known as BMS-936559, is an anti-PD-L1 antibody described in WO 2007/005874. Antibody YW243.55.S70 (with a heavy chain variable region sequence and a light chain variable region sequence shown as SEQ ID NOs: 20 and 21 respectively) is an anti-PD-L1 antibody described in WO 2010/077634 A1. MDX-1106, also known as MDX-1106-04, ONO-4538, BMS-936558, or nivolumab, is an anti-PD-1 antibody described in WO 2006/121168. Merck 3475, also known as MK-3475, SCH-900475, or pembrolizumab, is an anti-PD-1 antibody described in WO 2009/114335. CT-011, also known as hBAT, hBAT-1, or pidilizumab, is an anti-PD-1 antibody described in WO 2009/101611. AMP-224, also known as B7-DCIg, is a PD-L2-Fc fusion soluble receptor described in WO 2010/027827 and WO 2011/066342. In some embodiments, the anti-PD-1 antibody is MDX-1106. Alternative names for "MDX-1106" include MDX-1106-04, ONO-4538, BMS-936558, or nivolumab. In some embodiments, the anti-PD-1 antibody is nivolumab (CAS Registry Number: 946414-94-4). In a preferred embodiment, the anti-PD-1 antibody is "Antibody C" or "Antibody D" as described herein.

In some embodiments, the anti-LAG-3 antibody of the invention may be used for treatment in combination with an anti-PD-L1 antibody.

In some embodiments, the anti-PD-L1 antibody of the invention is an anti-human PD-L1 antibody. In some embodiments, the anti-PD-L1 antibody disclosed herein is an IgG1 antibody, an IgG2 antibody, or an IgG4 antibody. In some embodiments, the anti-PD-L1 antibody is a monoclonal antibody. In some embodiments, the anti-PD-L1 antibody is humanized. In some embodiments, the anti-PD-L1 antibody is a chimeric antibody. In some embodiments, at least a portion of the framework sequence of the anti-PD-L1 antibody is a human consensus framework sequence. In one embodiment, the anti-PD-L1 antibody of the invention also comprises an antibody fragment thereof, preferably an antibody fragment selected from: Fab, Fab', Fab'-SH, Fv, a single-chain variable fragment (e.g., scFv) or (Fab')$_2$, a single-domain antibody, a diabody (dAb), and linear antibody.

In some specific embodiments, the anti-PD-L1 antibody or the antigen-binding fragment thereof of the invention comprises:

(i) three complementarity determining regions of a heavy chain variable region shown as SEQ ID NO: 57 (HCDRs), and/or (ii) three complementarity determining regions of the light chain variable region shown as SEQ ID NO: 58 (LCDRs).

In some embodiments, the anti-PD-L1 antibody or the antigen-binding fragment thereof of the invention comprises a heavy chain variable region (VH) and/or a light chain variable region (VL), wherein (i) the VH comprises complementarity determining regions (CDRs) HCDR1, HCDR2 and HCDR3, wherein the HCDR1 comprises or consists of the amino acid sequence of SEQ ID NO: 51; the HCDR2 comprises or consists of an amino acid sequence selected from SEQ ID NO: 52; and the HCDR3 comprises or consists of the amino acid sequence of SEQ ID NO: 53; and/or (ii) the VL comprises complementarity determining regions (CDRs) LCDR1, LCDR2, and LCDR3, wherein the LCDR1 comprises or consists of the amino acid sequence of SEQ ID NO: 54; the LCDR2 comprises or consists of the amino acid sequence of SEQ ID NO: 55; and the LCDR3 comprises or consists of an amino acid sequence selected from SEQ ID NO: 56.

In some embodiments, the anti-PD-L1 antibody or the antigen-binding fragment thereof of the invention comprises a heavy chain variable region VH and/or a light chain variable region VL, wherein, (a) the heavy chain variable region VH (i) comprises or consists of an amino acid sequence having at least 90%, 91%, 92%, 93%, 94%, 95%, 96%, 97%, 98% or 99% identity with an amino acid sequence selected from SEQ ID NO: 57, (ii) comprises or consists of an amino acid sequence selected from SEQ ID NO: 57, or (iii) comprises an amino acid sequence having 1 or more (preferably not more than 10, and more preferably not more than 5, 4, 3, 2, or 1) amino acid alterations (preferably amino acid substitutions, and more preferably amino acid conservative substitutions) as compared to the amino acid sequence selected from SEQ ID NO: 57, wherein preferably, the amino acid alterations do not occur in the CDRs; and/or (b) the light chain variable region VL (i) comprises or consists of an amino acid sequence having at least 90%, 91%, 92%, 93%, 94%, 95%, 96%, 97%, 98% or 99% identity with an amino acid sequence selected from SEQ ID NO: 58, (ii) comprises or consists of an amino acid sequence of SEQ ID NO: 58, or (iii) comprises an amino acid sequence having 1 or more (preferably not more than 10, more preferably not more than 5, 4, 3, 2 or 1) amino acid alterations (preferably amino acid substitutions, and more preferably amino acid conservative substitutions) as compared to an amino acid sequence selected from SEQ ID NO: 58, wherein preferably, the amino acid alterations do not occur in the CDRs.

In some embodiments, the anti-PD-L1 antibody or the antigen-binding fragment thereof of the invention comprises a heavy chain and/or a light chain, wherein (a) the heavy chain (i) comprises or consists of an amino acid sequence having at least 85%, 90%, 91%, 92%, 93%, 94%, 95%, 96%, 97%, 98% or 99% identity with an amino acid sequence selected from SEQ ID NO: 59, (ii) comprises or consists of an amino acid sequence selected from SEQ ID NO: 59, or (iii) comprises an amino acid sequence having 1 or more (preferably not more than 20 or 10, and more preferably not more than 5, 4, 3, 2 or 1) amino acid alterations (preferably amino acid substitutions, and more preferably amino acid conservative substitutions) as compared to an amino acid sequence selected from SEQ ID NO: 59, wherein preferably, the amino acid alterations do not occur in the CDRs of the heavy chain, and more preferably, the amino acid alterations do not occur in the heavy chain variable region; and/or (b) the light chain (i) comprises or consists of an amino acid sequence having at least 85%, 90%, 91%, 92%, 93%, 94%, 95%, 96%, 97%, 98% or 99% identity with an amino acid sequence selected from SEQ ID NO: 60, (ii) comprises or consists of an amino acid sequence selected from SEQ ID NO: 60, or (iii) comprises an amino acid sequence having 1 or more (preferably not more than 20 or 10, and more preferably not more than 5, 4, 3, 2 or 1) amino acid alterations (preferably amino acid substitutions, and more preferably amino acid conservative substitutions) as compared to an amino acid sequence selected from SEQ ID NO: 60, wherein preferably, the amino acid alterations do not occur in the CDRs of the light chain, and more preferably, the amino acid alterations do not occur in the light chain variable region. In some embodiments, modifications to the anti-LAG-3 antibody of the invention are also applicable to the anti-PD-L1 antibody.

In some further embodiments, the anti-LAG-3 antibody or a fragment thereof, alone or in combination with a PD-1 axis binding antagonist, can also be administered in combination with one or more other therapies, e.g., therapeutic modalities and/or therapeutic agents.

In some embodiments, the therapeutic modalities comprise surgery (e.g., tumor resection), a radiation therapy (e.g., an external beam therapy that involves a three-dimensional conformal radiation therapy in which an irradiation region is designed), partial irradiation (e.g., irradiation directed to a preselected target or an organ), focused irradiation, and the like. The focused irradiation may be selected from stereotactic radiosurgery, fractionated stereotactic radiosurgery, and intensity-modulated radiotherapy. The focused irradiation may have a radiation source selected from particle beams (protons), cobalt-60 (photons), and linear accelerators (X-rays), for example, as described in WO 2012/177624.

The radiation therapy can be conducted through one or a combination of methods including, but not limited to, external beam therapy, internal radiation therapy, implant irradiation, stereotactic radiosurgery, systemic radiotherapy, radiotherapy and permanent or transient interstitial brachytherapy. The term "brachytherapy" refers to radiation therapy delivered by a spatially confined radioactive substance inserted into the body at or near the sites of tumors or other proliferative tissue diseases. The term is intended to include, but not be limited to, exposure to radioisotopes (e.g., At-211, I-131, I-125, Y-90, Re-186, Re-188, Sm-153, Bi-212, P-32, and radioactive isotopes of Lu). Suitable radiation sources include solids and liquids. By way of non-limiting examples, the radiation source may be a radionuclide, such as I-125, I-131, Yb-169 and Ir-192 as a solid source, I-125 as a solid source, or other radionuclides that emit photons, beta particles, gamma radiation or other therapeutic rays. The radioactive substance may also be a fluid made from any radionuclide solution, for example, an 1-125 or 1-131 solution, or a radioactive fluid can be produced by using a slurry of a suitable fluid containing small particles of a solid radionuclide (e.g., Au-198 and Y-90). In addition, the radionuclide may be contained in gel or radioactive microspheres.

In some embodiments, the therapeutic agent is selected from a chemotherapeutic agent, a cytotoxic agent, a vaccine, other antibodies, an anti-infective active agent, and an immunomodulatory agent (such as an activator of a co-stimulatory molecule or an inhibitor of an immune checkpoint molecule).

Exemplary cytotoxic agents include anti-microtubule drugs, topoisomerase inhibitors, antimetabolites, mitotic inhibitors, alkylating agents, anthracyclines, *vinca* alkaloids, intercalator, active agents capable of interfering with signal transduction pathways, active apoptotic agents, proteasome inhibitors, and irradiation (e.g., partial or total body irradiation (e.g., gamma radiation)).

Other exemplary antibodies include, but are not limited to, immune checkpoint inhibitors (e.g., anti-CTLA-4, anti-TIM-3, and anti-CEACAM), antibodies (e.g., agonistic GITR antibodies or CD137 antibodies) that stimulate immune cells, anti-cancer antibodies (e.g., rituximab (Rituxan® or MabThera®), trastuzumab (Herceptin®), tositumomab (Bexxar®), ibritumomab (Zevalin®), alemtuzumab (Campath®), epratuzumab (Lymphocide®), bevacizumab (Avastin®), erlotinib (Tarceva®), cetuximab (Erbitux®)), and the like.

Exemplary chemotherapeutic agents include, but are not limited to, anastrozole (Arimitex®), bicalutamide (Casodex®), bleomycin sulfate (Blenoxane®), busulfan (Myleran®), busulfan injection (Busulfex®), capecitabine (Xeloda®), N4-pentyloxycarbonyl-5-deoxy-5-fluorocytidine, carboplatin (Parapalatin®), carmustine (BiCNU®), chlorambucil (Leukeran®), cisplatin (Platinol®), cladribine (Leustatin®), cyclophosphamide (Cytoxan® or Neosar®), cytosine arabinoside, cytosine arabinoside (Cytosar-U®), depocyt (DepoCyt®), dacarbazine (DTIC-Dome®), dactinomycin (actinomycin D and Cosmegan), daunomycin hydrochloride (Cerubidine®), daunomycin citrate liposome injection (DaunoXome®), dexamethasone, docetaxel (Taxotere®), doxorubicin hydrochloride (Adriamycin® and Rubex®), etoposide (Vepesid®), fludarabine phosphate (Fludara®), 5-fluorouracil (Adrucil® and Efudex®), flutamide (Eulexin®), tezacitibine, gemcitabine (difluorodeoxycytidine), hydroxyurea (Hydrea®), idarubicin (Idamycin®), ifosfamide (IFEX®), irinotecan (Camptosar®), L-asparaginase (ELSPAR®), calcium folinate, melphalan (Alkran®), 6-mercaptopurine (Purinethol®), methotrexate (Folex®), mitoxantrone, gemtuzumab ozogamicin (mylotarg), paclitaxel (Taxol®), phoenix (yttrium 90/MX-DTPA), pentostatin, polifeprosan 20 in combination with carmustine implants (Gliadel®), tamoxifen citrate (Nolvadex®), teniposide (Vumon®), 6-thioguanine, thiotepa, tirapazamine (Tirazoline®), topotecan hydrochloride for injection (Hycamptin®), vinblastine (Velban®), vincristine (Oncovin®), vinorelbine, ibrutinib, girelide (idelalisib), and brentuximab vedotin.

Exemplary vaccines include, but are not limited to, cancer vaccines. The vaccine may be a DNA-based vaccine, a RNA-based vaccine, or a virus transduction-based vaccine. Cancer vaccines can be prophylactic or therapeutic. In some embodiments, the cancer vaccine is a peptide cancer vaccine which is a personalized peptide vaccine in some embodiments. In some embodiments, the peptide cancer vaccine is multivalent long peptide, multiple peptide, peptide mixture, hybrid peptide, or peptide-pulsed dendritic cell vaccine (see, e.g., Yamada et al., Cancer Sci, 104: 14-21, 2013).

Exemplary active anti-infective agents include, but are not limited to, antivirals, antifungals, antiprotozoals, and antibacterials, such as nucleoside analogs (zidovudine (AST), ganciclovir, foscarnet, or cidovir), as described above.

The immunomodulatory agents include an inhibitor of an immune checkpoint molecule and an activator of a co-stimulatory molecule.

In some embodiments, the inhibitor of an immune checkpoint molecule is an inhibitor of CTLA-4, TIM-3, VISTA, BTLA, TIGIT, LAIR1, CD160, 2B4, CEACAM (e.g., CEACAM-1 and/or CEACAM-5), and/or TGFR. Inhibition of the molecule may occur at DNA, RNA, or protein level. In some embodiments, inhibitory nucleic acids (e.g., dsRNA, siRNA, or shRNA) can be used to inhibit the expression of immune checkpoint molecules. In other embodiments, the inhibitor of an immune checkpoint molecule is a polypeptide that binds to the immune checkpoint molecule, e.g., a soluble ligand or an antibody or an antibody fragment. Exemplary TIM-3 antibody molecules include, but are not limited to, MBG220, MBG227, and MBG219.

In other embodiments, the immunomodulatory agent is a soluble ligand of CTLA4 (e.g., CTLA-4-Ig or TIM-3-Ig) or an antibody or an antibody fragment. For example, an anti-LAG-3 antibody molecule (alone or with a PD-1 axis binding antagonist) can be administered in combination with a CTLA-4 antibody (e.g., ipilimumab). Exemplary anti-CTLA-4 antibodies include tremelimumab (an IgG 2 monoclonal antibody available from Pfizer, previously known as ticilimumab, and CP-675,206); and ipilimumab (a CTLA-4 antibody, also known as MDX-010, CAS No. 477202-00-9).

In some embodiments, the immunomodulatory agent is an activator or agonist of a co-stimulatory molecule. In one embodiment, the agonist of a co-stimulatory molecule is an agonist (e.g., an agonistic antibody or an antigen-binding fragment thereof, or a soluble fusion) of a molecule selected from OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3, or CD83 ligand. In another embodiment, the anti-LAG-3 antibody or a fragment thereof, alone or in combination with a PD-1 axis binding antagonist, is used in combination with a co-stimulatory molecule (e.g., an agonist associated with a positive signal) including the co-stimulatory domains of CD28, CD27, ICOS, and GITR. Exemplary GITR agonists include, for example, GITR fusion proteins and anti-GITR antibodies (e.g., bivalent anti-GITR antibodies), e.g., GITR fusion proteins described in U.S. Pat. No. 6,111,090, European Patent No. 090505B1, U.S. Pat. No. 8,586,023, and PCT Publication Nos. WO 2010/003118 and 2011/090754. An exemplary anti-GITR antibody is TRX518.

In some further embodiments, the anti-LAG-3 antibody or the fragment thereof, alone or in combination with a PD-1 axis binding antagonist, can also be used in combination with a tyrosine kinase inhibitor (e.g., a receptor tyrosine kinase (RTK) inhibitor). Exemplary tyrosine kinase inhibitors include, but are not limited to, epidermal growth factor (EGF) pathway inhibitors (e.g., epidermal growth factor receptor (EGFR) inhibitors), vascular endothelial growth factor (VEGF) pathway inhibitors (e.g., vascular endothelial growth factor receptor (VEGFR) inhibitors, for example, VEGFR-1 inhibitors, VEGFR-2 inhibitors, and VEGFR-3 inhibitors), platelet-derived growth factor (PDGF) pathway inhibitors (e.g., platelet-derived growth factor receptor (PDGFR) inhibitors, for example, PDGFR-beta inhibitors), RAF-1 inhibitors, KIT inhibitors, and RET inhibitors.

In some embodiments, the anti-LAG-3 antibody or the fragment thereof, alone or in combination with a PD-1 axis binding antagonist, can also be used in combination with a PI3K inhibitor, an mTOR inhibitor, a BRAF inhibitor, an MEK inhibitor, a JAK2 inhibitor, and/or the like.

In some embodiments of any of the methods of the invention, the anti-LAG-3 antibody or the fragment thereof of the invention, alone or in combination with a PD-1 axis binding antagonist, is administered in combination with a tumor antigen. The antigen may be, for example, a tumor antigen, a viral antigen, a bacterial antigen, or an antigen from a pathogen. In some embodiments, the tumor antigen comprises a protein. In some embodiments, the tumor antigen comprises a nucleic acid. In some embodiments, the tumor antigen is a tumor cell.

In some embodiments, the anti-LAG-3 antibody or the fragment thereof of the invention, alone or in combination with a PD-1 axis binding antagonist, can be administered in combination with a therapy comprising adoptive transfer of T cells (e.g., cytotoxic T cells or CTLs) expressing a chimeric antigen receptor (CAR).

In some embodiments, the anti-LAG-3 antibody or the fragment thereof of the invention, alone or in combination with a PD-1 axis binding antagonist, can be administered in combination with an anti-tumor agent.

In some embodiments, the anti-LAG-3 antibody or the fragment thereof of the invention, alone or in combination with a PD-1 axis binding antagonist, can be administered in combination with an oncolytic virus. In some embodiments, the anti-LAG-3 antibody or the fragment thereof of the invention, alone or in combination with a PD-1 axis binding antagonist, can be administered in combination with a cytokine.

The cytokine may be administered as a fusion molecule with the anti-LAG-3 antibody molecule, or as a separate composition. In one embodiment, the anti-LAG-3 antibody is administered in combination with one, two, three, or more cytokines (e.g., as a fusion molecule or as a separate composition). In one embodiment, the cytokine is an interleukin (IL) selected from one, two, three, or more of IL-1, IL-2, IL-12, IL-15, and IL-21.

In some embodiments, the antibody or the fragment thereof of the invention, alone or in combination with a PD-1 axis binding antagonist, can be combined with a conventional cancer therapy in the art, and the conventional cancer therapy includes, but is not limited to, (i) radiation therapies (e.g., radiation therapy, X-ray therapy, and irradiation), or ionizing radiation to kill cancer cells and reduce tumors, wherein the radiation therapy can be conducted through external beam radiation therapy (EBRT) or internal brachytherapy; (ii) chemotherapies, or application of cytotoxic drugs, which generally affect cells that are rapidly dividing; (iii) targeted therapies, or agents (e.g., tyrosine kinase inhibitor such as imatinib and gefitinib; monoclonal antibody; photodynamic therapy) that specifically affect the deregulation of cancer cell proteins; (iv) immunotherapies, or enhanced host immune responses (e.g., vaccine); (v) hormone therapies, or blocking hormones (e.g., when the tumors are sensitive to hormones); (vi) angiogenesis inhibitors, or therapies blocking angiogenesis and growth; and (vii) palliative care, or such therapies that relate to improving the quality of healthcare to manage pain, nausea, vomiting, diarrhea, and bleeding, in which analgesics such as morphine and oxycodone and anti-emetics such as ondansetron and aprepitant are given to allow a more aggressive therapeutic regimen.

In some embodiments, the antibody or the fragment thereof of the invention, alone or in combination with a PD-1 axis binding antagonist, can be combined with a conventional method enhancing host immune functions. The conventional method includes, but is not limited to: (i) APC enhancement by, for example, (a) injecting a DNA encoding a heterologous MHC alloantigen to a tumor, or (b) transfecting a biopsied tumor cell with a gene that increases the possibility of immune antigen recognition (e.g., immunostimulatory cytokine, GM-CSF, co-stimulatory molecule B7.1, and co-stimulatory molecule B7.2), and (ii) adoptive cellular immunotherapy, or activated tumor-specific T cell therapy. The adoptive cell immunotherapy includes isolating tumor-infiltrating host T lymphocytes, and stimulating the expansion of the population in vitro, for example, through IL-2 or the tumor or both; in addition, isolated dysfunctional T cells can be activated through in-vitro application of the antibody of the invention, and then the activated T cells can be re-administered to the host.

The various combination therapies described above can be further combined for treatment.

More examples of combinations of anti-LAG-3 antibodies with other therapeutic modalities or agents can be found in WO 2015/138920, WO 2016/028672, WO 2015/042246 and the like.

Such combination therapies encompass both co-administration (wherein two or more therapeutic agents are contained in the same formulation or separate formulations), and separate administration, in which administration of the antibody of the invention can occur prior to, concurrently with, and/or after the administration of other therapies, e.g., therapeutic modalities or therapeutic agents. The antibody molecule and/or other therapies, e.g., therapeutic agents or therapeutic modalities, can be administered during active diseases or in the period of remission or less active diseases. The antibody molecule may be administered prior to other therapies, concurrently with other therapies, after other therapies, or during remission of diseases.

In one embodiment, administration of the anti-LAG-3 antibody and administration of other therapies (such as therapeutic modalities or therapeutic agents) occur within about one month, or within about one, two, or three weeks, or within about 1, 2, 3, 4, 5, or 6 days from each other.

In some embodiments, the antibody combinations described herein can be administered separately (e.g., as separate antibodies) or in linkage (e.g., as a bispecific or trispecific antibody molecule).

It will be appreciated that any therapy can be performed by using the immunoconjugate of the invention in place of or in addition to the anti-LAG-3 antibody.

Route of Administration and Dosage

The antibody of the invention (or the pharmaceutical composition or the immunoconjugate containing the antibody, or any other therapeutic agents) can be administered by any suitable means, including parenteral administration, intrapulmonary administration, intranasal administration, and intralesional administration if needed by local treatment. Parenteral infusion includes intramuscular, intravenous, intraarterial, intraperitoneal, or subcutaneous administration. The medicaments may be administered by any suitable means, such as injection, e.g., intravenous or subcutaneous injection, to some extent depending on short-term or long-term treatment. Various dosing schedules are contemplated herein, including, but not limited to, single administration, or multiple administrations, bolus injections, and pulse infusions at multiple time points.

In order to prevent or treat a disease, the appropriate dosage (when used alone or in combination with one or more of other therapeutic agents) of the antibody of the invention will depend on the type of the disease to be treated, the type of the antibody, the severity and progression of the disease, whether the antibody is administered for prophylactic or therapeutic purposes, previous treatments, clinical history of a patient and responses to the antibody, and the discretion of an attending physician. The antibody is suitably administered to a patient through a single dose or through a series of treatments.

In some embodiments, the dose regimen is adjusted to provide the optimal desired response (for example, a therapeutic response). For example, a single bolus injection may be given, several separate doses may be administered over time, or a dose may be proportionally reduced or increased as indicated by the criticality of the treatment condition. It is particularly advantageous to formulate a parenteral composition in a dosage unit form for ease of dose administration and uniformity. The dosage unit form as used herein refers to physically separated units suitable as unitary doses for subjects to be treated; each unit contains a predetermined quantity of active compound, which is calculated to produce a desired therapeutic effect in combination with a required pharmaceutical carrier. The specification of the dosage unit form of the invention is directly dependent on (a) the unique characteristics of the active compound and the particular therapeutic effect to be achieved, and (b) limitations which are unique in the field of combining the active compound for a sensitive therapy in an individual.

In some embodiments, an exemplary, non-limiting range of the therapeutically or prophylactically effective amount of the antibody molecule is 0.1 to 30 mg/kg, preferably 1 to 25 mg/kg, and more preferably 5 to 15 mg/kg. The dosage and treatment regimen of the anti-LAG-3 antibody molecule can be determined by those skilled. In certain embodiments, the anti-LAG-3 antibody molecule is administered by injection (e.g., subcutaneously or intravenously) at a dose of about 1 to 40 mg/kg, e.g., 1 to 30 mg/kg, e.g., about 5 to 25 mg/kg, about 10 to 20 mg/kg, about 1 to 5 mg/kg, 1 to 10 mg/kg, 5 to 15 mg/kg, 10 to 20 mg/kg, 15 to 25 mg/kg, or about 3 mg/kg. The regimen may range from, for example, once a week to once every 2, 3, or 4 weeks. In one embodiment, the anti-LAG-3 antibody molecule is administered every other week at a dose of about 10 to 20 mg/kg. The antibody molecule may be administered by intravenous infusion at a rate of greater than 20 mg/min, such as 20 to 40 mg/min, and preferably greater than or equal to 40 mg/min, to achieve a dose of about 35 to 440 mg/m$^2$, preferably about 70 to 310 mg/m$^2$, and more preferably about 110 to 130 mg/m$^2$. In an embodiment, a dose of about 3 mg/kg is achieved at an infusion rate of about 110 to 130 mg/m$^2$. In one embodiment, the anti-LAG-3 antibody molecule is administered (e.g., intravenously administered) at a dose of about 3 to 800 mg (e.g., about 3, 20, 80, 240, or 800 mg). In certain embodiments, the anti-LAG-3 antibody molecule is administered alone at a dose of about 20 to 800 mg (e.g., about 3, 20, 80, 240, or 800 mg). In other embodiments, the anti-LAG-3 antibody molecule is administered at a dose of about 3 to 240 mg (e.g., about 3, 20, 80, or 240 mg) in combination with a second active agent or therapeutic modality (e.g., the second active agent or therapeutic modality described herein). In one embodiment, the anti-LAG-3 antibody molecule is administered every 2 weeks in each 8-week cycle (e.g., in the 1st, the 3rd, the 5th and the 7th weeks), e.g., which lasts up to 96 weeks. In some embodiments, the antibody molecule may be administered by intravenous infusion at a rate of greater than 20 mg/min, such as 20 to 40 mg/min, and preferably greater than or equal to 40 mg/min, to achieve a dose of about 35 to 440 mg/m$^2$, preferably about 70 to 310 mg/m$^2$, and more preferably about 110 to 130 mg/m$^2$. In an embodiment, a dose of about 3 mg/kg is achieved at an infusion rate of about 110 to 130 mg/m$^2$. In other embodiments, the antibody molecule may be administered by intravenous infusion at a rate of less than 10 mg/min, e.g., less than or equal to 5 mg/min, to achieve a dose of about 1 to 100 mg/m$^2$, such as about 5 to 50 mg/m$^2$ and about 7 to 25 mg/m$^2$, and preferably about 10 mg/m$^2$. In some embodiments, the antibody is injected over a period of about 30 minutes.

In another embodiment, the anti-LAG-3 antibody molecule is administered in combination with an anti-PD-1 antibody. Exemplary doses for the anti-PD-1 antibody molecule that can be used include a dose of about 1 to 10 mg/kg (e.g., 3 mg/kg). The anti-LAG-3 antibody molecule may be administered in combination at a dose of about 20 to 800 mg, e.g., about 20, 80, 240, or 800 mg. In one embodiment, the anti-LAG-3 antibody molecule is administered every 2 weeks in each 8-week cycle (e.g., in the 1st, the 3rd, the 5th and the 7th weeks), e.g., which lasts up to 96 weeks.

Method and Composition for Diagnosis and Detection

In certain embodiments, any of the anti-LAG-3 antibodies or the antigen-binding fragments thereof provided herein can be used for detecting the presence of LAG-3 in a biological sample. The term "detection" as used herein includes quantitative or qualitative detection, and exemplary detections may involve immunohistochemistry, immunocytochemistry, flow cytometry (e.g., FACS), magnetic beads complexed with antibody molecules, ELISA, and PCR techniques (e.g., RT-PCR). In some embodiments, the biological sample is blood, serum, or other fluid sample of a biological source. In certain embodiments, the biological sample includes cells or tissues. In some embodiments, the biological sample is derived from a proliferative or cancerous lesion.

In one embodiment, an anti-LAG-3 antibody is provided for use in a diagnostic or detection method. In another aspect, a method for detecting the presence of LAG-3 in a biological sample is provided. In certain embodiments, the method comprises detecting the presence of LAG-3 proteins in a biological sample. In certain embodiments, LAG-3 is human LAG-3. In certain embodiments, the method comprises contacting the biological sample with the anti-LAG-3 antibody as described herein under a condition that allows the anti-LAG-3 antibody to bind to LAG-3, and detecting whether a complex is formed by the anti-LAG-3 antibody and LAG-3. The formation of the complex indicates the presence of LAG-3. The method may be an in-vitro or in-vivo method. In one embodiment, the anti-LAG-3 antibody is used to select a subject suitable for treatment with the anti-LAG-3 antibody, e.g., wherein LAG-3 is a biomarker for selecting the subject.

In one embodiment, the antibody of the invention can be used to diagnose cancers or tumors, e.g., to assess (e.g., monitor) the treatment or progression, diagnosis and/or staging of a disease (e.g., the hyperproliferative or cancerous disease) described herein in a subject.

In certain embodiments, a labeled anti-LAG-3 antibody is provided. The label includes, but is not limited to, a label or moiety (e.g., a fluorescent label, a chromophoric label, an electron-dense label, a chemiluminescent label, and a radioactive label) that is detected directly, as well as a moiety that is detected indirectly, such as an enzyme or a ligand, for example, by an enzymatic reaction or a molecular interaction. Exemplary labels include, but are not limited to, radioisotopes of $^{32}P$, $^{14}C$, $^{125}I$, $^{3}H$, and $^{131}I$, fluorophores (e.g., rare earth chelates or luciferin and derivatives thereof), rhodamine and derivatives thereof, dansyl, umbelliferone, luceriferase [e.g., firefly luciferase and bacterial luciferase (U.S. Pat. No. 4,737,456)], luciferin, 2,3-dihydrophthalazinedione, horseradish peroxidase (HR), alkaline phosphatase, beta-galactosidase, glucoamylase, lysase, carbohydrate oxidases (e.g., glucose oxidase, galactose oxidase, and glucose-6-phosphate dehydrogenase), heterocyclic oxidases (e.g., uricase and xanthine oxidase), enzymes utilizing hydrogen peroxide to oxidize dye precursors (e.g., HR, lactoperoxidase, or microperoxidase), biotin/avidin, spin labels, phage labels, stable free radicals, and the like.

In some embodiments of the invention provided herein, the sample is obtained prior to treatment with the anti-LAG-3 antibody. In some embodiments, the sample is obtained prior to treatment with an anti-cancer drug. In some embodiments, the sample is obtained after the cancer has metastasized. In some embodiments, the sample is a formalin-fixed, paraffin-embedded (FFPE) sample. In some embodiments, the sample is a biopsy (e.g., a core biopsy) specimen, a surgical specimen (e.g., a specimen from a surgical resection), or a fine-needle aspirate.

In some embodiments, LAG-3 is detected prior to treatment, e.g., prior to an initial treatment or prior to a treatment after an interval from a certain treatment.

In some embodiments, a method for treating a tumor or an infection is provided, which comprises: detecting the presence of LAG-3 in a subject (for example, a sample, e.g., a sample containing cancer cells of the subject), thereby determining an LAG-3 value; comparing the LAG-3 value to a reference value; and if the LAG-3 value is greater than the reference value, administering a therapeutically effective amount of an anti-LAG-3 antibody (e.g., the anti-LAG-3 antibody described herein), alone or in combination of a PD-1 axis binding antagonist, optionally in combination with one or more other therapies, to the subject, thereby treating the tumor or infection.

Exemplary Sequences of Anti-LAG-3 Antibodies of the Invention

TABLE 1

CDR sequences of heavy- and light-chain variable regions of exemplary antibodies of the invention

| Antibody | HCDR1 | HCDR2 (Kabat) | HCDR3 (IMGT) |
| --- | --- | --- | --- |
| ADI-26789 | FTFDDYAMH (SEQ ID NO: 1) | GISWNSGDIGYADSVKG (SEQ ID NO: 5) | AKGGYDGSYYGMDV (SEQ ID NO: 8) |
| ADI-26869 | GSISSSDYYWG (SEQ ID NO: 2) | SIYYSGSTYYNPSLKS (SEQ ID NO: 6) | ARVRTWDAAFDI (SEQ ID NO: 9) |
| ADI-31851 | GSISSPDYYWG (SEQ ID NO: 3) | SIVYSGYTYYNPSLKS (SEQ ID NO: 7) | ARVRTWDQSFDI (SEQ ID NO: 10) |
| ADI-31853 | GSIYSESYYWG (SEQ ID NO: 4) | SIVYSGYTYYNPSLKS (SEQ ID NO: 7) | ARVRTWDAAFDI (SEQ ID NO: 9) |
| Consensus sequence | GSIX$_1$SX$_2$X$_3$YYWG (wherein X$_1$ is selected from any amino acids, preferably S or Y, X$_2$ is selected from any amino acids, preferably S, P, or E, and/or X$_3$ is selected from any amino acids, preferably D or S) (SEQ ID NO: 17) | SIX$_1$YSGX$_2$TYYNPSLKS (wherein X$_1$ is selected from any amino acids, preferably Y or V, and/or X$_2$ is selected from any amino acids, preferably S or Y) (SEQ ID NO: 18) | ARVRTWDX$_1$X$_2$FDI (wherein X$_1$ is selected from any amino acids, preferably A or Q, and/or X$_2$ is selected from any amino acids, preferably A or S) (SEQ ID NO: 19) |
| HZ3266-IgG1N297A* | GFNIEDT (SEQ ID NO: 51) | DPANDD (SEQ ID NO: 52) | GLGRWFAY (SEQ ID NO: 53) |

| Antibody | LCDR1 (Kabat) | LCDR2 (Kabat) | LCDR3 (Kabat) |
| --- | --- | --- | --- |
| ADI-26789 | QASQDISNYLN (SEQ ID NO: 11) | DASNLET (SEQ ID NO: 13) | QQVLDLPLT (SEQ ID NO: 14) |
| ADI-26869 | QASQDISNYLN (SEQ ID NO: 11) | DASNLET (SEQ ID NO: 13) | QQVHALPPWT (SEQ ID NO: 15) |
| ADI-31851 | QAGQDISNYLN (SEQ ID NO: 12) | DASNLET (SEQ ID NO: 13) | QQVLELPPWT (SEQ ID NO: 16) |
| ADI-31853 | QASQDISNYLN (SEQ ID NO: 11) | DASNLET (SEQ ID NO: 13) | QQVLELPPWT (SEQ ID NO: 16) |
| Consensus sequence | QAXQDISNYLN (wherein X is selected from any amino acids, preferably S or G) (SEQ ID NO: 20) | | QQVX$_1$X$_2$LPPWT (wherein X$_1$ is selected from any amino acids, preferably H or L, and/or X$_2$ is selected from any amino acids, preferably A or E) (SEQ ID NO: 21) |
| HZ3266-IgG1N297A* | KASQDVINAVA (SEQ ID NO: 54) | SASNRYT (SEQ ID NO: 55) | QQHYSPPLT (SEQ ID NO: 56) |

*HCDR is defined using Chothia numbering scheme and LCDR is defined by Kabat numbering scheme.

TABLE 2

Sequences of heavy- and light-chain variable regions of exemplary antibodies of the invention

| Antibody | Heavy chain variable region (VH) | Light chain variable region (VL) |
|---|---|---|
| ADI-26789 | EVQLVESGGGLVQPGRSLRLSCAASGFTFDDYAMHWVR QAPGKGLEWVSGISWNSGDIGYADSVKGRFTISRDNAK NSLYLQMNSLRAEDTALYYCAKGGYDGSYYGMDVWGQG TTVTVSS(SEQ ID NO: 22) | DIQMTQSPSSLSASVGDRVTITCQASQDISNYLNWYQQKPGKAP KLLIYDASNLETGVPSRFSGSGSGTDFTFTISSLQPEDIATYYCQQ VLDLPLTFGGGTKVEIK(SEQ ID NO: 26) |
| ADI-26869 | QLQLQESGPGLVKPSETLSLTCTVSGGSISSSDYYWGW IRQPPGKGLEWIGSIYYSGSTYYNPSLKSRVTISVDTS KNQFSLKLSSVTAADTAVYYCARVRTWDAAFDIWGQGT MVTVSS(SEQ ID NO: 23) | DIQMTQSPSSLSASVGDRVTITCQASQDISNYLNWYQQKPGKAP KLLIYDASNLETGVPSRFSGSGSGTDFTFTISSLQPEDIATYYCQQ VHALPPWTFGGGTKVEIK(SEQ ID NO: 27) |
| ADI-31851 | QLQLQESGPGLVKPSETLSLTCTVSGGSISSPDYYWGW IRQPPGKGLEWIGSIVYSGYTYYNPSLKSRVTISVDTS KNQFSLKLSSVTAADTAVYYCARVRTWDQSFDIWGQGT MVTVSS(SEQ ID NO: 24) | DIQMTQSPSSLSASVGDRVTITCQAGQDISNYLNWYQQKPGKAP KLLIYDASNLETGVPSRFSGSGSGTDFTFTISSLQPEDIATYYCQQ VLELPPWTFGGGTKVEIK(SEQ ID NO: 28) |
| ADI-31853 | QLQLQESGPGLVKPSETLSLTCTVSGGSIYSESYYWGW IRQPPGKGLEWIGSIVYSGYTYYNPSLKSRVTISVDTS KNQFSLKLSSVTAADTAVYYCARVRTWDAAFDIWGQGT MVTVSS(SEQ ID NO: 25) | DIQMTQSPSSLSASVGDRVTITCQASQDISNYLNWYQQKPGKAP KLLIYDASNLETGVPSRFSGSGSGTDFTFTISSLQPEDIATYYCQQ VLELPPWTFGGGTKVEIK(SEQ ID NO: 29) |
| HZ3266-IgG1N297A | EVQLVQSGAEVKKPGATVKISCTASGFNIEDTYIHWVQ QAPGQGLEWIGRIDPANDDTKYAPKFQGRATITADTST KLLIYSASNRYTGVPDRFSGSGSGTDFTLTISSLQAEDLAVYYCQ DTAYMELSSLRSEDTAVYYCGRGLGRWFAYWGQGTLVT VSS(SEQ ID NO: 57) | GIVMTQSPDSLAVSLGERATINCKASQDVINAVAWYQQKPGQSP QHYSPPLTFGGGTKVEIK(SEQ ID NO: 58) |

TABLE 3

Sequences of heavy- and light-chains of exemplary antibodies of the invention

| Antibody | Heavy chain (HC) | Light chain (LC) |
|---|---|---|
| ADI-26789 | EVQLVESGGGLVQPGRSLRLSCAASGFTFDDYAMHWVRQAPGKGLEWVSGISW NSGDIGYADSVKGRFTISRDNAKNSLYLQMNSLRAEDTALYYCAKGGYDGSYY GMDVWGQGTTVTVSSASTKGPSVFPLAPCSRSTSESTAALGCLVKDYFPEPVTVS WNSGALTSGVHTFPAVLQSSGLYSLSSVVTVPSSSLGTKTYTCNVDHKPSNTKVD KRVESKYGPPCPPCPAPEAAGGPSVFLFPPKPKDTLMISRTPEVTCVVVDVSQEDP EVQFNWYVDGVEVHNAKTKPREEQFNSTYRVVSVLTVLHQDWLNGKEYKCKV SNKGLPSSIEKTISKAKGQPREPQVYTLPPSQEEMTKNQVSLTCLVKGFYPSDIAV EWESNGQPENNYKTTPPVLDSDGSFFLYSRLTVDKSRWQEGNVFSCSVMHEALH NHYTQKSLSLSLGK(SEQ ID NO: 30) | DIQMTQSPSSLSASVGDRVTITCQASQDISNYLNWYQQ KPGKAPKLLIYDASNLETGVPSRFSGSGSGTDFTFTISSL QPEDIATYYCQQVLDLPLTFGGGTKVEIKRTVAAPSVFI FPPSDEQLKSGTASVVCLLNNFYPREAKVQWKVDNAL QSGNQESVTEQDSKDSTYSLSSTLTLSKADYEKHKVY ACEVTHQGLSSPVTKSFNRGEC(SEQ ID NO: 34) |
| ADI-26869 | QLQLQESGPGLVKPSETLSLTCTVSGGSISSSDYYWGWIRQPPGKGLEWIGSIYYS GSTYYNPSLKSRVTISVDTSKNQFSLKLSSVTAADTAVYYCARVRTWDAAFDIW GQGTMVTVSSASTKGPSVFPLAPCSRSTSESTAALGCLVKDYFPEPVTVSWNSGA LTSGVHTFPAVLQSSGLYSLSSVVTVPSSSLGTKTYTCNVDHKPSNTKVDKRVES KYGPPCPPCPAPEAAGGPSVFLFPPKPKDTLMISRTPEVTCVVVDVSQEDPEVQFN WYVDGVEVHNAKTKPREEQFNSTYRVVSVLTVLHQDWLNGKEYKCKVSNKGL PSSIEKTISKAKGQPREPQVYTLPPSQEEMTKNQVSLTCLVKGFYPSDIAVEWESN GQPENNYKTTPPVLDSDGSFFLYSRLTVDKSRWQEGNVFSCSVMHEALHNHYTQ KSLSLSLGK(SEQ ID NO: 31) | DIQMTQSPSSLSASVGDRVTITCQASQDISNYLNWYQQ KPGKAPKLLIYDASNLETGVPSRFSGSGSGTDFTFTISSL QPEDIATYYCQQVHALPPWTFGGGTKVEIKRTVAAPS VFIFPPSDEQLKSGTASVVCLLNNFYPREAKVQWKVD NALQSGNSQESVTEQDSKDSTYSLSSTLTLSKADYEKH KVYACEVTHQGLSSPVTKSFNRGEC(SEQ ID NO: 35) |
| ADI-31851 | QLQLQESGPGLVKPSETLSLTCTVSGGSISSPDYYWGWIRQPPGKGLEWIGSIVYS GYTYYNPSLKSRVTISVDTSKNQFSLKLSSVTAADTAVYYCARVRTWDQSFDIW GQGTMVTVSSASTKGPSVFPLAPCSRSTSESTAALGCLVKDYFPEPVTVSWNSGA LTSGVHTFPAVLQSSGLYSLSSVVTVPSSSLGTKTYTCNVDHKPSNTKVDKRVES KYGPPCPPCPAPEAAGGPSVFLFPPKPKDTLMISRTPEVTCVVVDVSQEDPEVQFN WYVDGVEVHNAKTKPREEQFNSTYRVVSVLTVLHQDWLNGKEYKCKVSNKGL PSSIEKTISKAKGQPREPQVYTLPPSQEEMTKNQVSLTCLVKGFYPSDIAVEWESN GQPENNYKTTPPVLDSDGSFFLYSRLTVDKSRWQEGNVFSCSVMHEALHNHYTQ KSLSLSLG(SEQ ID NO: 32) | DIQMTQSPSSLSASVGDRVTITCQAGQDISNYLNWYQQ KPGKAPKLLIYDASNLETGVPSRFSGSGSGTDFTFTISSL QPEDIATYYCQQVLELPPWTFGGGTKVEIKRTVAAPSV FIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC(SEQ ID NO: 36) |
| ADI-31853 | QLQLQESGPGLVKPSETLSLTCTVSGGSIYSESYYWGWIRQPPGKGLEWIGSIVYS GYTYYNPSLKSRVTISVDTSKNQFSLKLSSVTAADTAVYYCARVRTWDAAFDIW GQGTMVTVSSASTKGPSVFPLAPCSRSTSESTAALGCLVKDYFPEPVTVSWNSGA LTSGVHTFPAVLQSSGLYSLSSVVTVPSSSLGTKTYTCNVDHKPSNTKVDKRVES KYGPPCPPCPAPEAAGGPSVFLFPPKPKDTLMISRTPEVTCVVVDVSQEDPEVQFN WYVDGVEVHNAKTKPREEQFNSTYRVVSVLTVLHQDWLNGKEYKCKVSNKGL PSSIEKTISKAKGQPREPQVYTLPPSQEEMTKNQVSLTCLVKGFYPSDIAVEWESN GQPENNYKTTPPVLDSDGSFFLYSRLTVDKSRWQEGNVFSCSVMHEALHNHYTQ KSLSLSLG(SEQ ID NO: 33) | DIQMTQSPSSLSASVGDRVTITCQASQDISNYLNWYQQ KPGKAPKLLIYDASNLETGVPSRFSGSGSGTDFTFTISSL QPEDIATYYCQQVLELPPWTFGGGTKVEIKRTVAAPSV FIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC(SEQ ID NO: 37) |

TABLE 3-continued

Sequences of heavy- and light-chains of exemplary antibodies of the invention

| Antibody | Heavy chain (HC) | Light chain (LC) |
|---|---|---|
| HZ3266-IgG1 N297A | EVQLVQSGAEVKKPGATVKISCTASGFNIEDTYIHWVQQAPGQGLEWIGRIDPAN DDTKYAPKFQGRATITADTSTDTAYMELSSLRSEDTAVYYCGRGLGRWFAYWG QGTLVTVSASTKGPSVFPLAPSSKSTSGGTAALGCLVKDYFPEPVTVSWNSGAL TSGVHTFPAVLQSSGLYSLSSVVTVPSSSLGTQTYICNVNHKPSNTKVDKKVEPK SCDKTHTCPPCPAPELLGGPSVFLFPPKPKDTLMISRTPEVTCVVVDVSHEDPEVK FNWYVDGVEVHNAKTKPREEQYASTYRVVSVLTVLHQDWLNGKEYKCKVSNK ALPAPIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEALHNH YTQKSLSLSPGK(SEQ ID NO: 59) | GIVMTQSPDSLAVSLGERATINCKASQDVINAVAWYQ QKPGQSPKLLIYSASNRYTGVPDRFSGSGSGTDFTLTIS SLQAEDLAVYYCQQHYSPPLTFGGGTKVEIKRTVAAPS VFIFPPSDEQLKSGTASVVCLLNNFYPREAKVQWKVD NALQSGNSQESVTEQDSKDSTYSLSSTLTLSKADYEKH KVYACEVTHQGLSSPVTKSFNRGEC(SEQ ID NO: 60) |

TABLE 4

Nucleotide sequences of heavy- and light-chain variable regions of exemplary antibodies of the invention

| Antibody | VH DNA | VL DNA |
|---|---|---|
| ADI-26789 | GAGGTGCAGCTGGTGGAGAGCGGAGGCGGACTGGTGCAGCCTGGC AGAAGCCTGAGACTGAGCTGTGCCGCCAGCGGCTTCACCTTCGACG ACTACGCCATGCACTGGGTGAGACAGGCCCCTGGCAAAGGCCTGGA GTGGGTGAGCGGCATCAGCTGGAATAGCGGCGACATCGGCTACGCC GACAGCGTGAAGGGCAGGTTCACCATCAGCAGGGACAACGCCAAG AACAGCCTGTACCTGCAGATGAACTCCCTGAGGGCCGAGGACACCG CCCTGTACTACTGCGCCAAGGGCGGCTACGACGGCAGCTACTACGG CATGGACGTGTGGGGCCAGGGCACCACCGTGACAGTGAGCAGC (SEQ ID NO: 38) | GACATCCAGATGACCCAGAGCCCTAGCAGCCTGAGCGCCA GCGTGGGCGATAGGGTGACCATCACCTGCCAGGCCAGCCA GGACATCAGCAACTACCTGAACTGGTACCAGCAGAAGCCC GGCAAGGCCCCCAAGCTGCTGATCTACGACGCCAGCAACC TGGAGACCGGCGTGCCTAGCAGATTTAGCGGCAGCGGCAG CGGCACAGACTTCACCTTCACCATCAGCAGCCTGCAGCCCG AGGACATCGCCACCTACTACTGCCAGCAGGTGCTGGACCT GCCCCTGACCTTTGGCGGCGGCACCAAGGTGGAGATCAAG (SEQ ID NO: 42) |
| ADI-26869 | CAGCTGCAGCTGCAGGAGAGCGGACCTGGCCTGGTGAAGCCCAGCG AGACCCTGAGCCTGACCTGCACAGTGTCCGGCGGCAGCATCAGCAG CAGCGACTACTACTGGGGCTGGATCAGACAGCCCCCCGGAAAGGGC CTGGAGTGGATCGGCAGCATCTACTACAGCGGCAGCACCTACTACA ACCCCAGCCTGAAGAGCAGGGTGACCATCAGCGTGGACACCAGCA GAACCCAGTTCAGCCTGAAGCTGAGCAGCGTGACAGCCGCCGACACA GCCGTGTACTACTGCGCCAGAGTGAGGACCTGGGACGCCGCCTTCG ACATCTGGGGACAGGGCACCATGGTGACAGTGAGCAGC (SEQ ID NO: 39) | GACATCCAGATGACCCAGAGCCCTAGCAGCCTGAGCGCCA GCGTGGGCGATAGGGTGACCATCACCTGCCAGGCCAGCCA GGACATCAGCAACTACCTGAACTGGTACCAGCAGAAGCCC GGCAAGGCCCCCAAGCTGCTGATCTACGACGCCAGCAACC TGGAGACCGGCGTGCCTAGCAGATTTAGCGGCAGCGGCAG CGGCACAGACTTCACCTTCACCATCAGCAGCCTGCAGCCCG AGGACATCGCCACCTACTACTGCCAGCAGGTGCACGCCCT GCCTCCCTGGACCTTTGGCGGCGGCACCAAGGTGGAGATC AAG(SEQ ID NO: 43) |
| ADI-31851 | CAGCTGCAGCTGCAGGAAAGCGGACCAGGACTGGTGAAACCTAGCG AGACCCTGAGCCTGACCTGTACAGTGTCCGGAGGCAGCATCAGCTC CCCCGACTACTATTGGGGTTGGATCCGGCAGCCACCAGGAAAGGGC CTGGAGTGGATTGGCAGCATCGTGTACAGCGGCTACAAGCTACTACA ACCCCAGCCTGAAGAGCCGCGTGACAATCAGCGTGGACACCAGCAA GAACCAGTTCAGCCTGAAGCTGTCTTCAGTGACAGCCGCCGACACC GCAGTGTACTATTGCGCCAGGGTGCGGACTTGGGACCAGAGCTTCG ACATTTGGGGCAGGGCACCATGGTGACAGTGAGCAGC (SEQ ID NO: 40) | GACATCCAGATGACCCAGAGCCCTAGCAGCCTGAGCGCTA GCGTGGGAGATAGAGTGACCATCACTTGCCAGGCCGGCCA GGACATCAGCAACTACCTGAATTGGTACCAGCAGAAGCCC GGCAAGGCCCCTAAGCTGCTGATCTACGACGCCTCTAATCT GGAGACCGGCGTGCCTAGCAGATTCAGCGGAAGCGGCAGC GGCACAGATTTCACCTTCACCATCAGCAGCCTGCAGCCCGA GGACATCGCCACCTACTATTGCCAGCAGGTGCTGGAGCTG CCTCCTTGGACATTCGGAGGAGGAACAAAGGTGGAGATCA AG(SEQ ID NO: 44) |
| ADI-31853 | CAGCTGCAGCTGCAGGAATCAGGACCAGGACTGGTGAAGCCTAGCG AGACACTGAGCCTGACCTGTACCGTGTCGGAGGCAGCATCAGCAG CGAGAGCTACTATTGGGGTTGGATCCGGCAGCCACCAGGAAAGGGC CTGGAGTGGATTGGCAGCATCGTGTACAGCGGCTACACCTACTACA ACCCCAGCCTGAAGAGCCGCGTGACAATCAGCGTGGACACCAGCAA GAACCAGTTCAGCCTGAAGCTGTCTTCAGTGACAGCCGCCGACACC GCAGTGTACTATTGCGCCAGGGTGCGGACTTGGGACGCCGCCTTTG ACATTTGGGGCCAGGGCACAATGGTGACAGTGAGCAGC (SEQ ID NO: 41) | GACATCCAGATGACCCAGAGCCCTAGCAGCCTGAGCGCTA GCGTGGGAGATAGAGTGACCATCACTTGCCAGGCCAGCCA GGACATCAGCAACTACCTGAATTGGTACCAGCAGAAGCCC GGCAAGGCCCCTAAGCTGCTGATCTACGACGCCTCTAATCT GGAGACCGGCGTGCCTAGCAGATTCAGCGGAAGCGGCAGC GGCACAGATTTCACCTTCACCATCAGCAGCCTGCAGCCCGA GGACATCGCCACCTACTATTGCCAGCAGGTGCTGGAGCTG CCTCCTTGGACATTCGGAGGAGGAACAAAGGTGGAGATCA AG(SEQ ID NO: 45) |

TABLE 5

Exemplary heavy- and light-chain constant regions

| Heavy-chain constant region (IgG4) | Light-chain constant region (κ light chain) |
|---|---|
| ASTKGPSVFPLAPCSRSTSESTAALGCLVKDYFPEP VTVSWNSGALTSGVHTFPAVLQSSGLYSLSSVVTVP SSSLGTKTYTCNVDHKPSNTKVDKRVESKYGPPCPP CPAPEAAGGPSVFLFPPKPKDTLMISRTPEVTCVVV DVSQEDPEVQFNWYVDGVEVHNAKTKPREEQFNSTY | RTVAAPSVFIFPPSDEQLKSGTASVVCLLNNFYPR EAKVQWKVDNALQSGNSQESVTEQDSKDSTYS LSSTLTLSKADYEKHKVYACEVTHQGLSSPVTKS FNRGEC(SEQ ID NO: 47) |

TABLE 5-continued

Exemplary heavy- and light-chain constant regions

| Heavy-chain constant region (IgG4) | Light-chain constant region (κ light chain) |
|---|---|
| RVVSVLTVLHQDWLNGKEYKCKVSNKGLPSSIEKTI SKAKGQPREPQVYTLPPSQEEMTKNQVSLTCLVKGF YPSDIAVEWESNGQPENNYKTTPPVLDSDGSFFLYS RLTVDKSRWQEGNVFSCSVMHEALHNHYTQKSLSLS LGK(SEQ ID NO: 46) | |

These and other aspects and embodiments of the invention are described in the drawings (brief description of the drawings follows) and in the following detailed description of the invention and are illustrated in the following examples. Any or all of the features discussed above and throughout the application may be combined in various embodiments of the invention. The following examples further illustrate the invention. However, it is to be understood that the examples are described by way of illustration and not limitation, and various modifications may be made by those skilled in the art.

EXAMPLES

Example 1. Screening for Fully Humanized Anti-LAG-3 Antibodies by Yeast Display Yeast-based antibody presentation libraries were amplified according to prior art (described in WO 2009036379, WO 2010105256, or WO 2012009568), with a diversity of $1 \times 10^9$ per library. Briefly, the first two rounds of screening employed magnetic-activated cell sorting using the MACS system available from Miltenyi. First, yeast cells (~$1 \times 10^{10}$ cells per library) from the libraries were separately incubated in FACS buffer (phosphate buffer, containing 0.1% bovine serum albumin and 100 nM biotin-labeled human LAG-3 antigens (ArcoBiosystems)) for 15 min at room temperature. The cells was then washed with 50 mL of pre-cooled FACS buffer and resuspended with 40 mL of the same buffer, followed by addition of 500 μL of streptomycin microbeads (Miltenyi LS) and incubation at 4° C. for 15 min. The mixture was centrifuged at 1000 rpm for 5 min. After discarding the supernatant, the cells were resuspended with 5 mL of FACS buffer. The resulting cell suspension was loaded on a Miltenyi LS column. After loading, the column was washed three times, with 3 mL of FACS buffer each time. The Miltenyi LS column was removed from the magnetic field and eluted with 5 mL of growth medium. The eluted yeast cells were collected and incubated overnight at 37° C.

The next round of sorting was performed using a flow cytometer, wherein approximately $1 \times 10^8$ yeast cells screened by the MACS system were washed three times with FACS buffer and co-incubated with human LAG-3 antigens labeled by a low concentration of biotin (100-1 nM) at room temperature. The supernatant was discarded. The cells were washed twice with FACS buffer and mixed with LC-FITC (FITC-labeled goat anti-human immunoglobulin F(ab') kappa chain antibody, Southern Biotech) (100-fold diluted), and SA-633 (streptavidin-633, Molecular Probes) (500-fold diluted) or SA-PE (streptavidin-phycoerythrin, Sigma) (50-fold diluted) reagents, prior to incubation at 4° C. for 15 minutes. The cells were eluted twice with pre-cooled FACS buffer, re-suspended in 0.4 mL of buffer and transferred to a separator tube with a filter. The cells were sorted using FACS ARIA (BD Biosciences).

Yeast cells expressing anti-human LAG-3 antibody obtained by screening were shaken at 30° C. for 48 h for expressing anti-human LAG-3 antibody. After the incubation, the yeast cells were removed by centrifugation at 1300 rpm for 10 min, and the supernatant was collected. The anti-human LAG-3 antibodies in the supernatant were purified using Protein A and eluted using an acetic acid buffer at pH 2.0 prior to harvest. The purity was more than 95%.

Antibody ADI-26789 and antibody ADI-26869 were obtained from this screening.

Example 2. Affinity Optimization for Anti-Human LAG-3 Antibodies

To obtain anti-human LAG-3 antibodies with higher affinity, antibodies ADI-26789 and ADI-26869 were optimized by the following methods:

VHmut Screening

This method was to introduce mutations into antibody heavy chain regions by conventional mismatch PCR. In the PCR process, the probability of base pair mismatch raised to about 0.01 bp by adding 1 μM of highly mutated base analogs dPTP and 8-oxo-dGTP.

The resulting mismatch PCR products were constructed into a vector containing the heavy chain constant region by homologous recombination. By this method, a secondary pool with the capacity of $1 \times 10^7$ was obtained under screening pressure including LAG-3 antigen titers, unlabeled antigen competition, and competition with the parent antibodies. Three rounds of screening were successfully performed by FACS.

CDRH1/CDRH2 Screening

CDRH3 genes of progeny antibodies obtained by VHmut were constructed into a CDRH1/CDRH2 gene pool with the diversity of $1 \times 10^8$, and 3 rounds of screening were carried out for the genes. The first round of screening adopted MACS, while the second and third rounds adopted FACS.

Antibody-antigen conjugates were subjected to pressurized screening for screening out antibodies with the highest affinity.

Through the above affinity maturation process, the anti-human LAG-3 monoclonal antibodies ADI-31851 and ADI-31853 with improved affinity were obtained.

Example 3. Expression in HEK293 Cells and Purification

The amino acid sequences of the CDR regions, light and heavy chain variable regions, light and heavy chains of the 4 exemplary antibodies disclosed herein (ADI-26789, ADI-26869, ADI-31851, ADI-31853), as well as the corresponding nucleic acid sequences and numberings were set forth in the Tables 1-4 herein.

cDNA encoding the light and heavy chain amino acid sequences of anti-LAG-3 antibodies was cloned into an expression vector pTT5 respectively, according to a conventional method in the art. The expression vector containing target antibody genes and a transfection reagent PEI (Polysciences) were transiently transfected into incubated human embryonic kidney cells 293 (Invitrogen) according to a scheme provided by the manufacturer. After transfection, the medium was discarded and the cells were diluted to $4\times10^6$/mL with fresh EXPI293 medium (Gibco). The cells were incubated at 37° C., 5% $CO_2$ for 7 days, with fresh medium fed every 48 hours. After 7 days, the cells were centrifuged at 1300 rpm for 20 min. The supernatant was purified with Protein A to produce antibodies with purity greater than 95%.

The following reference antibodies used in the examples were also expressed and purified in HEK293 cells.

| Reference antibodies |
| --- |
| 25F7 |
| BAP050 |

Among them, 25F7 is a human LAG-3 antibody transiently expressed in HEK293 cells, and its sequence is identical to that of antibody "25F7" in U.S. Pat. No. US20170137514A1. BAP050 is an anti-human LAG-3 antibody transiently expressed in HEK293 cells, and its sequence is identical to that of antibody "BAP050" in U.S. Pat. No. WO2015/138920A1.

Example 4. Affinity Assay of Anti-LAG-3 Antibodies of the Invention

The equilibrium dissociation constant ($K_D$) for binding of the above 4 exemplary antibodies of the invention to human LAG-3 (hLAG-3) was measured by biological optical interferometry (ForteBio).

A ForteBio affinity assay of prior art (Estep, P., et al, High throughput solution based measurement of antibody-antigen affinity and epitope binning. MAbs, 2013.5(2):270-8) was performed Briefly, the sensor was equilibrated offline in assay buffer for 30 minutes, and on-line detection was then conducted for 60 seconds to establish a baseline. The purified antibody obtained as described above was loaded on-line onto an AHQ sensor (ForteBio) for ForteBio affinity assay. The sensor with the loaded antibody was then exposed to 100 nM of a human LAG-3 antigen (ArcoBiosystems) for 5 minutes before transferring the sensor to the assay buffer for dissociation for 5 minutes for dissociation rate measurement. Kinetic analysis was performed using a 1:1 binding model.

In the assay described above, the affinities of ADI-26789, ADI-26869, ADI-31851, ADI-31853 and reference antibodies 25F7 and BAP050 were shown in Table 6.

TABLE 6

Binding kinetics of the antibodies of the invention as determined by biological optical interferometry

| Antibody | The antibody was on an AHQ tip, and the human LAG-3-His was in solution (100 nM) [the univalent affinity, the equilibrium dissociation constant $K_D$ (M)] | Association constant ($M^{-1}S^{-1}$) | Dissociation constant ($S^{-1}$) |
| --- | --- | --- | --- |
| ADI-26789 | 1.83E−08 | 2.12E+05 | 3.89E−03 |
| ADI-26869 | 7.88E−09 | 4.88E+05 | 3.85E−03 |
| ADI-31851 | 6.06E−10 | 3.30E+05 | 2.00E−04 |
| ADI-31853 | 6.22E−10 | 3.22E+05 | 2.00E−04 |
| 25F7 | 9.02E−09 | 1.12E+05 | 1.01E−03 |
| BAP050 | 8.44E−10 | 2.37E+05 | 2.00E−04 |

It can be seen that all of the 4 exemplary antibodies of the invention showed very high affinity, among them, antibodies ADI-31851 and ADI-31853 had higher affinity than the reference antibody 25F7 and similar affinity to the reference antibody BAP050.

Example 5. Binding of Anti-LAG-3 Antibodies of the Invention to Human LAG-3

The binding of the 4 exemplary antibodies of the invention described above to human LAG-3 was measured in a flow cytometry-based assay. 293 cells (293-hLAG-3 cells) over-expressing human LAG-3 were generated by transfecting human embryonic kidney 293 cells (Invitrogen) with pCHO1.0 vectors (Invitrogen) carrying human LAG-3 cDNA (Sino Biological) cloned into multiple cloning sites (MCSs). 293-hLAG-3 cells ($0.2\times10^6$ cells) were mixed with different concentrations of antibodies (ADI-26789, ADI-26869 and reference 25F7) prepared as described above (the antibodies were serially three-fold diluted from a maximum concentration of 500 nM in PBS containing 0.1% bovine serum albumin (BSA) until the 8th concentration). The cells were incubated on ice for 30 min. The cells were then washed at least twice prior to addition of a secondary antibody (a PE-labeled goat anti-human IgG antibody, Southern Biotech, final concentration 5 μ/mL) diluted in 1:100, and incubated on ice (protected from light) for 30 minutes. The cells were washed at least twice and analyzed by flow cytometry. The flow cytometry assay was performed on an Accuri C6 system (BD Biosciences), and a concentration-dependent curve was fitted with GraphPad according to the mean fluorescence intensity (MFI).

In the assay described above, ADI-26789 and ADI-26869 bound to hLAG-3 overexpressed on HEK293 cells with EC50 values of 2.137 nM and 2.909 nM, respectively, and their binding capacity was superior to that of reference antibody 25F9 (with an EC50 value of 3.339 nM) (see FIG. 1).

Figure 2:
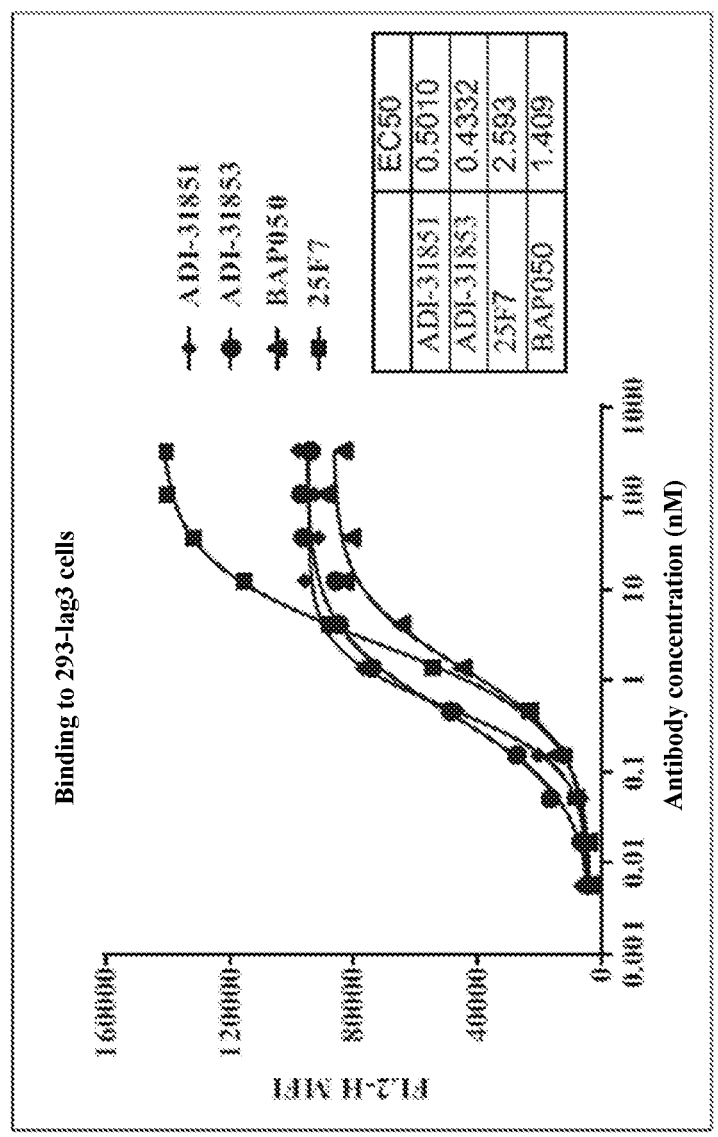
FIG. 2 shows the binding capacity of an affinity-matured antibody to hLAG-3 on the cell surface as measured by flow cytometry.

The anti-hLAG-3 antibodies ADI-31851 and ADI-31853 with optimized affinity bound to hLAG-3 overexpressed on HEK293 cells with EC50 values of 0.501 nM and 0.4332 nM, respectively, and their binding capacity was superior to that of reference antibodies 25F7 and BAP050 (with EC50 values of 2.593 nM and 1.409 nM, respectively) (see FIG. 2).

Example 6. Blockade of Interaction Between Human LAG-3 Ligands MHC II and LAG-3 by Anti-LAG-3 Antibodies of the Invention The ability of ADI-31851 and ADI-31853 to block binding of human LAG-3 to MHC II (HLA) on the cell surface was measured by flow cytometry.

The CHO cells (CHO-DR cells) overexpressing human HLA-DR were generated by transfecting CHO-S cells (Invitrogen, ExpiCHO™ Expression System Kit, Catalog No. A29133) with pCHO1.0 vectors (Invitrogen) that carry two pieces of DNA, HLA-DR-alpha and HLA-DR beta 1, having the sequences as described below.

HLA-DRβ1

(SEQ ID NO: 49)
atggtgtgtctgaagctccctggaggctcctgcatgacagcgctgacagtg
acactgatggtgctgagctccccactggctttgtctggggacacccgacca
cgtttcctgtggcagcctaagagggagtgtcatttcttcaatgggacggag
cgggtgcggttcctggacagatacttctataaccaggaggagtccgtgcgc
ttcgacagcgacgtgggggagttccgggcggtgacggagctggggcggcct
gacgctgagtactggaacagccagaaggacatcctggagcaggcgcgggcc
gcggtggacacctactgcagacacaactacggggttgtggagagcttcaca
gtgcagcggcgagtccaacctaaggtgactgtatatccttcaaagacccag
cccctgcagcaccacaacctcctggtctgctctgtgagtggtttctatcca
ggcagcattgaagtcaggtggttcctgaacggccaggaagagaaggctggg
atggtgtccacaggcctgatccagaatggagactggaccttccagacctg
gtgatgctggaaacagttcctcgaagtggagaggtttacacctgccaagtg
gagcacccaagcgtgacaagccctctcacagtggaatggagagcacggtct
gaatctgcacagagcaagatgctgagtggagtcgggggctttgtgctgggc
ctgctcttccttggggccgggctgttcatctacttcaggaatcagaaagga
cactctggacttcagccaacaggattcctgagctga

HLA-DR-N (SEQ ID NO: 50)
atggccataagtggagtccctgtgctaggattttcatcatagctgtgctg
atgagcgctcaggaatcatgggctatcaaagaagaacatgtgatcatccag
gccgagttctatctgaatcctgaccaatcaggcgagtttatgtttgacttt
gatggtgatgagattttccatgtggatatggcaaagaaggagacggtctgg
cggcttgaagaatttggacgatttgccagctttgaggctcaaggtgcattg
gccaacatagctgtggacaaagccaacctggaaatcatgacaaagcgctcc
aactatactccgatcaccaatgtacctccagaggtaactgtgctcacaaac
agccctgtggaactgagagagcccaacgtcctcatctgtttcatagacaag
ttcaccccaccagtggtcaatgtcacgtggcttcgaaatggaaaacctgtc
accacaggagtgtcagagacagtcttcctgcccagggaagaccaccttttc
cgcaagttccactatctcccttcctgccctcaactgaggacgtttacgac
tgcagggtggagcactgggcttggatgagcctcttctcaagcactgggag
tttgatgctccaagccctctcccagagactacagagaacgtggtgtgtgcc
ctgggcctgactgtgggtctggtgggcatcattattgggaccatcttcatc
atcaagggattgcgcaaaagcaatgcagcagaacgcaggggcctctgtaa Antigen rhLAG3 protein (huFc) (Sino Biological) was diluted to 40 nM, 50 μL/well. The antibodies (ADI-31851, ADI-31853, and reference 25F9) prepared as described above were 3-fold diluted in gradient from a maximum concentration of 80 nM, for a total of 8 dilution gradients. 50 μL of the diluted antibodies was added to each well, and incubated in PBS on ice for 30 min. The final antigen concentration was 20 nM and the maximum antibody concentration was 40 nM. The CHO-DR cells were adjusted to $3\times10^5$ cells/well, 100 μL/well. The cells were centrifuged at 300 g for 5 min. The supernatant was discarded. Then the cells were resuspended in an antigen-antibody mixture. The mixture was incubated on ice for 30 min. PBS was added, 100 μL/well. After centrifugation at 300 g for 5 min, the mixture was washed with PBS once. 100 μL of goat anti-human IgG-PE (Southern Biotech) diluted in 1:100 was added to each well. After a 20-min ice bath, PBS was added, 100 μL/well. The mixture was centrifuged at 300 g for 5 min, prior to one wash with PBS. The cells were resuspended with 100 μL of PBS. The cell fluorescence signal values were measured by flow cytometry (BD Biosciences).

Figure 3:
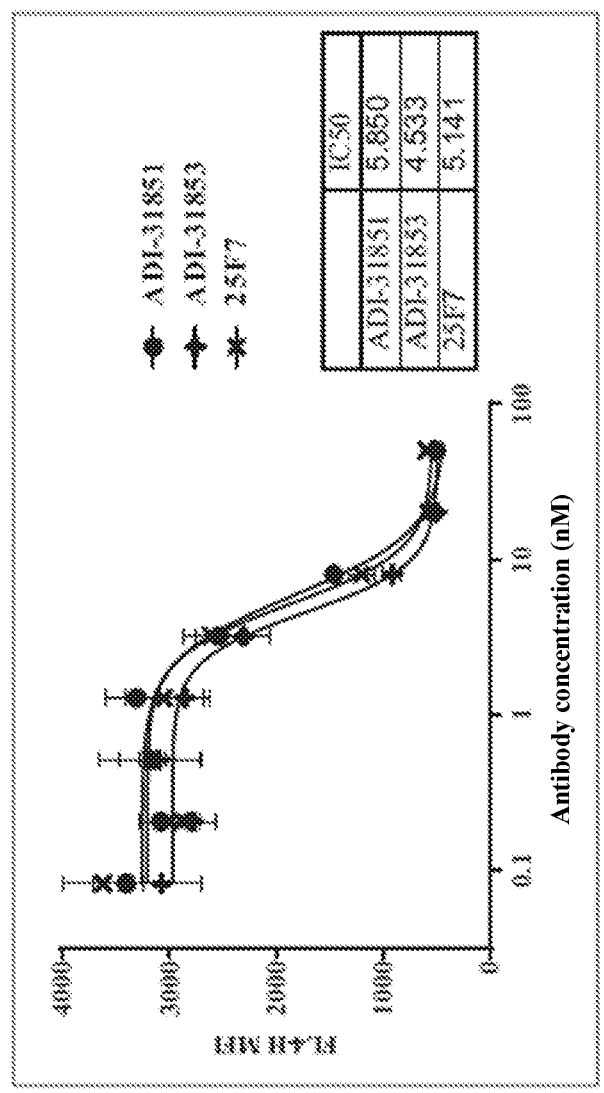
FIG. 3 shows the blockade of the interaction between human MHC II (HLA-DR) and LAG-3 by an anti-LAG-3 antibody as measured by flow cytometry.

The results showed that both ADI-31851 and ADI-31853 could effectively block the binding of LAG-3 to its ligand MHC II (HLA-DR), and their blocking ability was consistent with that of the reference antibody 25F9. Specifically, ADI-31851 and ADI-31853 blocked binding of human LAG-3 to MHC II (HLA-DR) with $IC_{50}$ of 5.85 nM and 4.533 nM, respectively. The reference antibody 25F9 blocked the binding of human LAG-3 to MHCII (HLA-DR) with an $IC_{50}$ of 5.14 nM (see FIG. 3).

Example 7. Binding of Antibodies to Activated T Cells

LAG-3 protein was expressed on the surface of human $CD4^+$ T cells when activated. The binding capacity of ADI-31851 and ADI-31853 to activated human $CD4^+$ T cells was measured by flow cytometry in this study.

PBMC isolation: 2.5-fold PBS was added into 50 mL of fresh blood from a donor. The mixture was gently added to FiColl (Thermo) and aliquoted into 4 tubes with 12.5 mL each tube. The samples were centrifuged at 400 g for 30 min before stopping at a deceleration of 0. The intermediate white strip was pipetted into PBS and washed twice with PBS.

CD4+ T cell isolation: This was performed according to the 'Untouched CD4+ T cell isolation' kit instructions (11346D, Invitrogen). PBMCs were left for 2 h before the cell suspension was pipetted into a 15-mL centrifugation tube. The cells were centrifuged at 200 g for 10 min, and the precipitate was resuspended with 500 μL of a separating medium, 100 μL of AB type serum and 100 μL of purified antibody. The mixture was incubated for 20 min at 4° C., and washed once with the separating medium. 500 μL of a Bead Buffer (Invitrogen) was added for an incubation of 15 min, and the beads were then removed by a magnetic field. The mixture was washed once with a T cell culture medium, and resuspended with 8 mL of a culture medium. The resulting mixture was then incubated at 37° C. in presence of 6% $CO_2$.

According to the ratio of magnetic beads to $CD4^+$ T cells equivalent to 1:1, anti-CD3/CD28 magnetic beads (Gibco) were added to $CD4^+$ T cells for stimulation for 3 days. The cell density was adjusted to $1\times10^6$/mL. The cells were loaded into a first well, 150 μL/well, and into other wells, 100 μL/well. Antibodies ADI-31851 and ADI-31853 prepared as described above and reference antibody 25F7 were added to the first column of wells, respectively, to reach a final concentration of 10 nM. The samples were mixed well. 50 μL of the mixture was pipetted into the next column of wells, and so on. Three replicate wells were made for each sample. The cells were centrifuged at 400 g for 5 min after an ice bath for 30 min PBS washing was performed twice before adding 50 μL of PE-anti-human Fc antibody (Southern Biotech) diluted in 1:100. After an ice bath for 30 min, the cells were centrifuged at 400 g for 5 min, followed by PBS washing twice. The mixture was resuspended in 60 µL of PBS and analyzed by flow cytometry. The flow cytometry was performed on an Accuri C6 system (BD Biosciences), and a concentration-dependent curve was fitted with Graph-Pad according to the mean fluorescence intensity (MFI).

Figure 4:
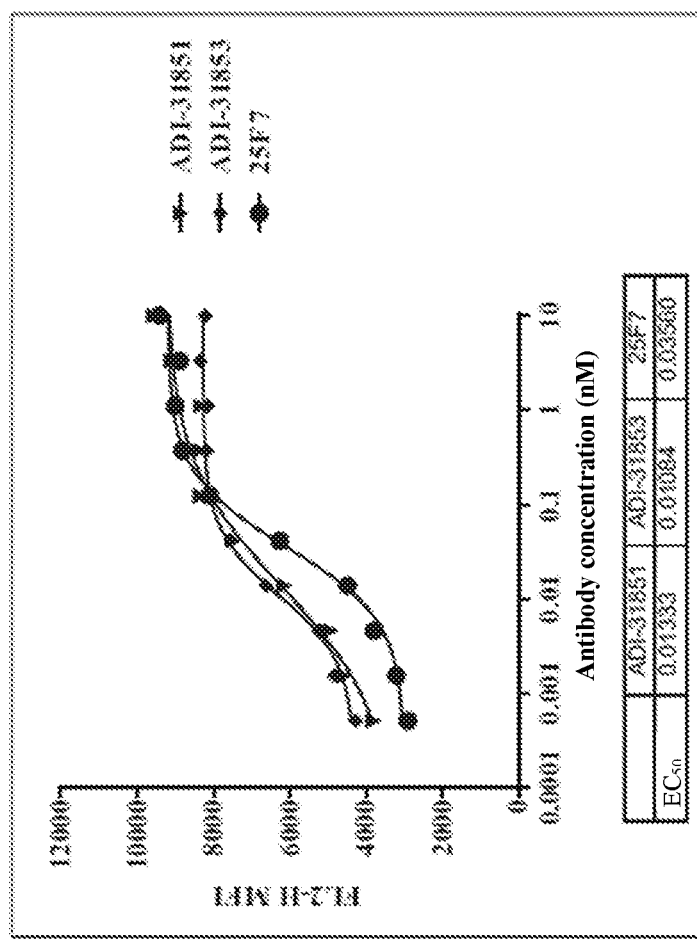
FIG. 4 shows the binding capacity of the anti-LAG-3 antibody to activated human CD4+ T cells as measured by flow cytometry.

The results showed that ADI-31851 and ADI-31853 could bind to activated human $CD4^+$ T cells with EC50 values of 0.013 nM and 0.011 nM, respectively, and their binding capacity was superior to that of the reference antibody 25F7 (with an EC50 value of 0.036 nM) (see FIG. 4).

Example 8. Binding of Anti-LAG-3 Antibodies of the Invention to Mouse LAG-3

The binding of the 2 exemplary antibodies of the invention, ADI-31851 and ADI-31853, to mouse LAG-3 was measured in a flow cytometry-based assay.

The CHO cells (CHO-mLAG-3 cells) overexpressing mouse LAG-3 were generated by transfecting CHO-S cells (Invitrogen, ExpiCHO™ Expression System Kit, Catalog No. A29133) with pCHO1.0 vectors that carry mouse LAG-3 cDNA (Sino Biological) cloned into multiple cloning sites (MCSs).

CHO-mLAG-3 cells ($0.2 \times 10^6$ cells) were mixed with different concentrations of antibodies (ADI-31851, ADI-31853 and reference 25F7 and BAP050) prepared as described above (the antibodies were serially three-fold diluted from the maximum concentration of 500 nM in PBS containing 0.1% bovine serum albumin (BSA) until the 8th concentration). The cells were incubated on ice for 30 min. The cells were then washed at least twice prior to addition of a secondary antibody (a PE-labeled goat anti-human IgG antibody, Southern Biotech, final concentration 5 µ/mL) diluted in 1:100, and incubated on ice (protected from light) for 30 minutes. The cells were washed at least twice and analyzed by flow cytometry. The flow cytometry assay was performed on an Accuri C6 system (BD Biosciences), and a concentration-dependent curve was fitted with GraphPad according to the mean fluorescence intensity (MFI).

Figure 5:
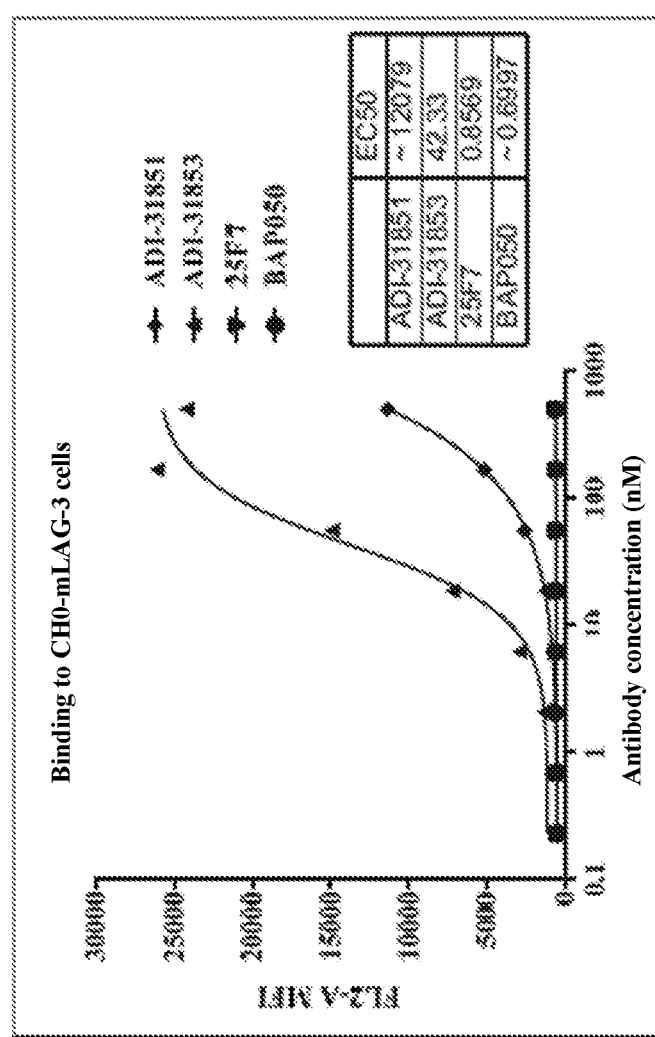
FIG. 5 shows the binding capacity of the anti-LAG-3 antibody to mouse LAG-3 on the cell surface as measured by flow cytometry.

In the assay described above, anti-hLAG-3 antibodies ADI-31851 and ADI-31853 with the optimized affinity were able to bind mouse LAG-3 over-expressed on CHO cells; the binding capacity of ADI-31853 (EC50=42.33 nM) was superior to that of ADI-31851. While neither reference antibody 25F7 nor BAP050 could bind to mouse LAG-3 over-expressed on CHO cells. (see FIG. 5)

Example 9. Anti-Tumor Activity of Anti-LAG-3 Antibodies of the Invention

In this study, the anti-tumor activity of the anti-human LAG-3 antibody ADI-31853 alone or in combination with the anti-mouse PD-1 antibody "Antibody C" (WO2017/133540) was studied using a mouse model of CT26 transplantation tumor.

Mice:
BALB/c mice (approximately 8 weeks old), female, were purchased from Beijing Vital River Laboratory Animal Technology Co., Ltd. Before the study, the mice were adapted for 7 days after arrival.

Cells:
The mouse colon cancer cell CT26 (ATCC #CRL-2638) were purchased from ATCC and were subcultured in strict accordance to the requirement provided by ATCC for further in-vivo assays. The cells were collected by centrifugation and resuspended in sterile PBS, with the cell density adjusted to $5 \times 10^6$ cells/mL. On day 0, 0.2 mL of the cell suspension was subcutaneously inoculated into the right abdominal region of BALB/c mice (Beijing Vital River Laboratory Animal Technology Co., Ltd) to establish a tumor-bearing mouse model.

Administration:
Mice were divided into four groups (8 mice per group) and each group was injected subcutaneously with the following doses of antibodies:
(1) Mouse IgG (equitech-Bio), 10 mg/kg;
(2) PD-1 (Antibody C), 1 mg/kg;
(3) LAG-3 (ADI-31853), 10 mg/kg;
(4) LAG-3 (ADI-31853), 10 mg/kg and PBS+PD-1 (Antibody C), 1 mg/kg.

Injection:
On the 7th day after grafting, the mice meeting the experimental requirements were randomly grouped, 8 mice per group. The mice in each group were administrated with the four regimens on Days 7, 10, 14 and 17 at the above doses respectively.

Analysis
The tumor volume and the body weight were measured twice a week throughout the study, and the mice were euthanized when tumors reached an endpoint (the tumor volume is greater than 2,500 $mm^3$), or when the mice had more than 20% of weight loss. The maximum length of major axis (L) and maximum length of minor axis (W) of tumors were measured with a vernier caliper, and the tumor volume was calculated using the following formula: $V = L \times W^2/2$. The tumor volume over time of the mice in various group was plotted. Statistical significance was determined using analysis of variance (ANOVA). A P value below 0.05 was considered statistically significant in all analyses. The analyses were performed using Prism 5 statistical software (GraphPad software).

Figure 6:
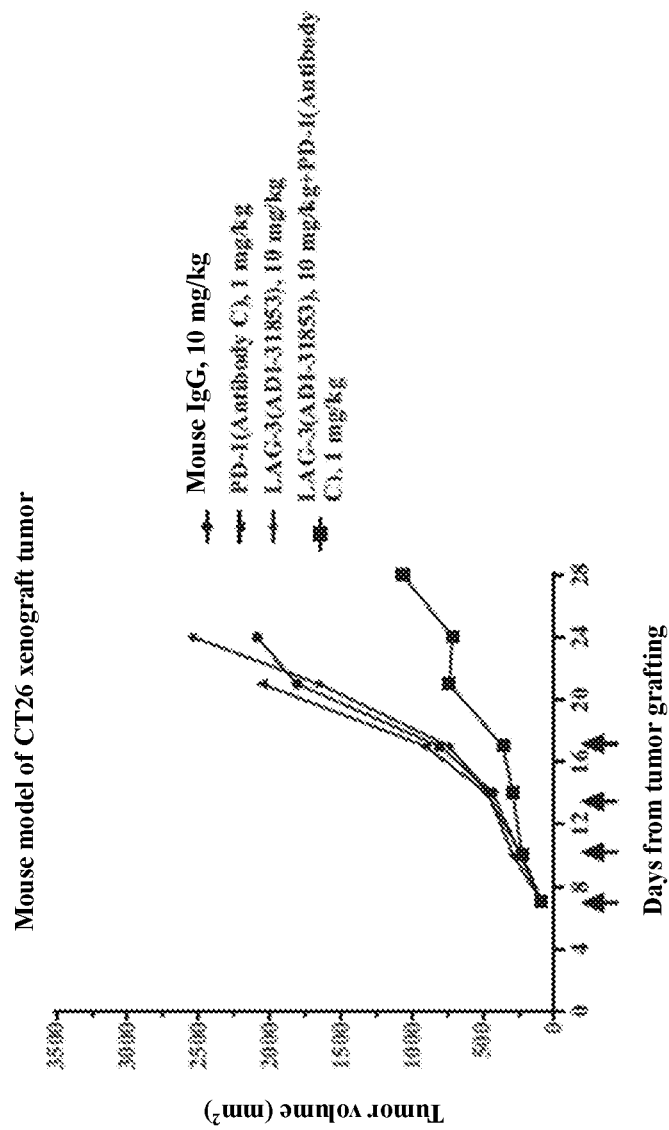
FIG. 6 shows the tumor-inhibition effect of an anti-LAG-3 antibody used in combination with an anti-PD-1 antibody in a CT26 transplanted tumor model.

As shown in FIG. 6, it can be seen that the combined use of the anti-LAG-3 monoclonal antibody ADI-31853 and the anti-PD-1 monoclonal antibody "Antibody C" significantly inhibited tumor growth compared to the use of an IgG control (equitech-Bio) and the separate use of the two antibodies.

Example 10. Anti-Tumor Activity of Anti-LAG-3 Antibodies of the Invention in Combination with Other Antibodies In this study, the anti-tumor activity of the combined use of the anti-human LAG-3 antibody ADI-31853 and the anti-PD-1 antibody "Antibody D" (IBI308, WO2017/025016) or the anti-PD-L1 antibody (HZ3266-IgG1N297A) was tested in a mouse humanized mouse model.

In this study, the anti-tumor efficacy of the anti-LAG-3 antibody was tested in NOG mice bearing A375 (ATCC) human skin cancer cells. Human PBMCs (All Cells) ($2 \times 10^6$ cell/mouse) were intravenously injected in advance, and then A375 tumor-bearing mouse models (NOG models) were established through subcutaneous grafting. The mice were grouped after tumor formation and treatments with different antibodies were given. The changes in tumor size and body weight of the mice were monitored during the treatment period. The treatments were given twice a week for 2 weeks with a total of 5 doses. The monitoring frequency was twice a week for 4 weeks. Dosages and route of administration are shown in Table 2. The tumor growth inhibition (TGI %) was calculated after the end of treatment.

Anti-PD-L1 Antibody (HZ3266-IgG1N297A)

According to a conventional method in the art, cDNA encoding the light and heavy chain amino acid sequences (Table 3) of the anti-PD-L1 antibody HZ3266-IgG1N297A was cloned into an expression vector pMD20-T (Clontech), resulting in plasmids for transfection. 293F cells (Invitrogen) were passaged according to a desired transfection volume. The cell density was adjusted to $1.5 \times 10^6$ cells/mL the day before transfection. The cell density on the day of transfection was approximately $3 \times 10^6$ cells/mL. An appropriate amount of plasmids was added to F17 culture medium (Gibco, A13835-01) with 1/10 of the final volume as transfection, and mixed. An appropriate amount of polyethylenimine (PEI) (Polysciences, 23966) was added to the mixture (in a ratio of plasmids to PEI=1:3 in the 293F cells), mixed and incubated at room temperature for 10 min, resulting in a DNA/PEI mixture. After being resuspended with the DNA/PEI mixture, the cells were introduced at 36.5° C., 8% $CO_2$. After 24 h, the cells were supplemented with FEED (Sigma) with 2% of the transfection volume, and were incubated at 36.5° C., 8% $CO_2$ at 120 rpm. On Day 6 days of subculture or until a viability fell below 60%, the cells were centrifuged and the supernatant was collected and purified.

The gravity column for purification was dried at 180° C. for 4 hours after being treated with 0.5 M NaOH overnight, resulting in a purification column Glass containers were washed with distilled water and dried. Before purification, the collected cultures were centrifuged at 4500 rpm for 30 min, and the cells were discarded. The supernatant was filtered through a 0.22 μL filter. Each tube was filled with 1 mL of Protein A and equilibrated with 10 mL of binding buffer (sodium phosphate 20 mM, NaCl 150 mM, pH 7.0). The filtered supernatant was loaded to the purification column, which was then re-equilibrated with 15 mL of binding buffer. 5 mL of eluent buffer (citric acid+sodium citrate 0.1 M, pH 3.5) was added. The eluate was collected, and 80 μL of Tris-HCl was added per mL of eluate. The buffer of the collected antibodies were changed into PBS (Gibco, 70011-044) by ultrafiltration/diafiltration, and the concentrations were measured.

The equilibrium dissociation constant ($K_D$) for binding of the anti-PD-L1 antibody (HZ3266-IgG1N297A) to human PD-L1 was determined by biological optical interferometry (ForteBio). A ForteBio affinity assay of prior art was performed (Estep, P., et al, High throughput solution based measurement of antibody-antigen affinity and epitope binning. MAbs, 2013.5(2):270-8).

Half an hour before the experiment, an appropriate number of AMQ (Pall, 1506091) (for sample detection) or AHQ (Pall, 1502051) (for positive control detection) sensors depending on the number of samples were soaked in SD buffer (PBS 1×, BSA 0.1%, Tween-20 0.05%).

SD buffer, antibodies, and antigens (including human PD-L1, all purchased from Acrobiosystems) each of 100 μL were added to 96-well black polystyrene half area microplates (Greiner, 675076). The sensors were arranged according to the positions of the samples. The instrument settings were as follows: the operation procedures were Baseline, Loading ~1 nm, Baseline, Association, and Dissociation. The run time of each procedure was dependent on the rates of association and dissociation. The rotation speed was 400 rpm, and the temperature was 30° C. The $K_D$ values were analyzed by ForteBio analysis software. The measured $K_D$ value was 0.724 nM.

Mice: NOG mice, female, 7-8 weeks old (ages at tumor cell grafting), weight of 17.6-24.2 g, purchased from Beijing Vital River Laboratory Animal Technology Co., Ltd. Before the study, the mice were adapted for 7 days after arrival.

Cells: The human skin cancer cells A375(ATCC #CRL-1619) were purchased from ATCC and were subcultured in strict accordance to the requirement provided by ATCC for further in-vivo assays. The cells were collected by centrifugation and resuspended in sterile PBS, with the cell density adjusted to $30 \times 10^6$ cells/mL. The NOG mice were intravenously injected with human PBMCs, followed by right dorsal shaving and subcutaneous injections of the A375 cells at 0.2 mL/mouse. The tumor volume of the mice was measured 7 days after grafting, and mice with the tumor volume ranging from 70-71 $mm^3$ were selected and randomly divided into groups by tumor volume.

Administration: The following antibodies were injected subcutaneously in various groups:
(1) human IgG (equitech-Bio), 20 mg/kg;
(2) PD-1 (Antibody D, IBI308), 10 mg/kg;
(3) LAG-3 (ADI-31853), 10 mg/kg;
(4) LAG-3 (ADI-31853), 10 mg/kg+PD-1 (Antibody D, IBI308), 10 mg/kg;
(5) PD-L1 (HZ3266-IgG1N297A), 10 mg/kg;
(6) LAG-3 (ADI-31853), 10 mg/kg+PD-L1 (HZ3266-IgG1N297A), 10 mg/kg.

On the 7th day after grafting, the mice with average tumor sizes meeting the requirements were randomly grouped with 8 mice per group. The mice in each group were administrated with the six regimens on Days 7, 10, 14 and 17 at the above doses respectively.

Analysis: The tumor volume and body weight were measured twice a week throughout the study, and the mice were euthanized when the tumors reached the endpoint or when the mice had more than 20% of weight loss. The maximum length of major axis (L) and maximum length of minor axis (W) of tumors were measured with a vernier caliper, and tumor volume was calculated using the following formula: $V=L \times W^2/2$. The tumor volume over time of the mice in various group was plotted. Statistical significance was determined using analysis of variance (ANOVA). A P value below 0.05 was considered statistically significant in all analyses.

Figure 7:
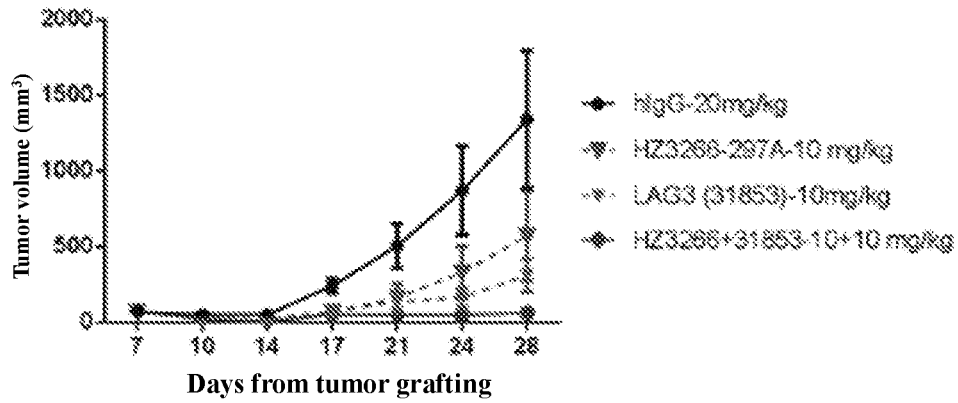
FIG. 7 shows the tumor-inhibition effect of an anti-LAG-3 antibody used in combination with an anti-PD-1 antibody or an anti-PD-L1 antibody in an NOG model.
Figure 7:
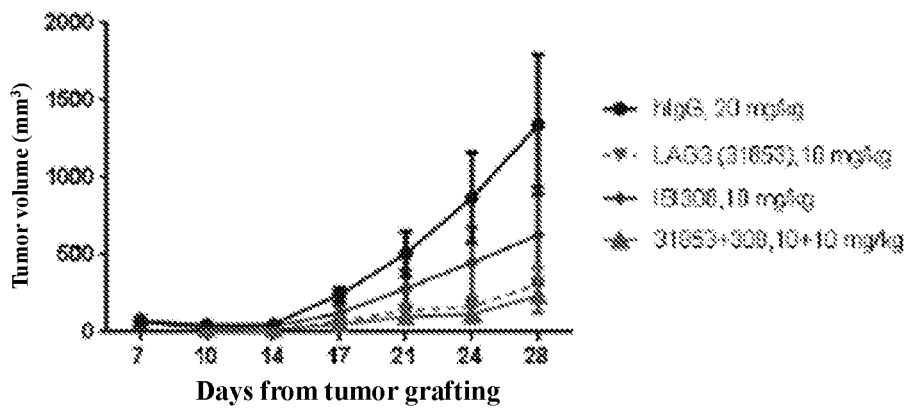

As shown in FIG. 7A or B, it can be seen that the combined use of the anti-LAG-3 monoclonal antibody ADI-31853 and the anti-PD-1 monoclonal antibody "Antibody D" (IBI308) or the anti-PD-L1 monoclonal antibody HZ3266-IgG1N297A(HZ3266) significantly inhibited tumor growth compared to the use of a human IgG reference (equitech-Bio) (hIgG) and the separate use of the two antibodies.

Example 11. Activation of Human $CD4^+$ T Cells by Anti-LAG-3 Antibodies in Combination with Anti-PD-L1 Antibodies In this experiment, the activation effect of ADI-31853 on human T cells was detected using a human $CD4^+$ T cell activation method. Human $CD4^+$ T cells activated through beads stimulation (as described in example 7) and mature DCs were co-incubated with different concentrations of ADI-31853 and 25F7 alone and in combination with the PD-L1 antibody (HZ3266-IgG1N297A, prepared as described above), respectively, for 3 days in 96-well U-shaped bottom plates. Finally, the supernatant was detected for IL-2 concentrations. The activation of T cells by ADI-31853 and 25F7, alone and in combination of the PD-L1 antibody (HZ3266-IgG1N297A, prepared as described above) were compared.

Experimental Procedures
DC Preparation

Human PBMCs (prepared as described in example 7) were taken from a liquid nitrogen tank, thawed rapidly in a 37° C. water bath, transferred to 20 mL of human T cell culture medium (containing 1‰ DNase (Sigma)), and centrifuged at 400 g for 10 min. Then, the cells were resuspended in 20 mL of human T cell culture medium (1‰ DNAse), transferred into a T75 flask, and cultured in cell incubators at 37° C., 5% CO2 for 24 h.

DC cell isolation: The suspension was discarded. 9 mL of DC culture medium was added to remaining cells for a 2-day incubation, and another 3 mL of DC culture medium was added. On day 5 of culture, rTNFa (1000 U/mL), IL-1b (5 ng/mL), IL-6 (10 ng/mL) and 1 μM PGE2 (Tocris) were added for another incubation of 2 days, resulting in DC cells for lymphocyte mix reaction (MLR). The T cell culture medium and the DC cell culture medium were both CTS AIM V SFM. The DC culture medium was supplemented with IL-4, 1000 U/mL and GM-CSF, 1000 U/mL. Catalog number and batch number were as follows:

| Reagent | Company | Catalog No. |
|---|---|---|
| CTS AIM V SFM | Gibco | A3021002 |
| Recombinant human GM-CSF | R&D Systems | 215-GM-010 |
| Recombinant human IL-4 | R&D Systems | 204-IL-010 |

Human CD4$^+$ T cell purification

Human PBMC cells (prepared as described in example 7) were removed from a liquid nitrogen tank, thawed rapidly in a 37° C. water bath, transferred to the human T cell culture medium (1‰ DNase) as described above, and centrifuged at 400 g for 10 min Human CD4$^+$ T cells were isolated and purified using the Untouched CD4$^+$ T Cell isolation kit as described in example 7, activated by Dynabeads™ Human T-Activator CD3/CD28 for T Cell Expansion and Activation, and cultured in a Cell incubator at 37° C., 5% CO$_2$ for three days.

Sample Loading

Mature DC cells were mixed with CD4+ cells at 200 μL per well, with 10000 DC cells and 100000 CD4+ cells. The antibodies (200 nM, 4-fold serial dilution, SEE (Toxin technology) 1 ng/mL) were added. The mixture of DC and CD4+ cells served as the negative control. The samples were incubated for 3 days.

The antibody concentrations utilized were as follows:

Anti-LAG-3 (ADI-31853) antibody: serially 4-fold diluted from a concentration of 200 nm until the 10th concentration Anti-PD-L1 antibody: serially 4-fold diluted from a concentration of 200 nm until the 10th concentration Reference 25F7: serially 4-fold diluted from a concentration of 200 nm until the 10th concentration Anti-LAG-3 (serially 4-fold diluted from a concentration of 200 nm until the 10th concentration)+anti-PD-L1 (12.5 nM)

Reference 25F7 (serially 4-fold diluted from a concentration of 200 nm until the 10th concentration)+anti-PD-L1 (12.5 nM)

IL-2 Detection

The concentration of IL-2 in the medium was measured using the Cisbio Human IL-2 kit.

(1) Preparation of detection solution (reagents are all from Human IL-2 1000 tests kit, Cisbio) 30 μL of Human IL-2 d2 antibody (origin) was added to 570 μL of detection buffer (origin), and 30 μL of Human IL-2 cryptate antibody (origin) was added to 570 μL of detection buffer, and the resulting two were mixed at a ratio of 1:1.

(2) Gradient dilution of standard solution

TABLE 7

Gradient dilution of IL-2 standard solution

| Gradient | Concentration (pg/mL) | Dilution method |
|---|---|---|
| 1 | 5000 | 80 μL of 15 μg/mL standard substance was added into 160 μL of diluent (1x). |
| 2 | 2500 | 80 μL of solution in gradient 1 was added to 80 μL of diluent (1x), and mixed well. |
| 3 | 1250 | 80 μL of solution in gradient 2 was added to 80 μL of diluent (1x), and mixed well. |
| 4 | 625 | 80 μL of solution in gradient 3 was added to 80 μL of diluent (1x), and mixed well. |
| 5 | 312.5 | 80 μL of solution in gradient 4 was added to 80 μL of diluent (1x), and mixed well. |
| 6 | 156.25 | 80 μL of solution in gradient 5 was added to 80 μL of diluent (1x), and mixed well. |
| 7 | 78.125 | 80 μL of solution in gradient 6 was added to 80 μL of diluent (1x), and mixed well. |
| 8 | 0 | 160 μL of diluent (1x). |

(3) Detection

Culture supernatant and standard gradient solution (10 μL) were taken and added into a 96-well microplate, and 10 μL of detection solution was added to each well. The mixture was centrifuged at 400 g for 1 min, in the absence of light, and incubated at room temperature for 2 h.

OD values were read at 616 nm and 665 nm using a multifunctional microplate reader, and analyzed.

The algorithm formula was as follows: Ratio= $OD_{665\ nm}/OD_{616\ nm} \times 10^4$ $$\Delta F\% = (Ratio_{standard/sample} - Ratio_{standard\ 0})/Ratio_{standard\ 0}$$

Results of the Experiment

Figure 8:
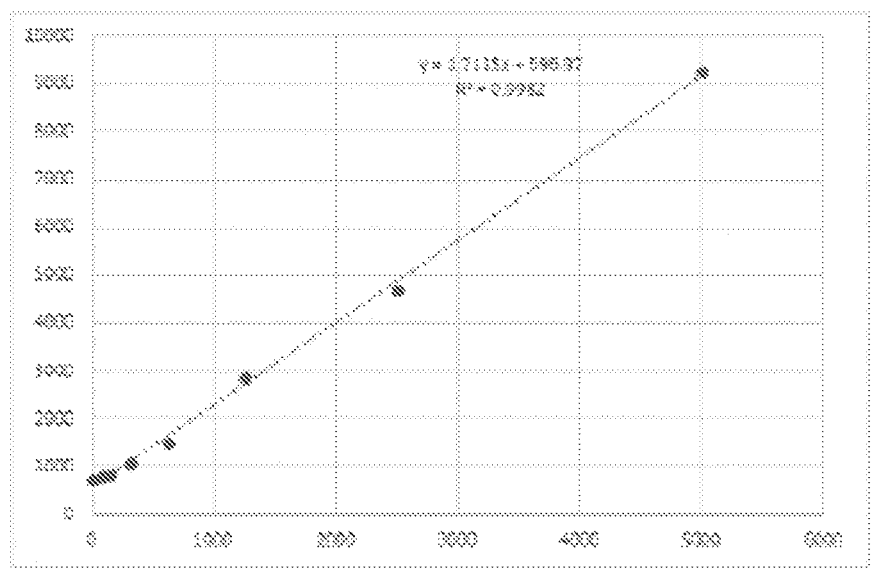
FIG. 8 shows an IL-2 standard curve.
Figure 9:
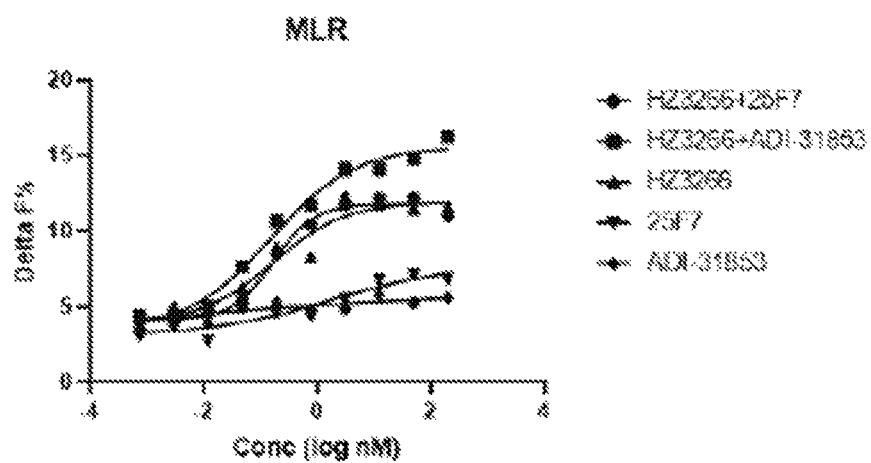
FIG. 9 shows the effect of an antibody or a combination of antibodies on IL-2 secretion from activated human CD4+ T cells.

An IL-2 standard curve was obtained by using the Delta Ratio of the gradient concentration of the standard as the abscissa and the IL-2 level as the ordinate. The IL-2 level of human CD4+ T cells in each group was calculated by the standard curve as shown in FIG. 8. As shown in FIG. 9, the anti-LAG-3 antibody (ADI-31853) of the invention in combination with the anti-PD-L1 antibody (HZ3266) activated human CD4+ T cells more significantly than either the reference (25F7) or the anti-LAG-3 antibody ADI31853 alone.

The invention claimed is:

1. An antibody or an antigen-binding fragment thereof that binds to LAG-3, the antibody comprising a heavy chain variable region and a light chain variable region, wherein the heavy chain variable region comprises HCDR1, HCDR2, HCDR3, and the light chain variable region comprises LCDR1, LCDR2 and LCDR3, wherein the HCDR1, HCDR2, HCDR3, LCDR1, LCDR2 and LCDR3 comprises or consists of the amino acid sequences respectively represented by
   (i) SEQ ID NO: 4, 7, 9, 11, 13 and 16;
   (ii) SEQ ID NO: 1, 5, 8, 11, 13 and 14;
   (iii) SEQ ID NO: 2, 6, 9, 11, 13 and 15; or
   (iv) SEQ ID NO: 3, 7, 10, 12, 13, and 16.

2. The antibody or the antigen-binding fragment thereof according to claim 1, the antibody comprising a light chain variable region and a heavy chain variable region,
   wherein the heavy chain variable region comprises or consists of
   (i) an amino acid sequence having at least 90% identity to an amino acid sequence selected from SEQ ID NOs: 25, 22, 23, or 24; or
   (ii) an amino acid sequence shown in SEQ ID NO: 25, 22, 23, or 24;
   and
   the light chain variable region comprises or consists of
   (i) an amino acid sequence having at least 90% identity to an amino acid sequence selected from SEQ ID NOs: 29, 26, 27, or 28; or
   (ii) an amino acid sequence shown in SEQ ID NOs: 29, 26, 27, or 28.

3. The antibody or the antigen-binding fragment thereof according to claim 1, the antibody comprising a light chain variable region and a heavy chain variable region, wherein
   (i) the heavy chain variable region comprises or consists of an amino acid sequence represented by SEQ ID NO: 25, and the light chain variable region comprises or consists of an amino acid sequence represented by SEQ ID NO: 29;
   (ii) the heavy chain variable region comprises or consists of an amino acid sequence represented by SEQ ID NO: 22, and the light chain variable region comprises or consists of an amino acid sequence represented by SEQ ID NO: 26; or
   (iii) the heavy chain variable region comprises or consists of an amino acid sequence represented by SEQ ID NO: 23, and the light chain variable region comprises or consists of an amino acid sequence represented by SEQ ID NO: 27; or
   (iv) the heavy chain variable region comprises or consists of an amino acid sequence represented by SEQ ID NO: 24, and the light chain variable region comprises or consists of an amino acid sequence represented by SEQ ID NO: 28.

4. The antibody or the antigen-binding fragment thereof according to claim 1, the antibody comprising:
   (a) a heavy chain
   (i) comprising or consisting of an amino acid sequence having at least 85% identity to an amino acid sequence selected from SEQ ID NOs: 33, 30, 31, and 32; or
   (ii) comprising or consisting of an amino acid sequence selected from SEQ ID NOs: 33, 30, 31, and 32;
   and
   (b) a light chain
   (i) comprising or consisting of an amino acid sequence having at least 85% identity to an amino acid sequence selected from SEQ ID NOs: 37, 34, 35, and 36; or
   (ii) comprising or consisting of an amino acid sequence selected from SEQ ID NOs: 37, 34, 35, and 36.

5. The antibody or the antigen-binding fragment thereof according to claim 1, comprising:
   (i) a heavy chain comprising or consisting of an amino acid sequence of SEQ ID NO: 33; and a light chain comprising or consisting of an amino acid sequence of SEQ ID NOs: 37;
   (ii) a heavy chain comprising or consisting of an amino acid sequence of SEQ ID NO: 30; and a light chain comprising or consisting of an amino acid sequence of SEQ ID NOs: 34;
   (iii) a heavy chain comprising or consisting of an amino acid sequence of SEQ ID NO: 31; and a light chain comprising or consisting of an amino acid sequence of SEQ ID NOs: 35; or
   (iv) a heavy chain comprising or consisting of an amino acid sequence of SEQ ID NO: 32; and a light chain comprising or consisting of an amino acid sequence of SEQ ID NOs: 36.

6. The anti-LAG-3 antibody or the antigen-binding fragment thereof according to claim 1, wherein the antibody is a monoclonal antibody, or a humanized antibody in the form of IgG4, and/or the anti-LAG-3 antibody or the antigen-binding fragment thereof comprises a κ light chain constant region.

7. The antibody or the antigen-binding fragment thereof according to claim 1, wherein the antigen-binding fragment is an antibody fragment selected from: Fab, Fab', Fab'-SH, Fv, scFv, (Fab')2 fragments, diabodies (dAbs), and linear antibodies.

8. The antibody or the antigen-binding fragment thereof of claim 1, wherein the antibody is a bispecific antibody or a multispecific antibody, wherein the bispecific antibody binds to LAG-3 and PD-1, binds to LAG-3 and PD-L1, or binds to LAG-3 and PD-L2, or the multispecific antibody comprises a first binding specificity for LAG-3 and second and third binding specificities for one or more molecules selected from PD-1, TIM-3, CEACAM, PD-L1, and PD-L2.

9. An isolated nucleic acid encoding the anti-LAG-3 antibody or the antigen-binding fragment thereof according to claim 1.

10. A vector comprising the nucleic acid according to claim 9, wherein the vector is an expression vector.

11. A host cell comprising the nucleic acid according to claim 9.

12. A method for preparing an anti-LAG-3 antibody or the antigen-binding fragment thereof, the method comprising:
incubating the host cell according to claim 11 in conditions suitable for expression of a nucleic acid encoding the anti-LAG-3 antibody or the antigen-binding fragment thereof,
expressing the antibody or antigen-binding fragment thereof from the encoding nucleic acid;
optionally the method further comprising isolating the anti-LAG-3 antibody or the antigen-binding fragment thereof from the host cell.

13. An immunoconjugate, comprising the anti-LAG-3 antibody or the antigen-binding fragment thereof according to claim 1, and a cytotoxic agent.

14. A pharmaceutical composition, comprising the anti-LAG-3 antibody or the antigen-binding fragment thereof according to claim 1, and a pharmaceutical supplementary material.

15. A pharmaceutical composition, comprising the anti-LAG-3 antibody or the antigen-binding fragment thereof according to claim 1, an additional therapeutic agent, and a pharmaceutical supplementary material, wherein, the additional therapeutic agent is selected from an anti-PD-1 antibody or an anti-PD-L1 antibody.

16. The pharmaceutical composition according to claim 15, wherein the anti-PD-L1 antibody comprises a heavy chain variable region (VH) and a light chain variable region (VL), wherein
(i) the VH comprises complementarity determining regions (CDRs) HCDR1, HCDR2 and HCDR3, wherein the HCDR1 comprises or consists of the amino acid sequence of SEQ ID NO: 51; the HCDR2 comprises or consists of an amino acid sequence of SEQ ID NO: 52; the HCDR3 comprises or consists of the amino acid sequence of SEQ ID NO: 53;
and
(ii) the VL comprises complementarity determining regions (CDRs) LCDR1, LCDR2, and LCDR3, wherein the LCDR1 comprises or consists of the amino acid sequence of SEQ ID NO: 54; the LCDR2 comprises or consists of the amino acid sequence of SEQ ID NO: 55; the LCDR3 comprises or consists of an amino acid sequence of SEQ ID NO: 56.

17. A method for treating a cancer or an infectious disease in a subject or an individual, comprising administering an effective amount of the anti-LAG-3 antibody or the antigen-binding fragment thereof according to claim 1.

18. The method according to claim 17, wherein the cancer is colon cancer; or the infectious disease is a chronic infection.

19. The method according to claim 17, further comprising administering one or more additional therapies, wherein the one or more additional therapies include therapeutic modalities and/or other therapeutic agent, wherein the therapeutic modalities include surgical treatment and/or radiotherapy, the therapeutic agent is selected from a chemotherapeutic agent, a cytotoxic agent, a vaccine, another antibody, an anti-infection agent, and an immunomodulatory agent.

20. The method according to claim 19, wherein the therapeutic agent is an anti-PD-1 antibody or an anti-PD-L1 antibody.

21. The method according to claim 20, wherein the anti-PD-L1 antibody comprises a heavy chain variable region (VH) and a light chain variable region (VL), wherein
(i) the VH comprises complementarity determining regions (CDRs) HCDR1, HCDR2 and HCDR3, wherein the HCDR1 comprises or consists of the amino acid sequence of SEQ ID NO: 51; the HCDR2 comprises or consists of an amino acid sequence of SEQ ID NO: 52; the HCDR3 comprises or consists of the amino acid sequence of SEQ ID NO: 53;
and
(ii) the VL comprises complementarity determining regions (CDRs) LCDR1, LCDR2, and LCDR3, wherein the LCDR1 comprises or consists of the amino acid sequence of SEQ ID NO: 54; the LCDR2 comprises or consists of the amino acid sequence of SEQ ID NO: 55; the LCDR3 comprises or consists of an amino acid sequence of SEQ ID NO: 56.

* * * * *